US012345671B2

(12) United States Patent
Liu et al.

(10) Patent No.: US 12,345,671 B2
(45) Date of Patent: Jul. 1, 2025

(54) ANALYTE SENSORS FOR DETECTING ASPARAGINE AND ASPARTATE AND METHODS OF USE THEREOF

(71) Applicant: Abbott Diabetes Care Inc., Alameda, CA (US)

(72) Inventors: Zenghe Liu, Alameda, CA (US); Barry S. Kreutz, Chicago, IL (US); Yagya Raj Ojha, Alameda, CA (US); Benjamin J. Feldman, Berkeley, CA (US); Thomas P. Leary, Peoria, AZ (US)

(73) Assignee: Abbott Diabetes Care Inc., Alameda, CA (US)

( * ) Notice: Subject to any disclaimer, the term of this patent is extended or adjusted under 35 U.S.C. 154(b) by 648 days.

(21) Appl. No.: 17/561,505

(22) Filed: Dec. 23, 2021

(65) Prior Publication Data

US 2022/0205944 A1 Jun. 30, 2022

Related U.S. Application Data

(60) Provisional application No. 63/132,200, filed on Dec. 30, 2020.

(51) Int. Cl.
*G01N 27/327* (2006.01)
*A61B 5/1486* (2006.01)
(Continued)

(52) U.S. Cl.
CPC ....... *G01N 27/3273* (2013.01); *A61B 5/1486* (2013.01); *C12N 9/0022* (2013.01);
(Continued)

(58) Field of Classification Search
CPC .......... G01N 27/3273; G01N 27/3272; G01N 27/3274; C12N 9/0022; C12N 9/82;
(Continued)

(56) References Cited

U.S. PATENT DOCUMENTS 6,134,461 A 10/2000 Say et al.
6,605,200 B1 8/2003 Mao et al.
(Continued)

FOREIGN PATENT DOCUMENTS

JP 2020202825 A 12/2020
WO WO-2018136898 A1 7/2018
(Continued)

OTHER PUBLICATIONS

EPO machine-generated English language translatio of JP 2020202825 A, patent published Dec. 24, 2020 (Year: 2020).*
(Continued)

*Primary Examiner* — Alexander S Noguerola
(74) *Attorney, Agent, or Firm* — STERNE, KESSLER, GOLDSTEIN & FOX P.L.L.C.

(57) ABSTRACT

The present disclosure provides an analyte sensor for use in detecting aspartate and/or asparagine. In certain embodiments, an aspartate-responsive active site of a presently disclosed analyte sensor includes an aspartate oxidase disposed upon a surface of a working electrode. In certain embodiments, an asparagine-responsive active site of a presently disclosed analyte sensor includes an enzyme system comprising an aspartate oxidase and an asparaginase disposed upon a surface of a working electrode. The present disclosure further provides methods for detecting aspartate and/or asparagine using the disclosed analyte sensors.

13 Claims, 46 Drawing Sheets

(51) Int. Cl.
*C12N 9/06* (2006.01)
*C12N 9/82* (2006.01)

(52) U.S. Cl.
CPC ............ *C12N 9/82* (2013.01); *G01N 27/3272* (2013.01); *G01N 27/3274* (2013.01)

(58) Field of Classification Search
CPC ........ C12Q 1/002; C12Q 1/004; C12Q 1/005; C12Q 1/26; A61B 5/1486
See application file for complete search history.

(56) References Cited

U.S. PATENT DOCUMENTS

| | | |
|---|---|---|
| 6,605,201 B1 | 8/2003 | Mao et al. |
| 6,736,957 B1 | 5/2004 | Forrow et al. |
| 7,501,053 B2 | 3/2009 | Karinka et al. |
| 7,754,093 B2 | 7/2010 | Forrow et al. |
| 8,268,143 B2 | 9/2012 | Liu et al. |
| 8,444,834 B2 | 5/2013 | Liu et al. |
| 8,761,857 B2 | 6/2014 | Feldman et al. |
| 9,468,402 B2 | 10/2016 | Petillo et al. |
| 2003/0042137 A1 | 3/2003 | Mao et al. |
| 2006/0079740 A1* | 4/2006 | Silver ............... A61B 5/6882 600/353 |
| 2010/0230285 A1 | 9/2010 | Hoss et al. |
| 2011/0180405 A1* | 7/2011 | Chinnayelka .... A61B 5/150389 204/403.01 |
| 2012/0323098 A1* | 12/2012 | Moein ............... A61B 5/6848 29/832 |
| 2013/0150691 A1 | 6/2013 | Pace et al. |
| 2014/0171771 A1 | 6/2014 | Feldman et al. |
| 2016/0331283 A1 | 11/2016 | Rao et al. |
| 2017/0367627 A1* | 12/2017 | Brister ............... A61B 5/1468 |
| 2018/0235520 A1 | 8/2018 | Rao et al. |
| 2019/0090797 A1 | 3/2019 | Chen et al. |
| 2019/0274598 A1 | 9/2019 | Scott et al. |
| 2020/0196919 A1 | 6/2020 | Rao et al. |
| 2020/0237275 A1 | 7/2020 | Feldman et al. |
| 2020/0237276 A1 | 7/2020 | Oja et al. |
| 2021/0204841 A1 | 7/2021 | Thomas et al. |

FOREIGN PATENT DOCUMENTS

| | | |
|---|---|---|
| WO | WO-2019236850 A1 | 12/2019 |
| WO | WO-2019236859 A1 | 12/2019 |
| WO | WO-2019236876 A1 | 12/2019 |

OTHER PUBLICATIONS

International Search Report for International Application No. PCT/US2021/065141, mailed on Apr. 28, 2022, 4 pages.

Erdogan, A., et al., "Preparation of the L-Asparaginase-Based Biosensor With Polyimide Membrane Electrode for Monitoring L-Asparagine Levels in Leukemia," Int J Polym Mater 63(17):909-917 (Jun. 2014).

Nasu, S., et al., "L-Aspartate oxidase, a newly discovered enzyme of *Escherichia coli*, is the B protein of quinolinate synthetase," J Biol Chem 257(2):626-632 (Jan. 1982).

Bifulco, D., et al., "A thermostable L-aspartate oxidase: a new tool for biotechnological applications," Appl Microbiol Biotechnol. 97(16):7285-7295 (Aug. 2013).

Washio, T., et al., "Thermostable and highly specific L-aspartate oxidase from Thermococcus litoralis DSM 5473: cloning, overexpression, and enzymological properties," Extremophiles 22(1):59-71 (Jan. 2018).

Hao, J., et al., "Characterization of l-aspartate oxidase from *Arabidopsis thaliana*," Plant Sci 271:133-142 (Jun. 2018).

Ajewole, E., et al., "Structural basis of potassium activation in plant asparaginases," FEBS J. 285(8):1528-1539 (Apr. 2018).

Bejger, M., et al., "$Na^+/K^+$ exchange switches the catalytic apparatus of potassium-dependent plant L-asparaginase," Acta Crystallogr D Biol Crystallogr. 70(Pt 7):1854-1872 (Jul. 2014).

* cited by examiner

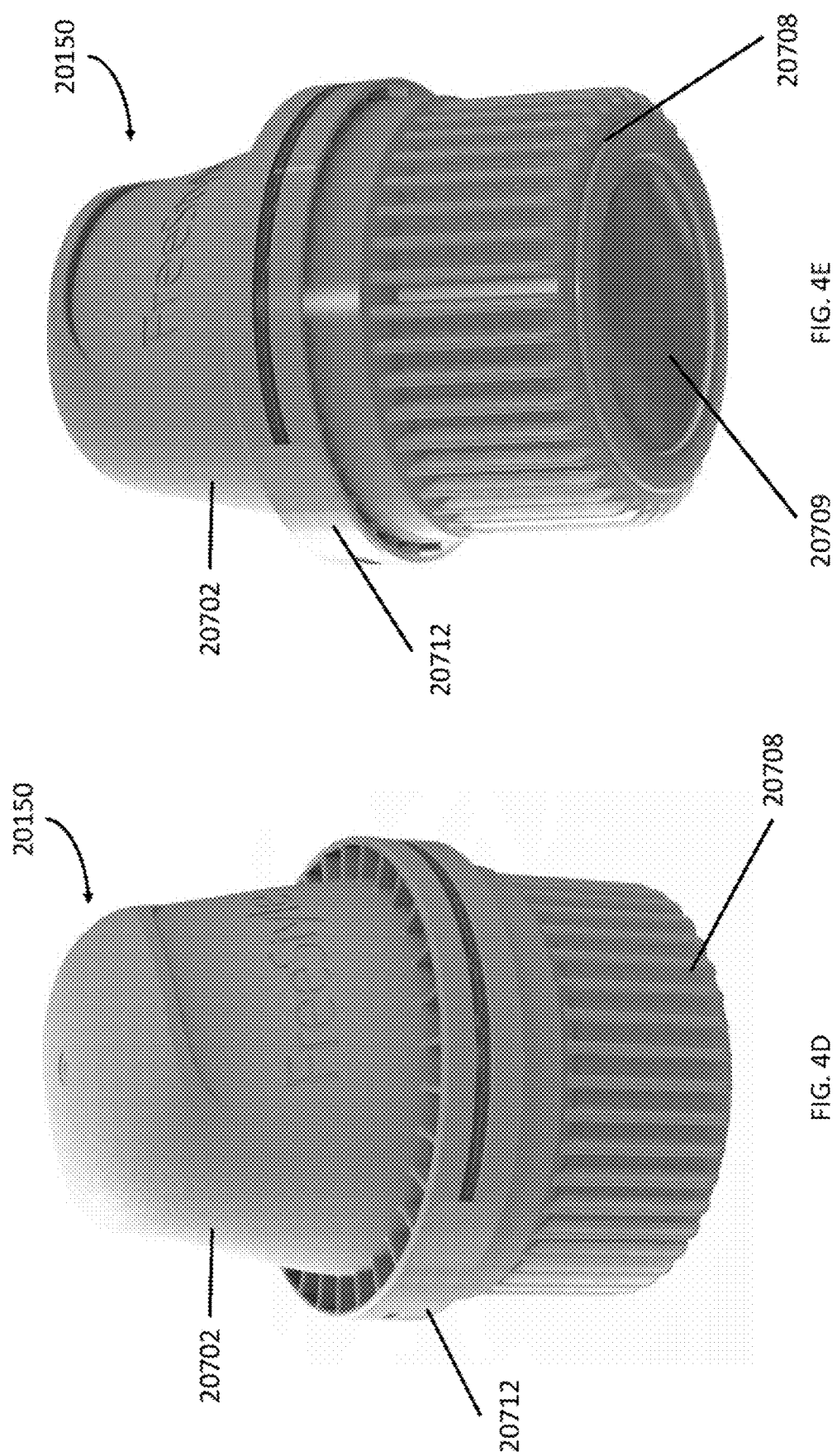

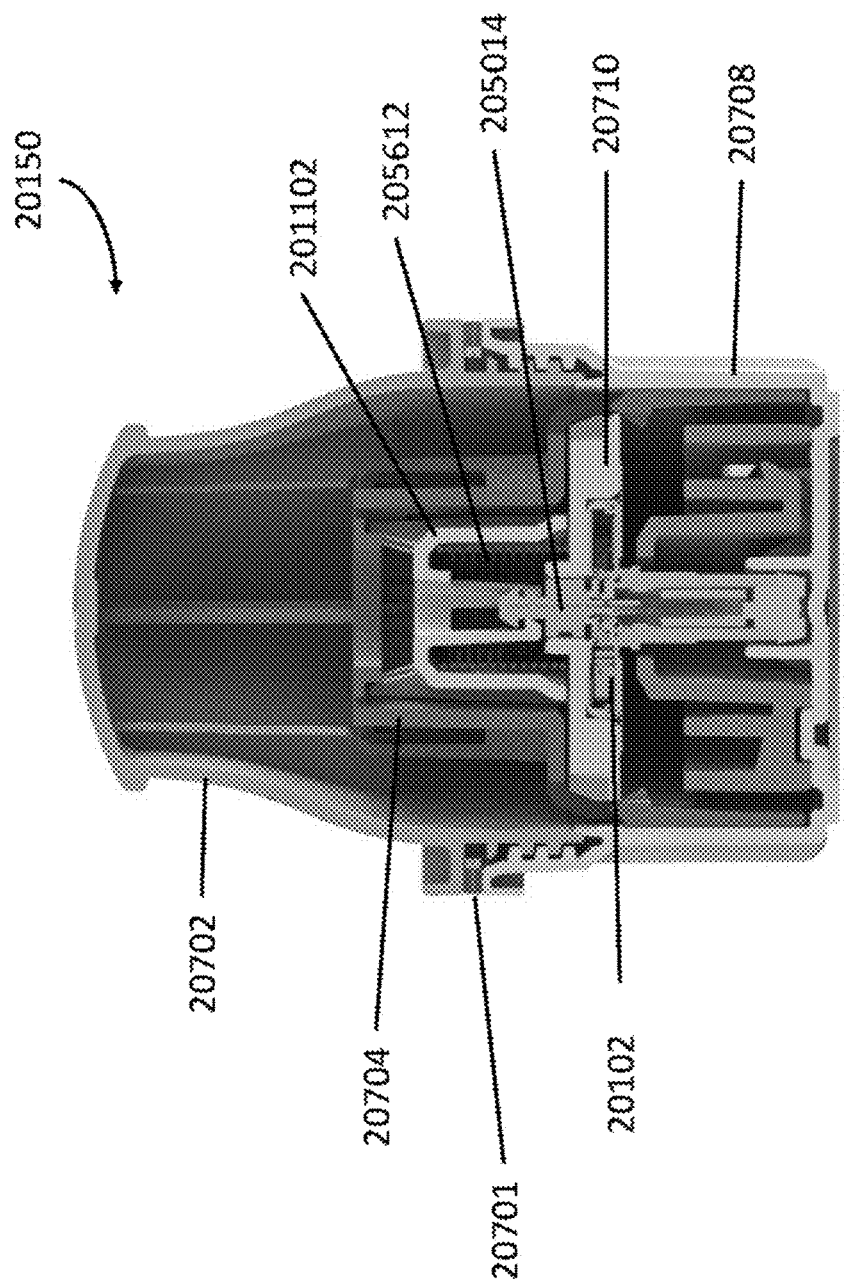

ANALYTE SENSORS FOR DETECTING ASPARAGINE AND ASPARTATE AND METHODS OF USE THEREOF

CROSS-REFERENCE TO RELATED APPLICATIONS

This application claims priority to U.S. Provisional Application No. 63/132,200, filed Dec. 30, 2020, the contents of which is incorporated by reference in its entirety.

FIELD

The subject matter described herein relates to analyte sensors for sensing asparagine and/or aspartate and methods of using the same.

BACKGROUND

The detection of various analytes within an individual can sometimes be vital for monitoring the condition of their health as deviations from normal analyte levels can be indicative of a physiological condition. For example, monitoring glucose levels can enable people suffering from diabetes to take appropriate corrective action including administration of medicine or consumption of particular food or beverage products to avoid significant physiological harm. Other analytes such as aspartate and asparagine can also be desirable to monitor. In certain instances, it can be desirable to monitor more than one analyte to monitor single or multiple physiological conditions, particularly if a person is suffering from comorbid conditions that result in simultaneous dysregulation of two or more analytes in combination with one another.

Analyte monitoring in an individual can take place periodically or continuously over a period of time. Periodic analyte monitoring can take place by withdrawing a sample of bodily fluid, such as blood or urine, at set time intervals and analyzing ex vivo. Periodic, ex vivo analyte monitoring can be sufficient to determine the physiological condition of many individuals. However, ex vivo analyte monitoring can be inconvenient or painful in some instances. Moreover, there is no way to recover lost data if an analyte measurement is not obtained at an appropriate time. Continuous analyte monitoring can be conducted using one or more sensors that remain at least partially implanted within a tissue of an individual, such as dermally, subcutaneously or intravenously, so that analyses can be conducted in vivo. Implanted sensors can collect analyte data on-demand, at a set schedule, or continuously, depending on an individual's particular health needs and/or previously measured analyte levels. Analyte monitoring with an in vivo implanted sensor can be a more desirable approach for individuals having severe analyte dysregulation and/or rapidly fluctuating analyte levels, although it can also be beneficial for other individuals as well. Since implanted analyte sensors often remain within a tissue of an individual for an extended period of time, it can be highly desirable for such analyte sensors to be made from stable materials exhibiting a high degree of biocompatibility.

Many analytes represent intriguing targets for physiological analyses, provided that a suitable detection chemistry can be identified. To this end, enzyme-based amperometric sensors configured for assaying glucose continuously in vivo have been developed and refined over recent years to aid in monitoring the health of diabetic individuals. Other analytes commonly subject to concurrent dysregulation with glucose in diabetic individuals include, for example, aspartate and asparagine. It can also be desirable to monitor aspartate and asparagine independent of glucose dysregulation as well. However, implanted analyte sensors configured for detecting aspartate or asparagine in vivo are not currently available. Accordingly, there is a need in the art for sensors for detecting asparagine or aspartate in vivo.

SUMMARY

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes an analyte sensor for detecting aspartate and/or asparagine. In certain embodiments, the analyte sensor includes a sensor tail comprising at least a first working electrode, an analyte-responsive active area disposed upon a surface of the first working electrode for detecting an analyte, wherein the analyte-responsive active area comprises aspartate oxidase; and a mass transport limiting membrane permeable to the analyte that overcoats at least the analyte-responsive active area.

In certain embodiments, the analyte is aspartate. In certain embodiments, the analyte-responsive active further includes an asparaginase and the analyte is asparagine. In certain embodiments, the analyte-responsive active area includes a layer comprising the asparaginase disposed upon a layer comprising the aspartate oxidase. In certain embodiments, the analyte-responsive active area comprises a single layer that includes the aspartate oxidase and asparaginase. In certain embodiments, one or more of the aspartate oxidase and the asparaginase are covalently bonded to a polymer in the analyte-responsive active area.

In certain embodiments, the analyte-responsive active further includes an electron-transfer agent. In certain embodiments, the mass transport limiting membrane comprises a polyvinylpyridine-based polymer, a polyvinylimidazole, a polyacrylate, a polyurethane, a polyether urethane, a silicone or a combination thereof. In certain embodiments, the mass transport limiting membrane comprises a polyvinylpyridine or a polyvinylimidazole. In certain embodiments, the mass transport limiting membrane comprises polyvinylpyridine-based polymer. In certain embodiments, the mass transport limiting membrane comprises a copolymer of vinylpyridine and styrene.

The present disclosure further provides methods for detecting aspartate. In certain embodiments, the method can include providing an analyte sensor that includes a sensor tail comprising at least a first working electrode, at least one aspartate-responsive active area disposed upon a surface of the first working electrode, wherein the aspartate-responsive active area comprises an aspartate oxidase, and a mass transport limiting membrane permeable to aspartate that overcoats at least the aspartate-responsive active area. In certain embodiments, the method further includes applying a potential to the first working electrode, obtaining a first signal at or above an oxidation-reduction potential of the aspartate-responsive active area, the first signal being proportional to a concentration of aspartate in a fluid contacting the aspartate-responsive active area and correlating the first signal to the concentration of aspartate in the fluid.

The present disclosure further provides methods for detecting asparagine. In certain embodiments, the method can include providing an analyte sensor that includes a sensor tail comprising at least a first working electrode, an asparagine-responsive active area disposed upon a surface of the first working electrode, wherein the asparagine-responsive active area includes an enzyme system comprising aspartate oxidase and asparaginase, and a mass transport limiting membrane permeable to aspartate that overcoats at least the aspartate-responsive active area. In certain embodiments, the method further includes applying a potential to the first working electrode, obtaining a first signal at or above an oxidation-reduction potential of the asparagine-responsive active area, the first signal being proportional to a concentration of asparagine in a fluid contacting the asparagine-responsive active area, and con-elating the first signal to the concentration of asparagine in the fluid.

In certain embodiments, the aspartate-responsive active area and/or the asparagine-responsive active area further include an electron transfer agent. In certain embodiments, the aspartate oxidase is covalently bonded to a polymer in the asparagine-responsive active area. In certain embodiments, the asparaginase is covalently bonded to a polymer in the asparagine-responsive active area. In certain embodiments, the asparagine-responsive active area includes a layer comprising the asparaginase disposed upon a layer comprising the aspartate oxidase. In certain embodiments, the asparagine-responsive active area comprises a single layer that includes the aspartate oxidase and asparaginase.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, without departing from the scope of this disclosure.

FIG. 4D is a top perspective view of an exemplary applicator device in accordance with the disclosed subject matter.

FIG. 4E is a bottom perspective view of the applicator device of FIG. 4D.

FIG. 4G is a side cutaway view of the applicator device of FIG. 4).

DETAILED DESCRIPTION

Figure 1A:
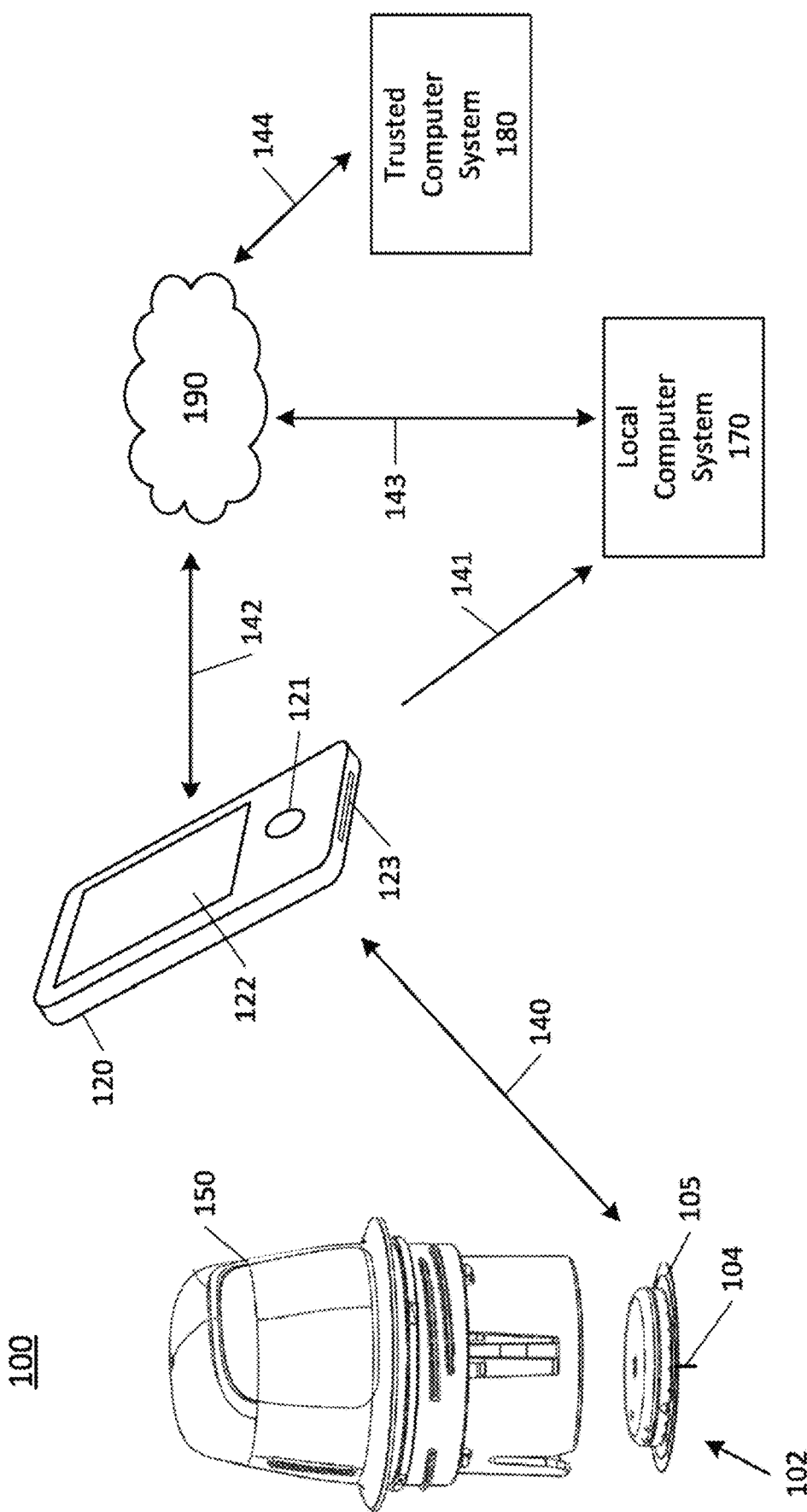
FIG. 1A is a system overview of a sensor applicator, reader device, monitoring system, network and remote system.

The present disclosure generally describes analyte sensors employing one or more enzymes for the detection of an analyte. For example, but not by way of limitation, the present disclosure provides analyte sensors for detection of an analyte, e.g., aspartate and/or asparagine. The present disclosure further provides methods of detecting one or more analytes using the disclosed analyte sensors.

The present disclosure provides sensor chemistries suitable for detecting aspartate and/or asparagine over a range of physiologically relevant aspartate and/or asparagine concentrations. In certain embodiments, the present disclosure provides analyte sensors that utilize enzyme systems comprising at least two enzymes that are capable of acting in concert to facilitate detection of an analyte, e.g., asparagine. As used herein, the term "in concert" refers to a coupled enzymatic reaction, in which a product of a first enzymatic reaction becomes a substrate for a second enzymatic reaction, and the second enzymatic reaction serves as the basis for measuring the concentration of the substrate (e.g., analyte) reacted during the first enzymatic reaction. In certain embodiments, the product and/or substrate of a reaction can be the reduced and/or oxidized form of a cofactor or coenzyme of an enzyme of the enzyme system, e.g., FAD or NAD. Although defined in terms of two coupled enzymatic reactions, it is to be appreciated that more than two enzymatic reactions can be coupled as well in some instances. For example, a product of a first enzymatic reaction can become a substrate of a second enzymatic reaction, and a product of the second enzymatic reaction can become a substrate for a third enzymatic reaction, with the third enzymatic reaction serving as the basis for measuring the concentration of the substrate (e.g., analyte) reacted during the first enzymatic reaction. Discussion of suitable enzymes and enzyme systems for detecting aspartate and/or asparagine according to the disclosure herein follows below.

In certain embodiments, an analyte sensor of the present disclosure has a sensitivity of about 0.1 to about 10 nA/mM, e.g., from about 0.1 to about 10 nA/mM, from about 0.1 to about 9 nA/mM, from about 0.1 to about 8 nA/mM, from about 0.1 to about 7 nA/mM, from about 0.1 to about 6 nA/mM, from about 0.1 to about 5 nA/mM, from about 0.1 to about 4 nA/mM, from about 0.1 to about 3 nA/mM, from about 0.1 to about 2 nA/mM or from about 0.1 to about 1 nA/mM.

For clarity, but not by way of limitation, the detailed description of the presently disclosed subject matter is divided into the following subsections:

I. Definitions; and
II. Analyte Sensors;
  1. General Structure of Analyte Sensor Systems;
  2. Enzymes;
  3. Redox Mediators;
  4. Polymeric Backbone;
  5. Mass Transport Limiting Membrane;
  6. Interference Domain; and
  7. Manufacturing;
III. Methods of Use; and
IV. Exemplary Embodiments.

I. DEFINITIONS

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the present disclosure and how to make and use them.

As used herein, the use of the word "a" or "an" when used in conjunction with the term "comprising" in the claims and/or the specification can mean "one," but it is also consistent with the meaning of "one or more," "at least one," and "one or more than one."

The terms "comprise(s)," "include(s)," "having," "has," "can," "contain(s)," and variants thereof, as used herein, are intended to be open-ended transitional phrases, terms or words that do not preclude additional acts or structures. The present disclosure also contemplates other embodiments "comprising," "consisting of" and "consisting essentially of," the embodiments or elements presented herein, whether explicitly set forth or not.

The term "about" or "approximately" means within an acceptable error range for the particular value as determined by one of ordinary skill in the art, which depends in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, "analyte sensor" or "sensor" can refer to any device capable of receiving sensor information from a user, including for purpose of illustration but not limited to, body temperature sensors, blood pressure sensors, pulse or heart-rate sensors, glucose level sensors, analyte sensors, physical activity sensors, body movement sensors, or any other sensors for collecting physical or biological information. Analytes measured by the analyte sensors can include, by way of example and not limitation, glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, asparagine, aspartate, sodium, total protein, uric acid, etc.

The term "biological fluid," as used herein, refers to any bodily fluid or bodily fluid derivative in which the analyte can be measured. Non-limiting examples of a biological fluid include dermal fluid, interstitial fluid, plasma, blood, lymph, synovial fluid, cerebrospinal fluid, saliva, bronchoalveolar lavage, amniotic fluid, sweat, tears, or the like. In certain embodiments, the biological fluid is dermal fluid or interstitial fluid.

The term "electrolysis," as used herein, refers to electrooxidation or electroreduction of a compound either directly at an electrode or via one or more electron transfer agents (e.g., redox mediators or enzymes).

As used herein, the term "homogenous membrane" refers to a membrane comprising a single type of membrane polymer.

As used herein, the term "multi-component membrane" refers to a membrane comprising two or more types of membrane polymers.

As used herein, the term "potassium-independent asparaginase" refers to an asparaginase that does not exhibit any change in catalytic activity in the presence of potassium, e.g., potassium ions (K+).

As used herein, the term "potassium-dependent asparaginase" refers to an asparaginase that exhibits increased or decreased catalytic activity in the presence of potassium, e.g., potassium ions (K+). In certain embodiments, potassium-dependent asparaginases include asparaginases that require different concentrations of potassium, e.g., potassium ions (K+), for maximum catalytic activity.

As used herein, the term "polyvinylpyridine-based polymer" refers to a polymer or copolymer that comprises polyvinylpyridine (e.g., poly(2-vinylpyridine) or poly(4-vinylpyridine)) or a derivative thereof.

As used herein, the term "redox mediator" refers to an electron transfer agent for carrying electrons between an analyte or an analyte-reduced or analyte oxidized enzyme and an electrode, either directly, or via one or more additional electron transfer agents. In certain embodiments, redox mediators that include a polymeric backbone can also be referred to as "redox polymers."

The term "reference electrode" as used herein, can refer to either reference electrodes or electrodes that function as both, a reference and a counter electrode. Similarly, the term "counter electrode," as used herein, can refer to both, a counter electrode and a counter electrode that also functions as a reference electrode.

As used herein, the term "single-component membrane" refers to a membrane including one type of membrane polymer.

II. ANALYTE SENSORS

1. General Structure of Analyte Sensor Systems

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure include systems, devices and methods for the use of analyte sensor insertion applicators for use with in vivo analyte monitoring systems. An applicator can be provided to the user in a sterile package with an electronics housing of the sensor control device contained therein. According to some embodiments, a structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. In other embodiments, the applicator, sensor control device, sensor module, and sharp module can be provided in a single package. The applicator can be used to position the sensor control device on a human body with a sensor in contact with the wearer's bodily fluid. The embodiments provided herein are improvements to reduce the likelihood that a sensor is improperly inserted or damaged, or elicits an adverse physiological response. Other improvements and advantages are provided as well. The various configurations of these devices are described in detail by way of the embodiments which are only examples.

Furthermore, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

Furthermore, the systems and methods presented herein can be used for operations of a sensor used in an analyte monitoring system, such as but not limited to wellness, fitness, dietary, research, information or any purposes involving analyte sensing over time. As used herein, "analyte sensor" or "sensor" can refer to any device capable of receiving sensor information from a user, including for purpose of illustration but not limited to, body temperature sensors, blood pressure sensors, pulse or heart-rate sensors, glucose level sensors, analyte sensors, physical activity sensors, body movement sensors, or any other sensors for collecting physical or biological information. In certain embodiments, an analyte sensor of the present disclosure can measure aspartate and/or asparagine. In certain embodiments, an analyte sensor of the present disclosure can further measure analytes including, but not limited to, glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, aspartate, asparagine, total protein, uric acid, etc.

As mentioned, a number of embodiments of systems, devices, and methods are described herein that provide for the improved assembly and use of dermal sensor insertion devices for use with in vivo analyte monitoring systems. In particular, several embodiments of the present disclosure are designed to improve the method of sensor insertion with respect to in vivo analyte monitoring systems and, in particular, to prevent the premature retraction of an insertion sharp during a sensor insertion process. Some embodiments, for example, include a dermal sensor insertion mechanism with an increased firing velocity and a delayed sharp retraction. In other embodiments, the sharp retraction mechanism can be motion-actuated such that the sharp is not retracted until the user pulls the applicator away from the skin. Consequently, these embodiments can reduce the likelihood of prematurely withdrawing an insertion sharp during a sensor insertion process; decrease the likelihood of improper sensor insertion; and decrease the likelihood of damaging a sensor during the sensor insertion process, to name a few advantages. Several embodiments of the present disclosure also provide for improved insertion sharp modules to account for the small scale of dermal sensors and the relatively shallow insertion path present in a subject's dermal layer. In addition, several embodiments of the present disclosure are designed to prevent undesirable axial and/or rotational movement of applicator components during sensor insertion. Accordingly, these embodiments can reduce the likelihood of instability of a positioned dermal sensor, irritation at the insertion site, damage to surrounding tissue, and breakage of capillary blood vessels resulting in fouling of the dermal fluid with blood, to name a few advantages. In addition, to mitigate inaccurate sensor readings which can be caused by trauma at the insertion site, several embodiments of the present disclosure can reduce the end-depth penetration of the needle relative to the sensor tip during insertion.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood analyte level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Sensor 104 is adapted to be at least partially inserted into a tissue of interest, such as within the dermal or subcutaneous layer of the skin. Sensor 104 can include a sensor tail of sufficient length for insertion to a desired depth in a given tissue. The sensor tail can include at least one working electrode. In certain configurations, the sensor tail can include at least one active area for detecting an analyte, e.g., glutamate, disposed upon the working electrode. A counter electrode can be present in combination with the at least one working electrode. Particular electrode configurations upon the sensor tail are described in more detail below.

The active area can be configured for detecting a particular analyte. In certain embodiments, the active area can be configured for detecting aspartate and/or asparagine. In certain embodiments, the active area can be configured for detecting aspartate. In certain embodiments, the active area can be configured for detecting asparagine. In certain embodiments, the active area can be configured for detecting two or more analytes. In certain embodiments, the active area can be configured for detecting asparagine and/or aspartate and/or an analyte different from asparagine and aspartate. In certain embodiments, an analyte different from asparagine and aspartate can be glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, aspartate, asparagine, total protein, uric acid, etc.

In certain embodiments of the present disclosure, one or more analytes can be monitored in any biological fluid of interest such as dermal fluid, interstitial fluid, plasma, blood, lymph, synovial fluid, cerebrospinal fluid, saliva, bronchoalveolar lavage, amniotic fluid, or the like. In certain particular embodiments, analyte sensors of the present disclosure can be adapted for assaying dermal fluid or interstitial fluid to determine a concentration of one or more analytes in vivo. In certain embodiments, the biological fluid is interstitial fluid.

An introducer can be present transiently to promote introduction of sensor 104 into a tissue. In certain illustrative embodiments, the introducer can include a needle or similar sharp. As would be readily recognized by a person skilled in the art, other types of introducers, such as sheaths or blades, can be present in alternative embodiments. More specifically, the needle or other introducer can transiently reside in proximity to sensor 104 prior to tissue insertion and then be withdrawn afterward. While present, the needle or other introducer can facilitate insertion of sensor 104 into a tissue by opening an access pathway for sensor 104 to follow. For example, and not by the way of limitation, the needle can facilitate penetration of the epidermis as an access pathway to the dermis to allow implantation of sensor 104 to take place, according to one or more embodiments. After opening the access pathway, the needle or other introducer can be withdrawn so that it does not represent a sharps hazard. In certain embodiments, suitable needles can be solid or hollow, beveled or non-beveled, and/or circular or non-circular in cross-section. In more particular embodiments, suitable needles can be comparable in cross-sectional diameter and/or tip design to an acupuncture needle, which can have a cross-sectional diameter of about 250 microns. However, suitable needles can have a larger or smaller cross-sectional diameter if needed for certain particular applications.

In certain embodiments, a tip of the needle (while present) can be angled over the terminus of sensor 104, such that the needle penetrates a tissue first and opens an access pathway for sensor 104. In certain embodiments, sensor 104 can reside within a lumen or groove of the needle, with the needle similarly opening an access pathway for sensor 104. In either case, the needle is subsequently withdrawn after facilitating sensor insertion.

B. Exemplary Reader Device

Figure 2A:
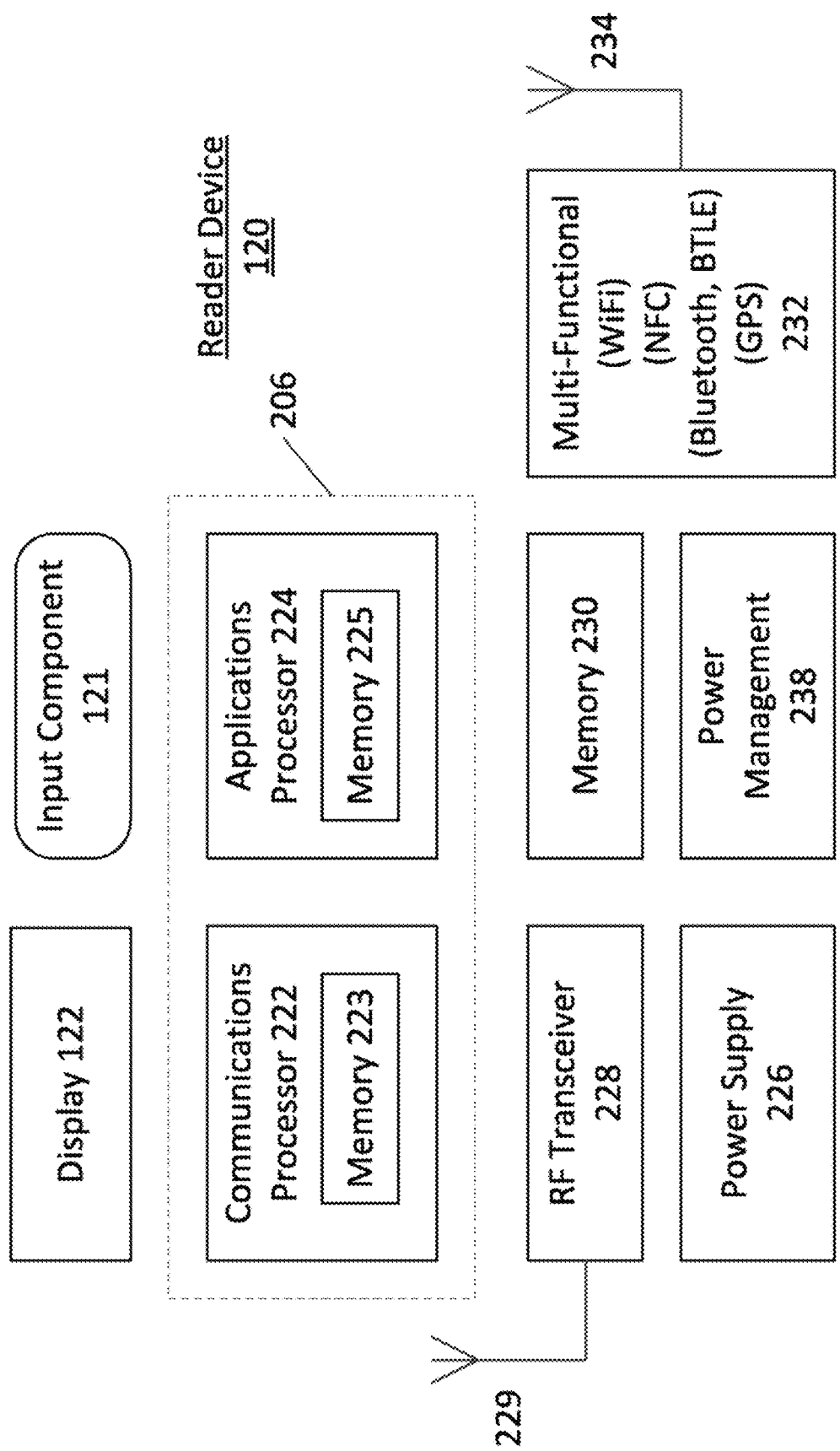
FIG. 2A is a block diagram depicting an example embodiment of a reader device.

FIG. 2A is a block diagram depicting an example embodiment of a reader device configured as a smartphone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further included can be a multi-functional transceiver 232 which can communicate over Wi-Fi, NFC, Bluetooth, BTLE, and GPS with an antenna 234. As understood by one of skill in the art, these components are electrically and communicatively coupled in a manner to make a functional device.

C. Exemplary Data Receiving Device Architecture

Figure 2B:
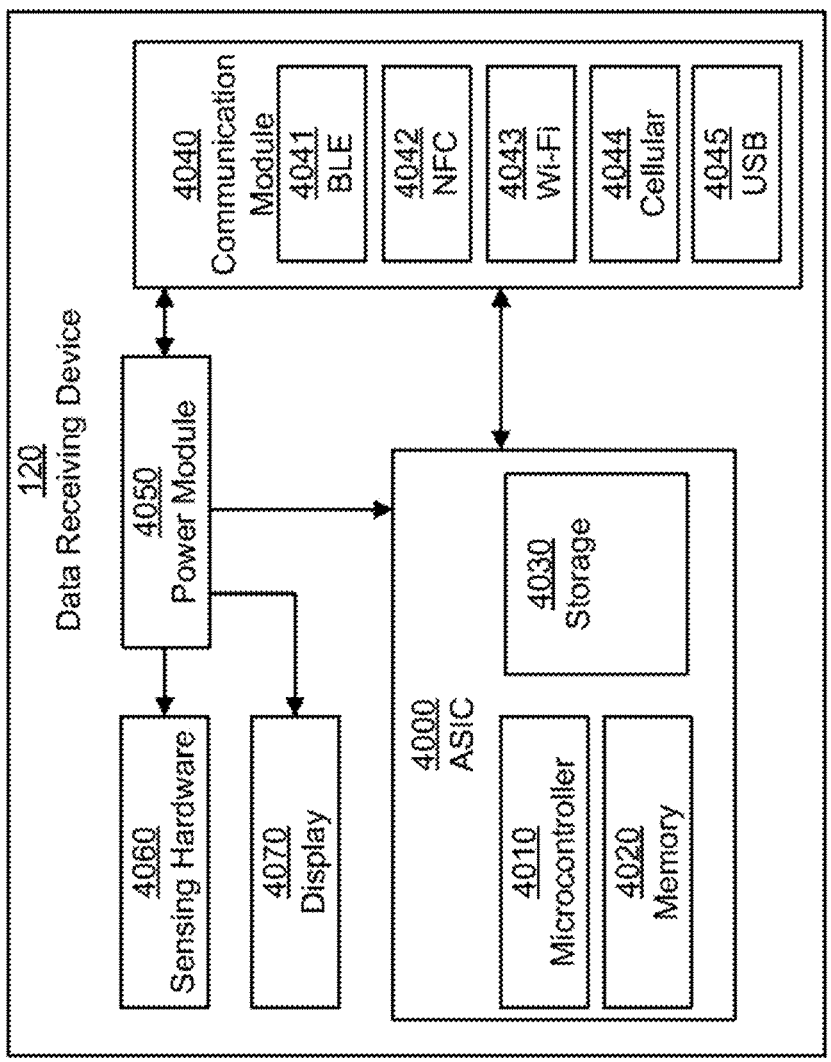
FIG. 2B is a block diagram illustrating an example data receiving device for communicating with the sensor according to exemplary embodiments of the disclosed subject matter.

For purpose of illustration and not limitation, reference is made to the exemplary embodiment of a data receiving device 120 for use with the disclosed subject matter as shown in FIG. 2B. The data receiving device 120, and the related multi-purpose data receiving device 130, includes components germane to the discussion of the analyte sensor 110 and its operations and additional components can be included. In particular embodiments, the data receiving device 120 and multi-purpose data receiving device 130 can be or include components provided by a third party and are not necessarily restricted to include devices made by the same manufacturer as the sensor 110.

As illustrated in FIG. 2B, the data receiving device 120 includes an ASIC 4000 including a microcontroller 4010, memory 4020, and storage 4030 and communicatively coupled with a communication module 4040. Power for the components of the data receiving device 120 can be delivered by a power module 4050, which as embodied herein can include a rechargeable battery. The data receiving device 120 can further include a display 4070 for facilitating review of analyte data received from an analyte sensor 110 or other device (e.g., user device 140 or remote application server 150). The data receiving device 120 can include separate user interface components (e.g., physical keys, light sensors, microphones, etc.).

The communication module 4040 can include a BLE module 4041 and an NFC module 4042. The data receiving device 120 can be configured to wirelessly couple with the analyte sensor 110 and transmit commands to and receive data from the analyte sensor 110. As embodied herein, the data receiving device 120 can be configured to operate, with respect to the analyte sensor 110 as described herein, as an NFC scanner and a BLE end point via specific modules (e.g., BLE module 4042 or NFC module 4043) of the communication module 4040. For example, the data receiving device 120 can issue commands (e.g., activation commands for a data broadcast mode of the sensor; pairing commands to identify the data receiving device 120) to the analyte sensor 110 using a first module of the communication module 4040 and receive data from and transmit data to the analyte sensor 110 using a second module of the communication module 4040. The data receiving device 120 can be configured for communication with a user device 140 via a Universal Serial Bus (USB) module 4045 of the communication module 4040.

As another example, the communication module 4040 can include, for example, a cellular radio module 4044. The cellular radio module 4044 can include one or more radio transceivers for communicating using broadband cellular networks, including, but not limited to third generation (3G), fourth generation (4G), and fifth generation (5G) networks. Additionally, the communication module 4040 of the data receiving device 120 can include a Wi-Fi radio module 4043 for communication using a wireless local area network according to one or more of the IEEE 802.11 standards (e.g., 802.11a, 802.11b, 802.11g, 802.11n (aka Wi-Fi 4), 802.11ac (aka Wi-Fi 5), 802.11ax (aka Wi-Fi 6)). Using the cellular radio module 4044 or Wi-Fi radio module 4043, the data receiving device 120 can communicate with the remote application server 150 to receive analyte data or provide updates or input received from a user (e.g., through one or more user interfaces). Although not illustrated, the communication module 5040 of the analyte sensor 120 can similarly include a cellular radio module or Wi-Fi radio module.

As embodied herein, the on-board storage 4030 of the data receiving device 120 can store analyte data received from the analyte sensor 110. Further, the data receiving device 120, multi-purpose data receiving device 130, or a user device 140 can be configured to communicate with a remote application server 150 via a wide area network. As embodied herein, the analyte sensor 110 can provide data to the data receiving device 120 or multi-purpose data receiving device 130. The data receiving device 120 can transmit the data to the user computing device 140. The user computing device 140 (or the multi-purpose data receiving device 130) can in turn transmit that data to a remote application server 150 for processing and analysis.

As embodied herein, the data receiving device 120 can further include sensing hardware 4060 similar to, or expanded from, the sensing hardware 5060 of the analyte sensor 110. In particular embodiments, the data receiving device 120 can be configured to operate in coordination with the analyte sensor 110 and based on analyte data received from the analyte sensor 110. As an example, where the analyte sensor 110 glucose sensor, the data receiving device 120 can be or include an insulin pump or insulin injection pen. In coordination, the compatible device 130 can adjust an insulin dosage for a user based on glucose values received from the analyte sensor.

D. Exemplary Sensor Control Devices

Figure 2C:
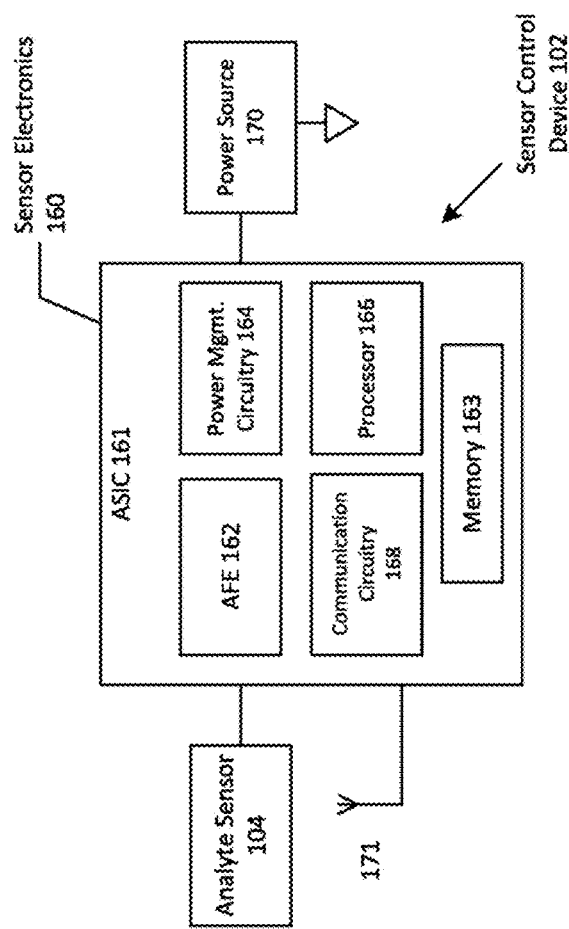
FIGS. 2C and 2D are block diagrams depicting example embodiments of sensor control devices.
Figure 2D:
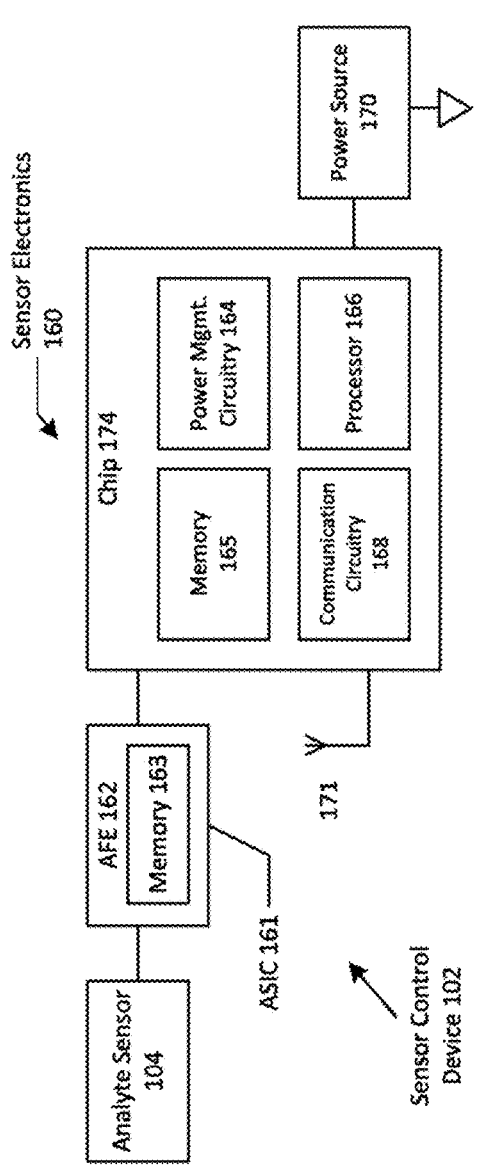

FIGS. 2C and 2D are block diagrams depicting example embodiments of sensor control device 102 having analyte sensor 104 and sensor electronics 160 (including analyte monitoring circuitry) that can have the majority of the processing capability for rendering end-result data suitable for display to the user. In FIG. 2C, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 170, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data.

FIG. 2D is similar to FIG. 2C but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 includes memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Figure 2E:
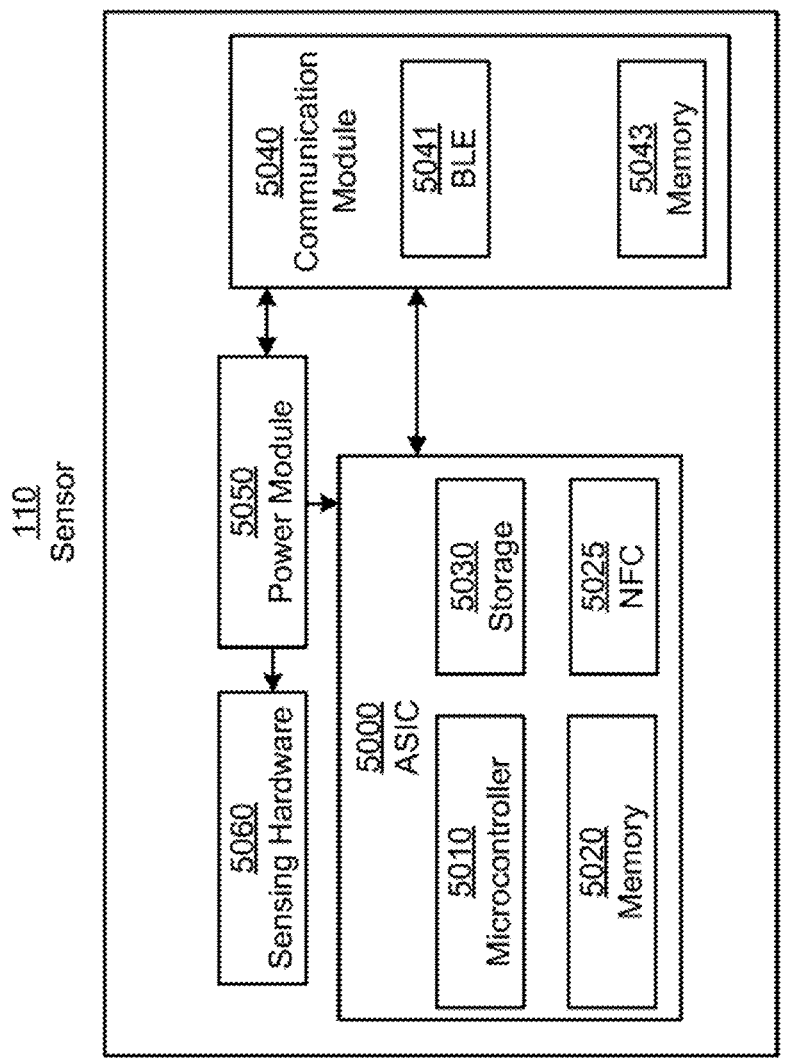
FIG. 2E is a block diagram illustrating an example analyte sensor according to exemplary embodiments of the disclosed subject matter.

For purpose of illustration and not limitation, reference is made to the exemplary embodiment of an analyte sensor 110 for use with the disclosed subject matter as shown in FIG. 2E. FIG. 2E illustrates a block diagram of an example analyte sensor 110 according to exemplary embodiments compatible with the security architecture and communication schemes described herein.

As embodied herein, the analyte sensor 110 can include an Application-Specific Integrated Circuit ("ASIC") 5000 communicatively coupled with a communication module 5040. The ASIC 5000 can include a microcontroller core 5010, on-board memory 5020, and storage memory 5030. The storage memory 5030 can store data used in an authentication and encryption security architecture. The storage memory 5030 can store programming instructions for the sensor 110. As embodied herein, certain communication chipsets can be embedded in the ASIC 5000 (e.g., an NFC transceiver 5025). The ASIC 5000 can receive power from a power module 5050, such as an on-board battery or from an NFC pulse. The storage memory 5030 of the ASIC 5000 can be programmed to include information such as an identifier for the sensor 110 for identification and tracking purposes. The storage memory 5030 can also be programmed with configuration or calibration parameters for use by the sensor 110 and its various components. The storage memory 5030 can include rewritable or one-time programming (OTP) memory. The storage memory 5030 can be updated using techniques described herein to extend the usefulness of the sensor 110.

As embodied herein, the communication module 5040 of the sensor 100 can be or include one or more modules to support the analyte sensor 110 communicating with other devices of the analyte monitoring system 100. As an example only and not by way of limitation, example communication modules 5040 can include a Bluetooth Low-Energy ("BLE") module 5041 As used throughout this disclosure, Bluetooth Low Energy ("BLE") refers to a short-range communication protocol optimized to make pairing of Bluetooth devices simple for end users. The communication module 5040 can transmit and receive data and commands via interaction with similarly-capable communication modules of a data receiving device 120 or user device 140. The communication module 5040 can include additional or alternative chipsets for use with similar short-range communication schemes, such as a personal area network according to IEEE 802.15 protocols, IEEE 802.11 protocols, infrared communications according to the Infrared Data Association standards (IrDA), etc.

To perform its functionalities, the sensor 100 can further include suitable sensing hardware 5060 appropriate to its function. As embodied herein, the sensing hardware 5060 can include an analyte sensor transcutaneously or subcutaneously positioned in contact with a bodily fluid of a subject. The analyte sensor can generate sensor data containing values corresponding to levels of one or more analytes within the bodily fluid.

E. Exemplary Assembly Processes for Sensor Control Devices

The components of sensor control device 102 can be acquired by a user in multiple packages requiring final assembly by the user before delivery to an appropriate user location. FIGS. 3A-3D depict an example embodiment of an assembly process for sensor control device 102 by a user, including preparation of separate components before coupling the components in order to ready the sensor for delivery. FIGS. 3E-3F depict an example embodiment of delivery of sensor control device 102 to an appropriate user location by selecting the appropriate delivery location and applying device 102 to the location.

Figure 3A:
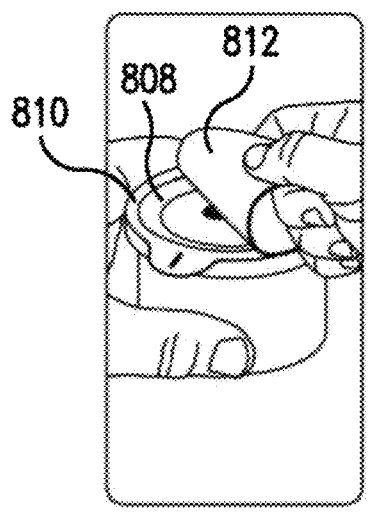
FIG. 3A is a proximal perspective view depicting an example embodiment of a user preparing a tray for an assembly.

FIG. 3A is a proximal perspective view depicting an example embodiment of a user preparing a container 810, configured here as a tray (although other packages can be used), for an assembly process. The user can accomplish this preparation by removing lid 812 from tray 810 to expose platform 808, for instance by peeling a non-adhered portion of lid 812 away from tray 810 such that adhered portions of lid 812 are removed. Removal of lid 812 can be appropriate in various embodiments so long as platform 808 is adequately exposed within tray 810. Lid 812 can then be placed aside.

Figure 3B:
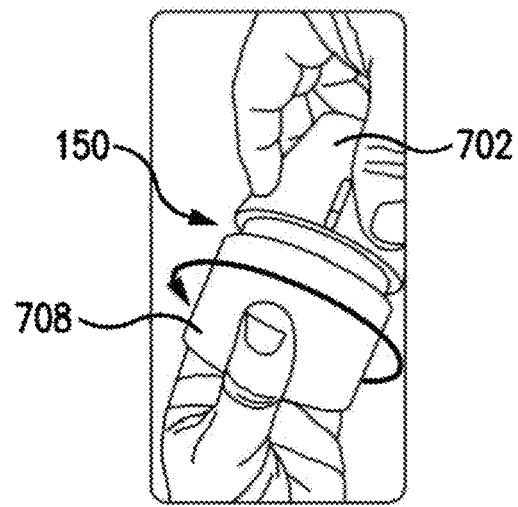
FIG. 3B is a side view depicting an example embodiment of a user preparing an applicator device for an assembly.
Figure 3C:
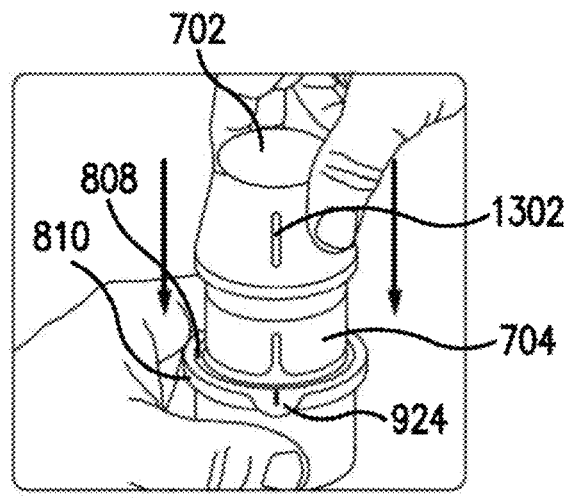
FIG. 3C is a proximal perspective view depicting an example embodiment of a user inserting an applicator device into a tray during an assembly.

FIG. 3B is a side view depicting an example embodiment of a user preparing an applicator device 150 for assembly. Applicator device 150 can be provided in a sterile package sealed by a cap 708. Preparation of applicator device 150 can include uncoupling housing 702 from cap 708 to expose sheath 704 (FIG. 3C). This can be accomplished by unscrewing (or otherwise uncoupling) cap 708 from housing 702. Cap 708 can then be placed aside.

FIG. 3C is a proximal perspective view depicting an example embodiment of a user inserting an applicator device 150 into a tray 810 during an assembly. Initially, the user can insert sheath 704 into platform 808 inside tray 810 after aligning housing orienting feature 1302 (or slot or recess) and tray orienting feature 924 (an abutment or detent). Inserting sheath 704 into platform 808 temporarily unlocks sheath 704 relative to housing 702 and also temporarily unlocks platform 808 relative to tray 810. At this stage, removal of applicator device 150 from tray 810 will result in the same state prior to initial insertion of applicator device 150 into tray 810 (i.e., the process can be reversed or aborted at this point and then repeated without consequence).

Sheath 704 can maintain position within platform 808 with respect to housing 702 while housing 702 is distally advanced, coupling with platform 808 to distally advance platform 808 with respect to tray 810. This step unlocks and collapses platform 808 within tray 810. Sheath 704 can contact and disengage locking features (not shown) within tray 810 that unlock sheath 704 with respect to housing 702 and prevent sheath 704 from moving (relatively) while housing 702 continues to distally advance platform 808. At the end of advancement of housing 702 and platform 808, sheath 704 is permanently unlocked relative to housing 702. A sharp and sensor (not shown) within tray 810 can be coupled with an electronics housing (not shown) within housing 702 at the end of the distal advancement of housing 702. Operation and interaction of the applicator device 150 and tray 810 are further described below.

Figure 3D:
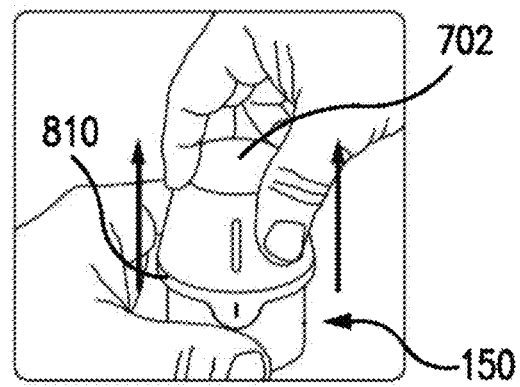
FIG. 3D is a proximal perspective view depicting an example embodiment of a user removing an applicator device from a tray during an assembly.
Figure 3E:
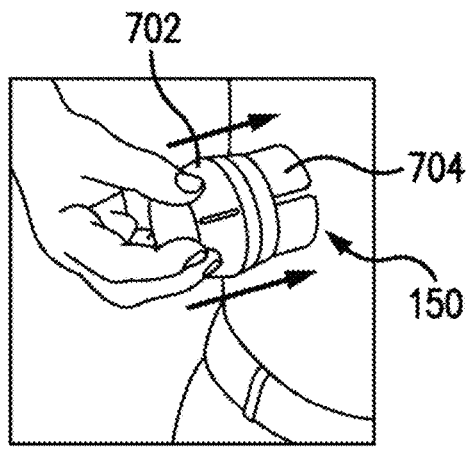
FIG. 3E is a proximal perspective view depicting an example embodiment of a patient applying a sensor using an applicator device.
Figure 3F:
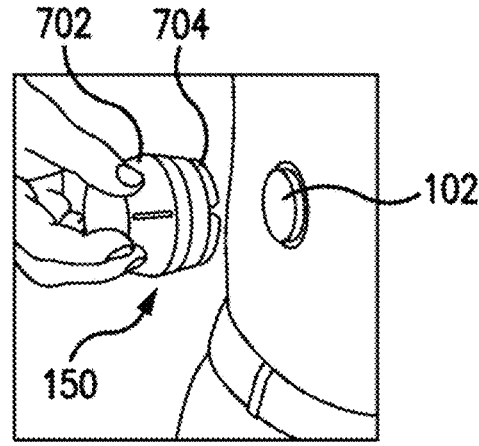
FIG. 3F is a proximal perspective view depicting an example embodiment of a patient with an applied sensor and a used applicator device.

FIG. 3D is a proximal perspective view depicting an example embodiment of a user removing an applicator device 150 from a tray 810 during an assembly. A user can remove applicator 150 from tray 810 by proximally advancing housing 702 with respect to tray 810 or other motions having the same end effect of uncoupling applicator 150 and tray 810. The applicator device 150 is removed with sensor control device 102 (not shown) fully assembled (sharp, sensor, electronics) therein and positioned for delivery.

FIG. 3E is a proximal perspective view depicting an example embodiment of a patient applying sensor control device 102 using applicator device 150 to a target area of skin, for instance, on an abdomen or other appropriate location. Advancing housing 702 distally collapses sheath 704 within housing 702 and applies the sensor to the target location such that an adhesive layer on the bottom side of sensor control device 102 adheres to the skin. The sharp is automatically retracted when housing 702 is fully advanced, while the sensor (not shown) is left in position to measure analyte levels.

FIG. 3F is a proximal perspective view depicting an example embodiment of a patient with sensor control device 102 in an applied position. The user can then remove applicator 150 from the application site.

System 100, described with respect to FIGS. 3A-3F and elsewhere herein, can provide a reduced or eliminated chance of accidental breakage, permanent deformation, or incorrect assembly of applicator components compared to prior art systems. Since applicator housing 702 directly engages platform 808 while sheath 704 unlocks, rather than indirect engagement via sheath 704, relative angularity between sheath 704 and housing 702 will not result in breakage or permanent deformation of the arms or other components. The potential for relatively high forces (such as in conventional devices) during assembly will be reduced, which in turn reduces the chance of unsuccessful user assembly.

F. Exemplary Sensor Applicator Devices

Figure 4C:
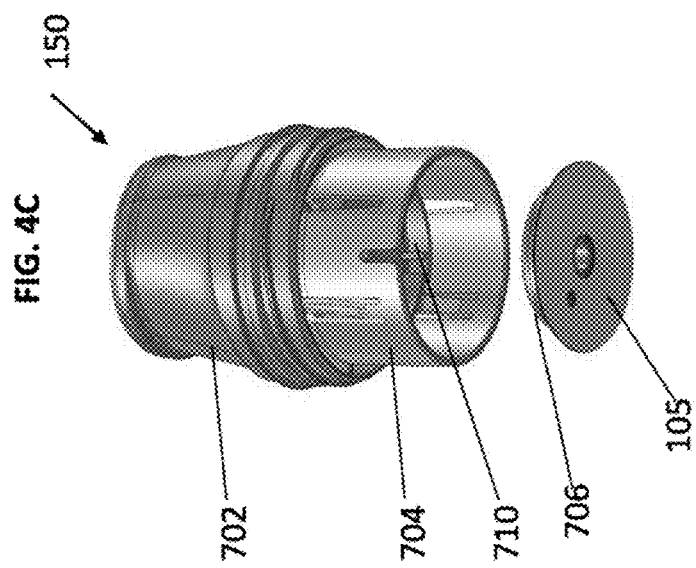
FIG. 4C is a perspective view depicting an example embodiment of a distal end of an applicator device and electronics housing.
Figure 4B:
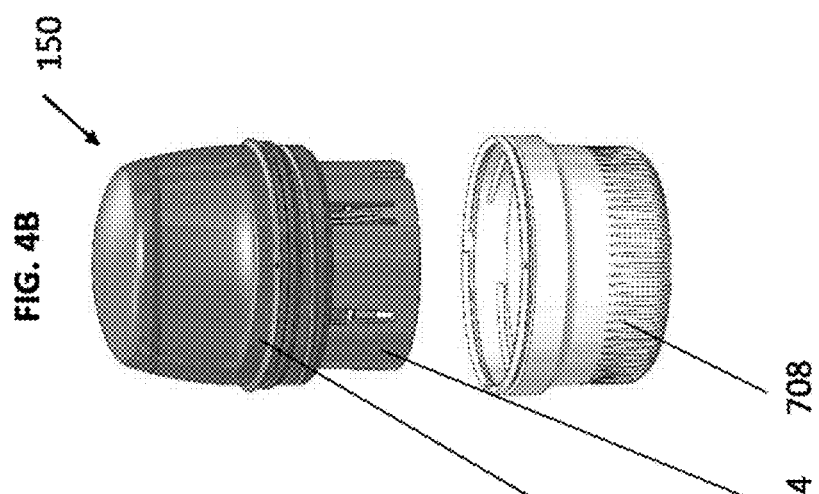
FIG. 4B is a side perspective view depicting an example embodiment of an applicator device and cap decoupled.
Figure 4A:
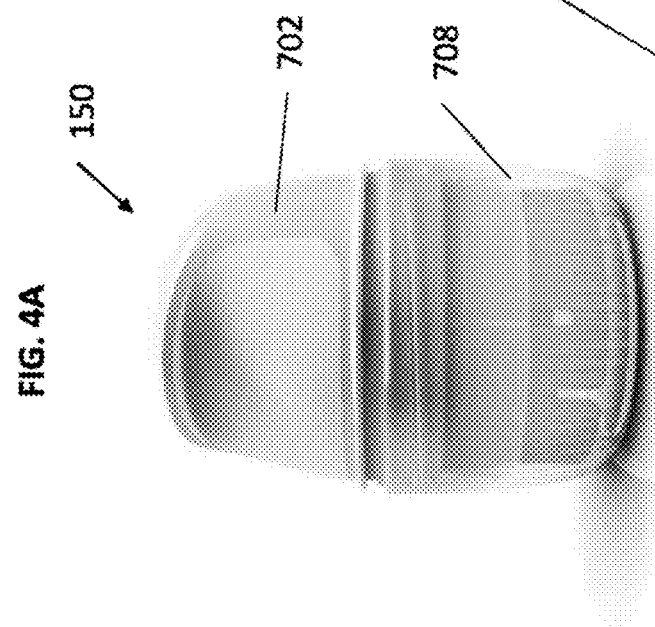
FIG. 4A is a side view depicting an example embodiment of an applicator device coupled with a cap.

FIG. 4A is a side view depicting an example embodiment of an applicator device 150 coupled with screw cap 708. This is an example of how applicator 150 is shipped to and received by a user, prior to assembly by the user with a sensor. FIG. 4B is a side perspective view depicting applicator 150 and cap 708 after being decoupled. FIG. 4C is a perspective view depicting an example embodiment of a distal end of an applicator device 150 with electronics housing 706 and adhesive patch 105 removed from the position they would have retained within sensor carrier 710 of sheath 704, when cap 708 is in place.

Figure 4F:
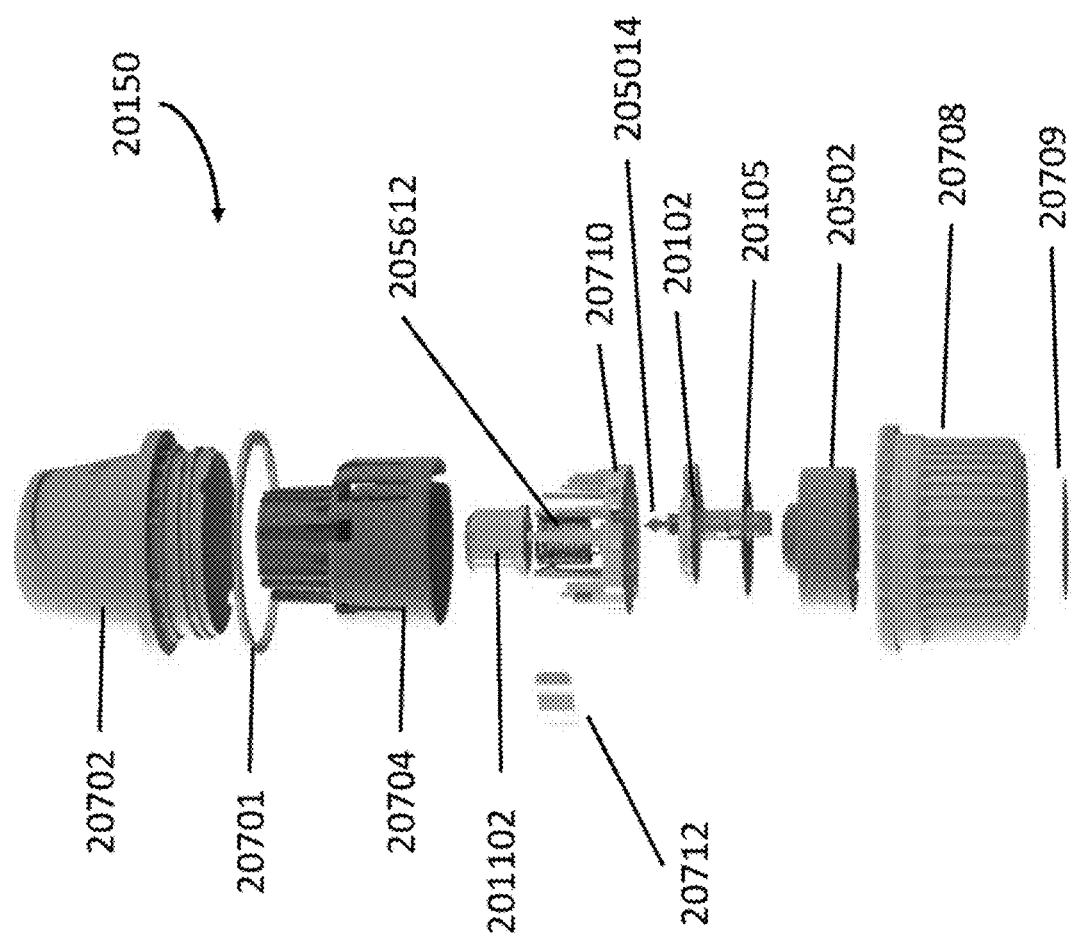
FIG. 4F is an exploded view of the applicator device of FIG. 4D.

Referring to FIG. 4D-G for purpose of illustration and not limitation, the applicator device 20150 can be provided to a user as a single integrated assembly. FIGS. 4D and 4E provide perspective top and bottom views, respectively, of the applicator device 20150, FIG. 4F provides an exploded view of the applicator device 20150 and FIG. 4G provides a side cut-away view. The perspective views illustrate how applicator 20150 is shipped to and received by a user. The exploded and cut-away views illustrate the components of the applicator device 20150. The applicator device 20150 can include a housing 20702, gasket 20701, sheath 20704, sharp carrier 201102, spring 205612, sensor carrier 20710 (also referred to as a "puck carrier"), sharp hub 205014, sensor control device (also referred to as a "puck") 20102, adhesive patch 20105, desiccant 20502, cap 20708, serial label 20709, and tamper evidence feature 20712. As received by a user, only the housing 20702, cap 20708, tamper evidence feature 20712, and label 20709 are visible. The tamper evidence feature 20712 can be, for example, a sticker coupled to each of the housing 20702 and the cap 20708, and tamper evidence feature 20712 can be damaged, for example, irreparably, by uncoupling housing 20702 and cap 20708, thereby indicating to a user that the housing 20702 and cap 20708 have been previously uncoupled. These features are described in greater detail below.

G. Exemplary Tray and Sensor Module Assembly

Figure 5:
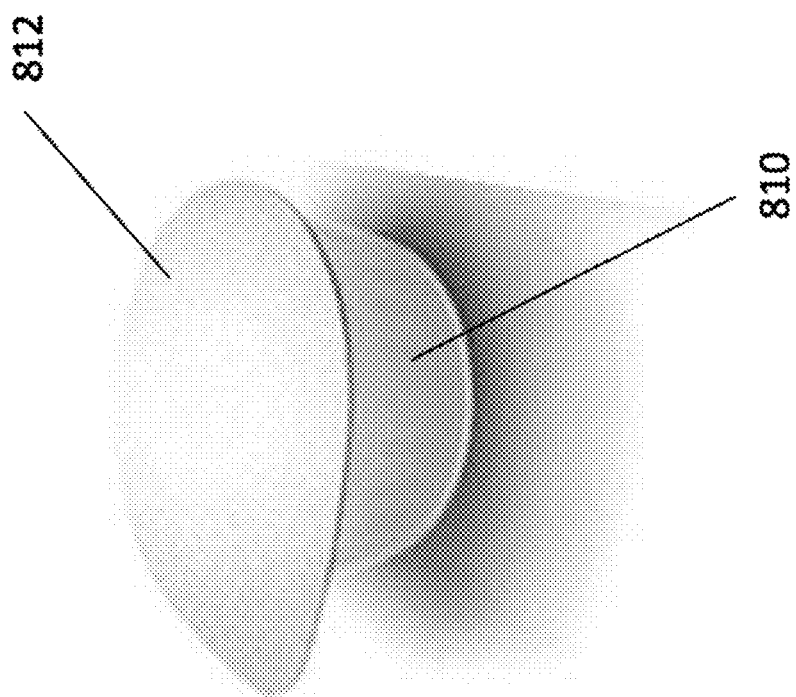
FIG. 5 is a proximal perspective view depicting an example embodiment of a tray with sterilization lid coupled.

FIG. 5 is a proximal perspective view depicting an example embodiment of a tray 810 with sterilization lid 812 removably coupled thereto, which may be representative of how the package is shipped to and received by a user prior to assembly.

Figure 6A:
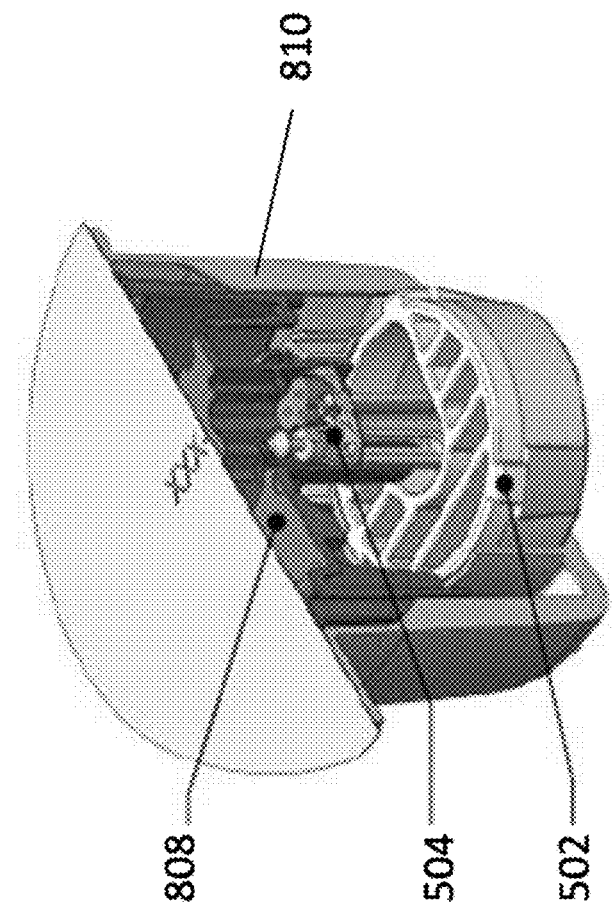
FIG. 6A is a proximal perspective cutaway view depicting an example embodiment of a tray with sensor delivery components.

FIG. 6A is a proximal perspective cutaway view depicting sensor delivery components within tray 810. Platform 808 is slidably coupled within tray 810. Desiccant 502 is stationary with respect to tray 810. Sensor module 504 is mounted within tray 810.

Figure 6B:
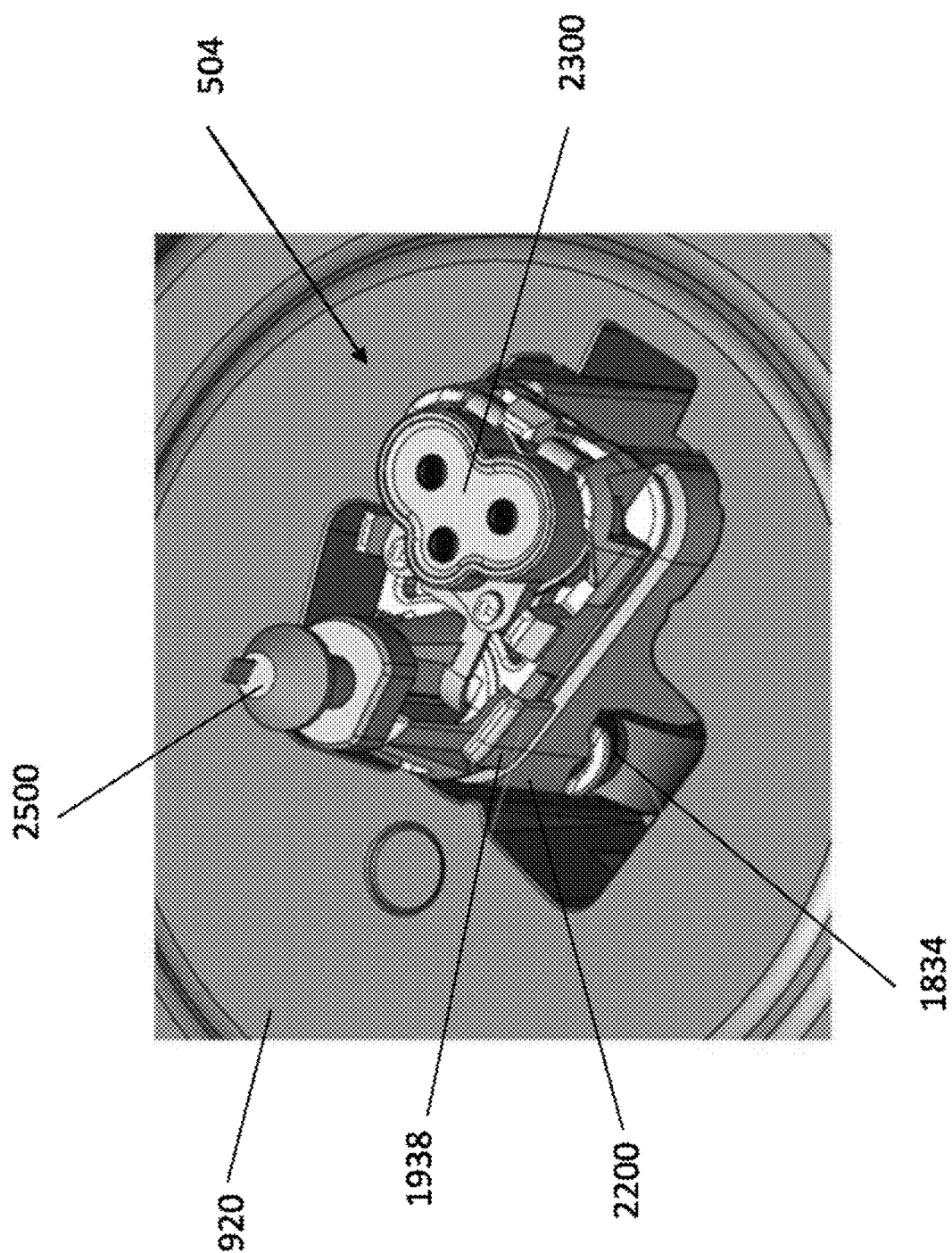
FIG. 6B is a proximal perspective view depicting sensor delivery components.

FIG. 6B is a proximal perspective view depicting sensor module 504 in greater detail. Here, retention arm extensions 1834 of platform 808 releasably secure sensor module 504 in position. Module 2200 is coupled with connector 2300, sharp module 2500 and sensor (not shown) such that during assembly they can be removed together as sensor module 504.

H. Exemplary Applicators and Sensor Control Devices for One Piece Architectures

Referring briefly again to FIGS. 1A and 3A-3F, for the two-piece architecture system, the sensor tray 202 and the sensor applicator 102 are provided to the user as separate packages, thus requiring the user to open each package and finally assemble the system. In some applications, the discrete, sealed packages allow the sensor tray 202 and the sensor applicator 102 to be sterilized in separate sterilization processes unique to the contents of each package and otherwise incompatible with the contents of the other. More specifically, the sensor tray 202, which includes the plug assembly 207, including the sensor 110 and the sharp 220, may be sterilized using radiation sterilization, such as electron beam (or "e-beam") irradiation. Suitable radiation sterilization processes include, but are not limited to, electron beam (e-beam) irradiation, gamma ray irradiation, X-ray irradiation, or any combination thereof. Radiation sterilization, however, can damage the electrical components arranged within the electronics housing of the sensor control device 102. Consequently, if the sensor applicator 102, which contains the electronics housing of the sensor control device 102, needs to be sterilized, it may be sterilized via another method, such as gaseous chemical sterilization using, for example, ethylene oxide. Gaseous chemical sterilization, however, can damage the enzymes or other chemistry and biologics included on the sensor 110. Because of this sterilization incompatibility, the sensor tray 202 and the sensor applicator 102 are commonly sterilized in separate sterilization processes and subsequently packaged separately, which requires the user to finally assemble the components for use.

Figure 7A:
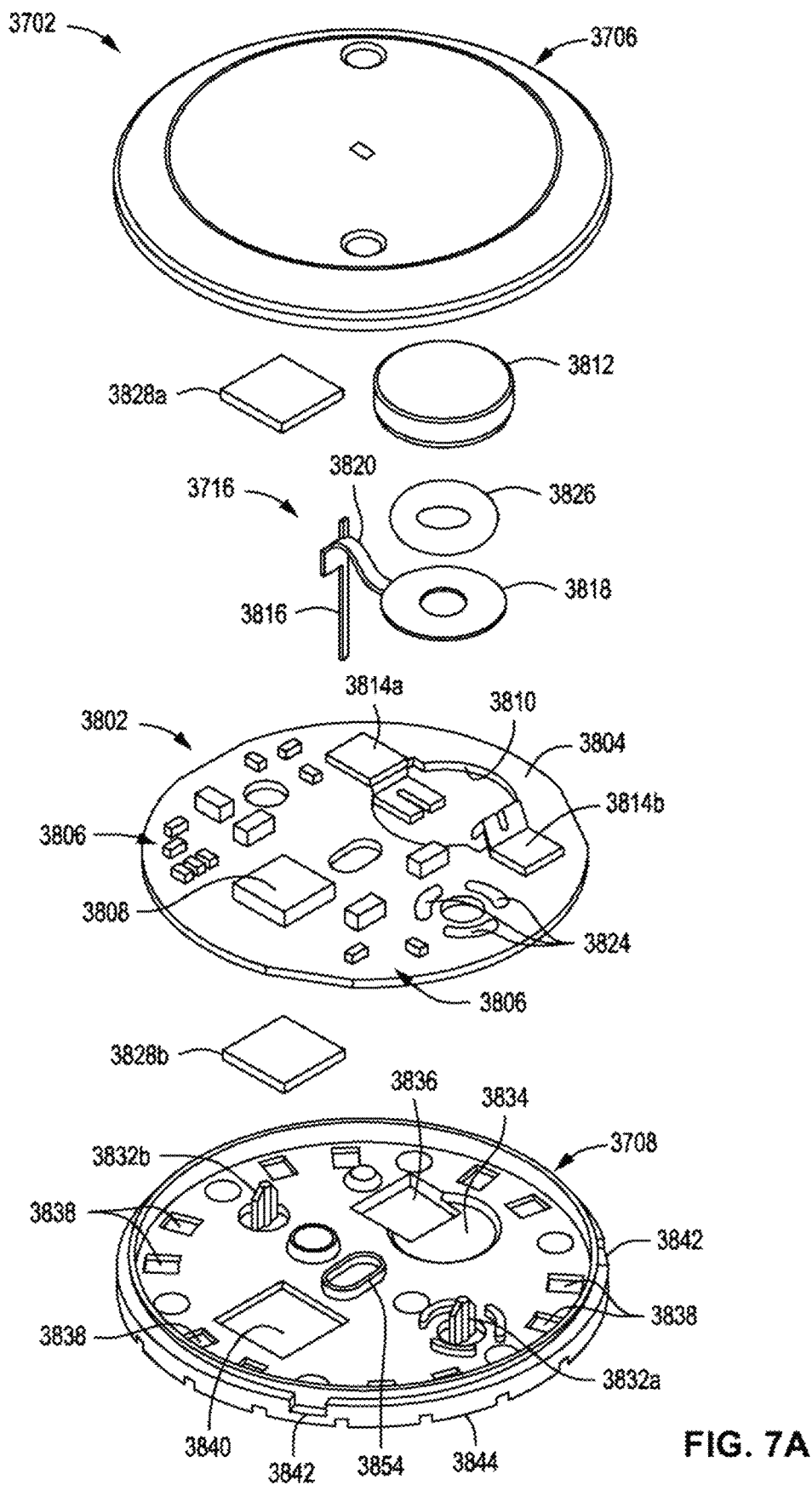
FIGS. 7A and 7B are isometric exploded top and bottom views, respectively, of an exemplary sensor control device.
Figure 7B:
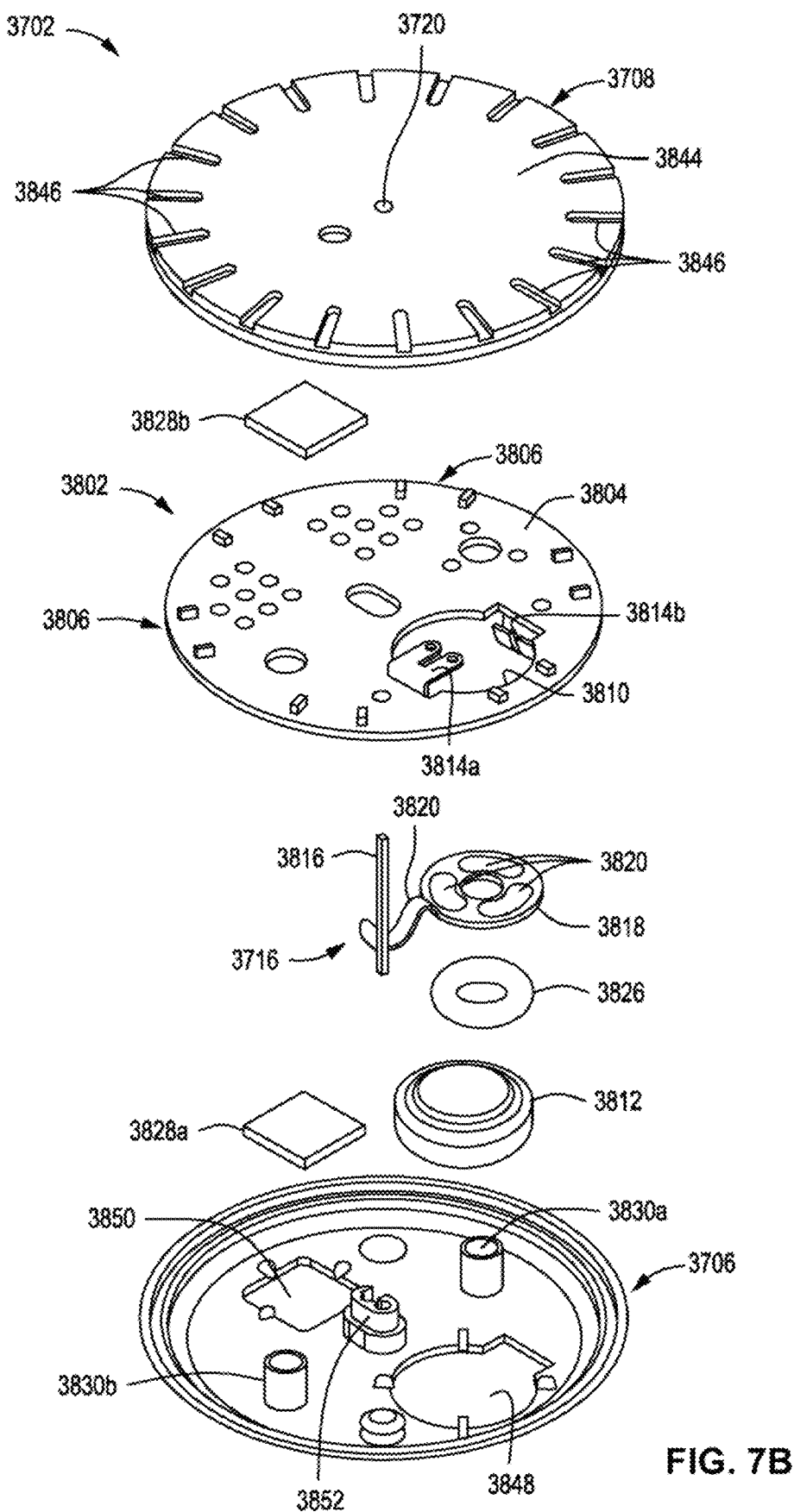

FIGS. 7A and 7B are exploded top and bottom views, respectively, of the sensor control device 3702, according to one or more embodiments. The shell 3706 and the mount 3708 operate as opposing clamshell halves that enclose or otherwise substantially encapsulate the various electronic components of the sensor control device 3702. As illustrated, the sensor control device 3702 may include a printed circuit board assembly (PCBA) 3802 that includes a printed circuit board (PCB) 3804 having a plurality of electronic modules 3806 coupled thereto. Example electronic modules 3806 include, but are not limited to, resistors, transistors, capacitors, inductors, diodes, and switches. Prior sensor control devices commonly stack PCB components on only one side of the PCB. In contrast, the PCB components 3806 in the sensor control device 3702 can be dispersed about the surface area of both sides (i.e., top and bottom surfaces) of the PCB 3804.

Besides the electronic modules 3806, the PCBA 3802 may also include a data processing unit 3808 mounted to the PCB 3804. The data processing unit 3808 may comprise, for example, an application specific integrated circuit (ASIC) configured to implement one or more functions or routines associated with operation of the sensor control device 3702. More specifically, the data processing unit 3808 may be configured to perform data processing functions, where such functions may include but are not limited to, filtering and encoding of data signals, each of which corresponds to a sampled analyte level of the user. The data processing unit 3808 may also include or otherwise communicate with an antenna for communicating with the reader device 106 (FIG. 1A).

A battery aperture 3810 may be defined in the PCB 3804 and sized to receive and seat a battery 3812 configured to power the sensor control device 3702. An axial battery contact 3814*a* and a radial battery contact 3814*b* may be coupled to the PCB 3804 and extend into the battery aperture 3810 to facilitate transmission of electrical power from the battery 3812 to the PCB 3804. As their names suggest, the axial battery contact 3814*a* may be configured to provide an axial contact for the battery 3812, while the radial battery contact 3814*b* may provide a radial contact for the battery 3812. Locating the battery 3812 within the battery aperture 3810 with the battery contacts 3814*a,b* helps reduce the height H of the sensor control device 3702, which allows the PCB 3804 to be located centrally and its components to be dispersed on both sides (i.e., top and bottom surfaces). This also helps facilitate the chamfer 3718 provided on the electronics housing 3704.

The sensor 3716 may be centrally located relative to the PCB 3804 and include a tail 3816, a flag 3818, and a neck 3820 that interconnects the tail 3816 and the flag 3818. The tail 3816 may be configured to extend through the central aperture 3720 of the mount 3708 to be transcutaneously received beneath a user's skin. Moreover, the tail 3816 may have an enzyme or other chemistry included thereon to help facilitate analyte monitoring.

The flag 3818 may include a generally planar surface having one or more sensor contacts 3822 (three shown in FIG. 7B) arranged thereon. The sensor contact(s) 3822 may be configured to align with and engage a corresponding one or more circuitry contacts 3824 (three shown in FIG. 7A) provided on the PCB 3804. In some embodiments, the sensor contact(s) 3822 may comprise a carbon impregnated polymer printed or otherwise digitally applied to the flag 3818. Prior sensor control devices typically include a connector made of silicone rubber that encapsulates one or more compliant carbon impregnated polymer modules that serve as electrical conductive contacts between the sensor and the PCB. In contrast, the presently disclosed sensor contacts(s) 3822 provide a direct connection between the sensor 3716 and the PCB 3804 connection, which eliminates the need for the prior art connector and advantageously reduces the height H. Moreover, eliminating the compliant carbon impregnated polymer modules eliminates a significant circuit resistance and therefor improves circuit conductivity.

The sensor control device 3702 may further include a compliant member 3826, which may be arranged to interpose the flag 3818 and the inner surface of the shell 3706. More specifically, when the shell 3706 and the mount 3708 are assembled to one another, the compliant member 3826 may be configured to provide a passive biasing load against the flag 3818 that forces the sensor contact(s) 3822 into continuous engagement with the corresponding circuitry contact(s) 3824. In the illustrated embodiment, the compliant member 3826 is an elastomeric O-ring, but could alternatively comprise any other type of biasing device or mechanism, such as a compression spring or the like, without departing from the scope of the disclosure.

The sensor control device 3702 may further include one or more electromagnetic shields, shown as a first shield 3828*a* and a second shield The shell 3706 may provide or otherwise define a first clocking receptacle 3830*a* (FIG. 7B) and a second clocking receptacle 3830*b* (FIG. 7B), and the mount 3708 may provide or otherwise define a first clocking post 3832*a* (FIG. 7A) and a second clocking post 3832*b* (FIG. 7A). Mating the first and second clocking receptacles 3830a,b with the first and second clocking posts 3832a,b, respectively, will properly align the shell 3706 to the mount 3708.

Referring specifically to FIG. 7A, the inner surface of the mount 3708 may provide or otherwise define a plurality of pockets or depressions configured to accommodate various component parts of the sensor control device 3702 when the shell 3706 is mated to the mount 3708. For example, the inner surface of the mount 3708 may define a battery locator 3834 configured to accommodate a portion of the battery 3812 when the sensor control device 3702 is assembled. An adjacent contact pocket 3836 may be configured to accommodate a portion of the axial contact 3814a.

Moreover, a plurality of module pockets 3838 may be defined in the inner surface of the mount 3708 to accommodate the various electronic modules 3806 arranged on the bottom of the PCB 3804. Furthermore, a shield locator 3840 may be defined in the inner surface of the mount 3708 to accommodate at least a portion of the second shield 3828b when the sensor control device 3702 is assembled. The battery locator 3834, the contact pocket 3836, the module pockets 3838, and the shield locator 3840 all extend a short distance into the inner surface of the mount 3708 and, as a result, the overall height H of the sensor control device 3702 may be reduced as compared to prior sensor control devices. The module pockets 3838 may also help minimize the diameter of the PCB 3804 by allowing PCB components to be arranged on both sides (i.e., top and bottom surfaces).

Still referring to FIG. 7A, the mount 3708 may further include a plurality of carrier grip features 3842 (two shown) defined about the outer periphery of the mount 3708. The carrier grip features 3842 are axially offset from the bottom 3844 of the mount 3708, where a transfer adhesive (not shown) may be applied during assembly. In contrast to prior sensor control devices, which commonly include conical carrier grip features that intersect with the bottom of the mount, the presently disclosed carrier grip features 3842 are offset from the plane (i.e., the bottom 3844) where the transfer adhesive is applied. This may prove advantageous in helping ensure that the delivery system does not inadvertently stick to the transfer adhesive during assembly. Moreover, the presently disclosed carrier grip features 3842 eliminate the need for a scalloped transfer adhesive, which simplifies the manufacture of the transfer adhesive and eliminates the need to accurately clock the transfer adhesive relative to the mount 3708. This also increases the bond area and, therefore, the bond strength.

Referring to FIG. 7B, the bottom 3844 of the mount 3708 may provide or otherwise define a plurality of grooves 3846, which may be defined at or near the outer periphery of the mount 3708 and equidistantly spaced from each other. A transfer adhesive (not shown) may be coupled to the bottom 3844 and the grooves 3846 may be configured to help convey (transfer) moisture away from the sensor control device 3702 and toward the periphery of the mount 3708 during use. In some embodiments, the spacing of the grooves 3846 may interpose the module pockets 3838 (FIG. 7A) defined on the opposing side (inner surface) of the mount 3708. As will be appreciated, alternating the position of the grooves 3846 and the module pockets 3838 ensures that the opposing features on either side of the mount 3708 do not extend into each other. This may help maximize usage of the material for the mount 3708 and thereby help maintain a minimal height H of the sensor control device 3702. The module pockets 3838 may also significantly reduce mold sink, and improve the flatness of the bottom 3844 that the transfer adhesive bonds to.

Still referring to FIG. 7B, the inner surface of the shell 3706 may also provide or otherwise define a plurality of pockets or depressions configured to accommodate various component parts of the sensor control device 3702 when the shell 3706 is mated to the mount 3708. For example, the inner surface of the shell 3706 may define an opposing battery locator 3848 arrangeable opposite the battery locator 3834 (FIG. 7A) of the mount 3708 and configured to accommodate a portion of the battery 3812 when the sensor control device 3702 is assembled. The opposing battery locator 3848 extends a short distance into the inner surface of the shell 3706, which helps reduce the overall height H of the sensor control device 3702.

A sharp and sensor locator 3852 may also be provided by or otherwise defined on the inner surface of the shell 3706. The sharp and sensor locator 3852 may be configured to receive both the sharp (not shown) and a portion of the sensor 3716. Moreover, the sharp and sensor locator 3852 may be configured to align and/or mate with a corresponding sharp and sensor locator 2054 (FIG. 7A) provided on the inner surface of the mount 3708.

Figure 8A:
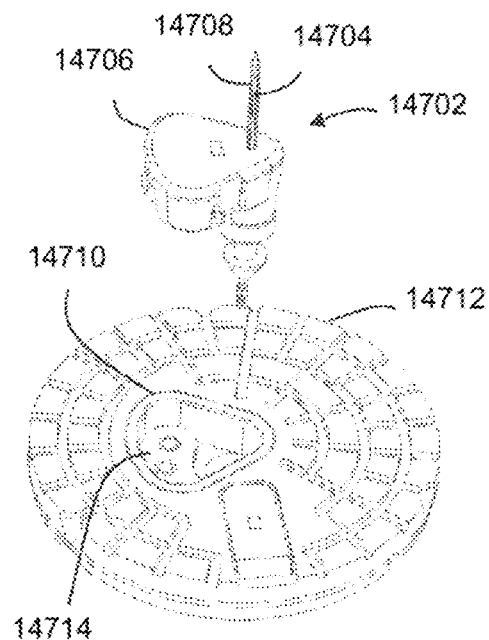
FIG. 8A-8C are assembly and cross-sectional views of an on-body device including an integrated connector for the sensor assembly.
Figure 8B:
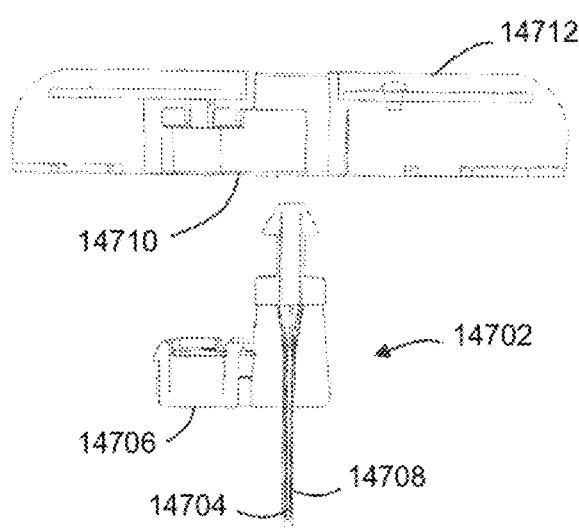
Figure 8C:
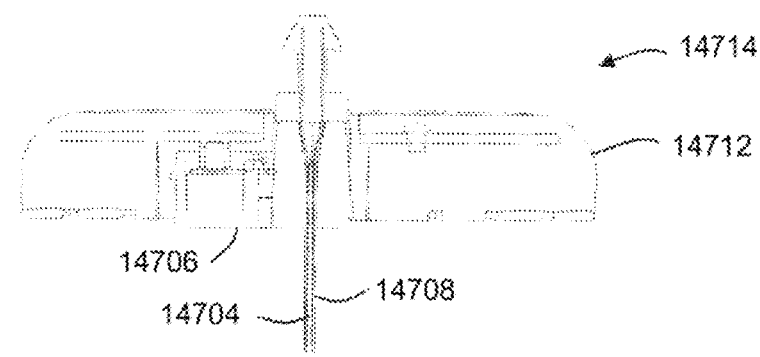

According to embodiments of the present disclosure, an alternative sensor assembly/electronics assembly connection approach is illustrated in FIGS. 8A to 8C. As shown, the sensor assembly 14702 includes sensor 14704, connector support 14706, and sharp 14708. Notably, a recess or receptacle 14710 may be defined in the bottom of the mount of the electronics assembly 14712 and provide a location where the sensor assembly 14702 may be received and coupled to the electronics assembly 14712, and thereby fully assemble the sensor control device. The profile of the sensor assembly 14702 may match or be shaped in complementary fashion to the receptacle 14710, which includes an elastomeric sealing member 14714 (including conductive material coupled to the circuit board and aligned with the electrical contacts of the sensor 14704). Thus, when the sensor assembly 14702 is snap fit or otherwise adhered to the electronics assembly 14712 by driving the sensor assembly 14702 into the integrally formed recess 14710 in the electronics assembly 14712, the on-body device 14714 depicted in FIG. 8C is formed. This embodiment provides an integrated connector for the sensor assembly 14702 within the electronics assembly 14712.

Additional information regarding sensor assemblies is provided in U.S. Publication No. 2013/0150691 and U.S. Publication No. 2021/0204841, each of which is incorporated by reference herein in its entirety.

According to embodiments of the present disclosure, the sensor control device 102 may be modified to provide a one-piece architecture that may be subjected to sterilization techniques specifically designed for a one-piece architecture sensor control device. A one-piece architecture allows the sensor applicator 150 and the sensor control device 102 to be shipped to the user in a single, sealed package that does not require any final user assembly steps. Rather, the user need only open one package and subsequently deliver the sensor control device 102 to the target monitoring location. The one-piece system architecture described herein may prove advantageous in eliminating component parts, various fabrication process steps, and user assembly steps. As a result, packaging and waste are reduced, and the potential for user error or contamination to the system is mitigated.

Figure 9B:
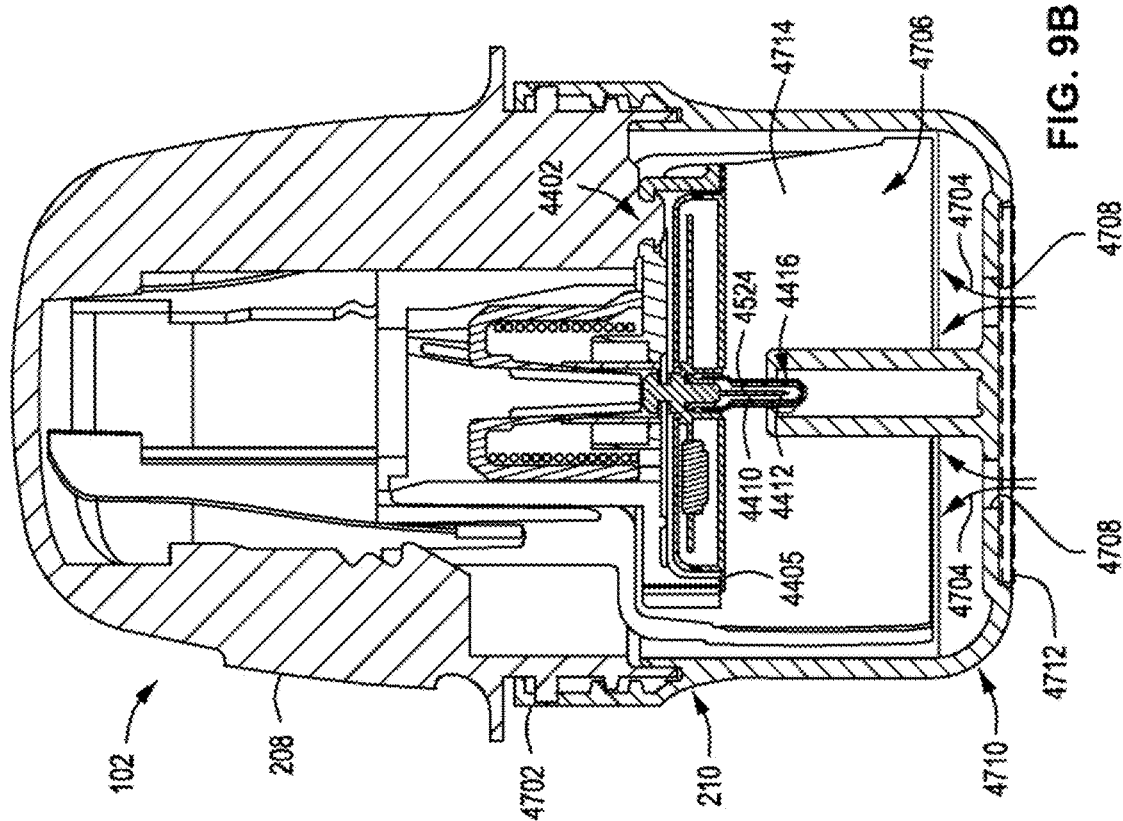
FIGS. 9A and 9B are side and cross-sectional side views, respectively, of an example embodiment of the sensor applicator of FIG. 1A with the cap of FIG. 2C coupled thereto.
Figure 9A:
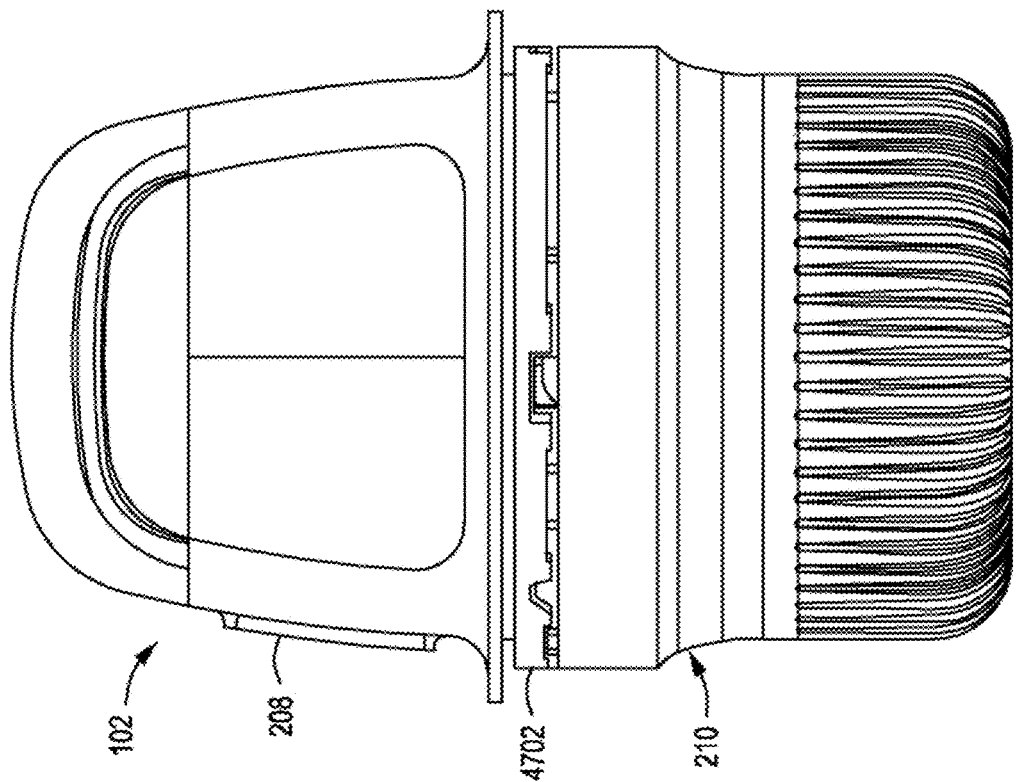

FIGS. 9A and 9B are side and cross-sectional side views, respectively, of an example embodiment of the sensor applicator 102 with the applicator cap 210 coupled thereto. More specifically, FIG. 9A depicts how the sensor applicator 102 might be shipped to and received by a user, and FIG. 9B depicts the sensor control device 4402 arranged within the sensor applicator 102. Accordingly, the fully assembled sensor control device 4402 may already be assembled and installed within the sensor applicator 102 prior to being delivered to the user, thus removing any additional assembly steps that a user would otherwise have to perform.

The fully assembled sensor control device 4402 may be loaded into the sensor applicator 102, and the applicator cap 210 may subsequently be coupled to the sensor applicator 102. In some embodiments, the applicator cap 210 may be threaded to the housing 208 and include a tamper ring 4702. Upon rotating (e.g., unscrewing) the applicator cap 210 relative to the housing 208, the tamper ring 4702 may shear and thereby free the applicator cap 210 from the sensor applicator 102.

According to the present disclosure, while loaded in the sensor applicator 102, the sensor control device 4402 may be subjected to gaseous chemical sterilization 4704 configured to sterilize the electronics housing 4404 and any other exposed portions of the sensor control device 4402. To accomplish this, a chemical may be injected into a sterilization chamber 4706 cooperatively defined by the sensor applicator 102 and the interconnected cap 210. In some applications, the chemical may be injected into the sterilization chamber 4706 via one or more vents 4708 defined in the applicator cap 210 at its proximal end 610. Example chemicals that may be used for the gaseous chemical sterilization 4704 include, but are not limited to, ethylene oxide, vaporized hydrogen peroxide, nitrogen oxide (e.g., nitrous oxide, nitrogen dioxide, etc.), and steam.

Since the distal portions of the sensor 4410 and the sharp 4412 are sealed within the sensor cap 4416, the chemicals used during the gaseous chemical sterilization process do not interact with the enzymes, chemistry, and biologics provided on the tail 4524 and other sensor components, such as membrane coatings that regulate analyte influx.

Once a desired sterility assurance level has been achieved within the sterilization chamber 4706, the gaseous solution may be removed and the sterilization chamber 4706 may be aerated. Aeration may be achieved by a series of vacuums and subsequently circulating a gas (e.g., nitrogen) or filtered air through the sterilization chamber 4706. Once the sterilization chamber 4706 is properly aerated, the vents 4708 may be occluded with a seal 4712 (shown in dashed lines).

In some embodiments, the seal 4712 may comprise two or more layers of different materials. The first layer may be made of a synthetic material (e.g., a flash-spun high-density polyethylene fiber), such as Tyvek® available from DuPont. Tyvek® is highly durable and puncture resistant and allows the permeation of vapors. The Tyvek® layer can be applied before the gaseous chemical sterilization process, and following the gaseous chemical sterilization process, a foil or other vapor and moisture resistant material layer may be sealed (e.g., heat sealed) over the Tyvek® layer to prevent the ingress of contaminants and moisture into the sterilization chamber 4706. In other embodiments, the seal 4712 may comprise only a single protective layer applied to the applicator cap 210. In such embodiments, the single layer may be gas permeable for the sterilization process, but may also be capable of protection against moisture and other harmful elements once the sterilization process is complete.

With the seal 4712 in place, the applicator cap 210 provides a barrier against outside contamination, and thereby maintains a sterile environment for the assembled sensor control device 4402 until the user removes (unthreads) the applicator cap 210. The applicator cap 210 may also create a dust-free environment during shipping and storage that prevents the adhesive patch 4714 from becoming dirty.

Figure 10A:
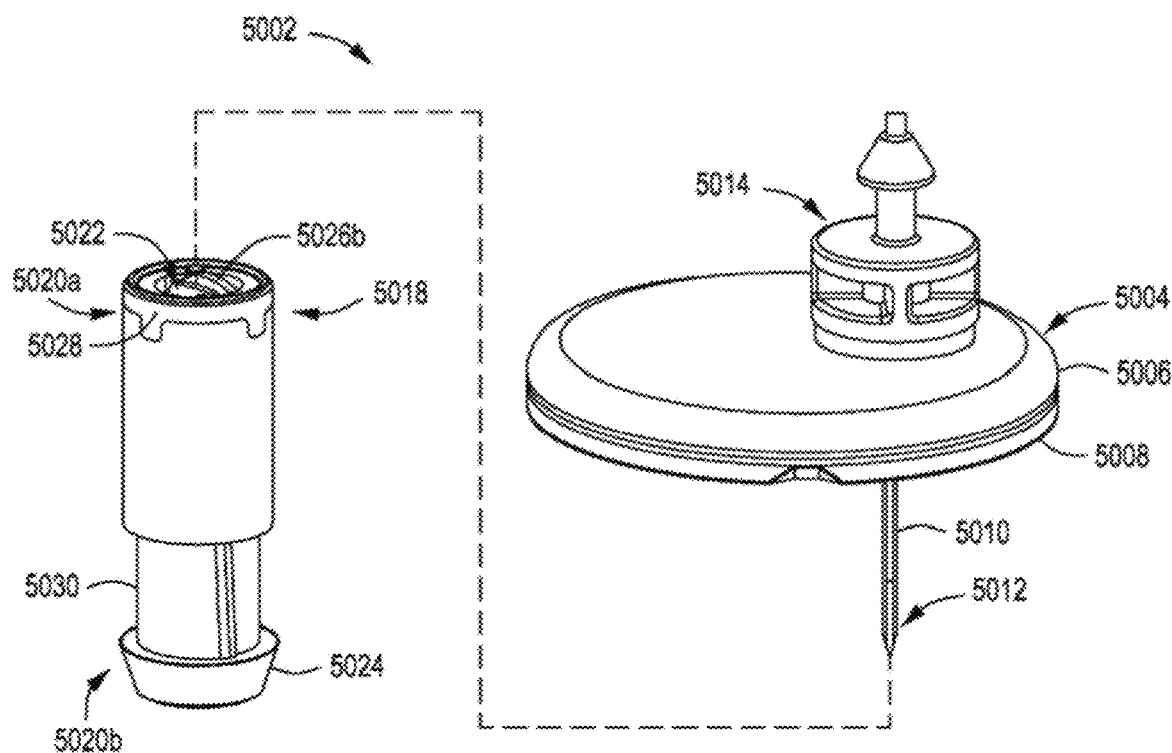
FIGS. 10A and 10B are isometric and side views, respectively, of another example sensor control device.
Figure 10B:
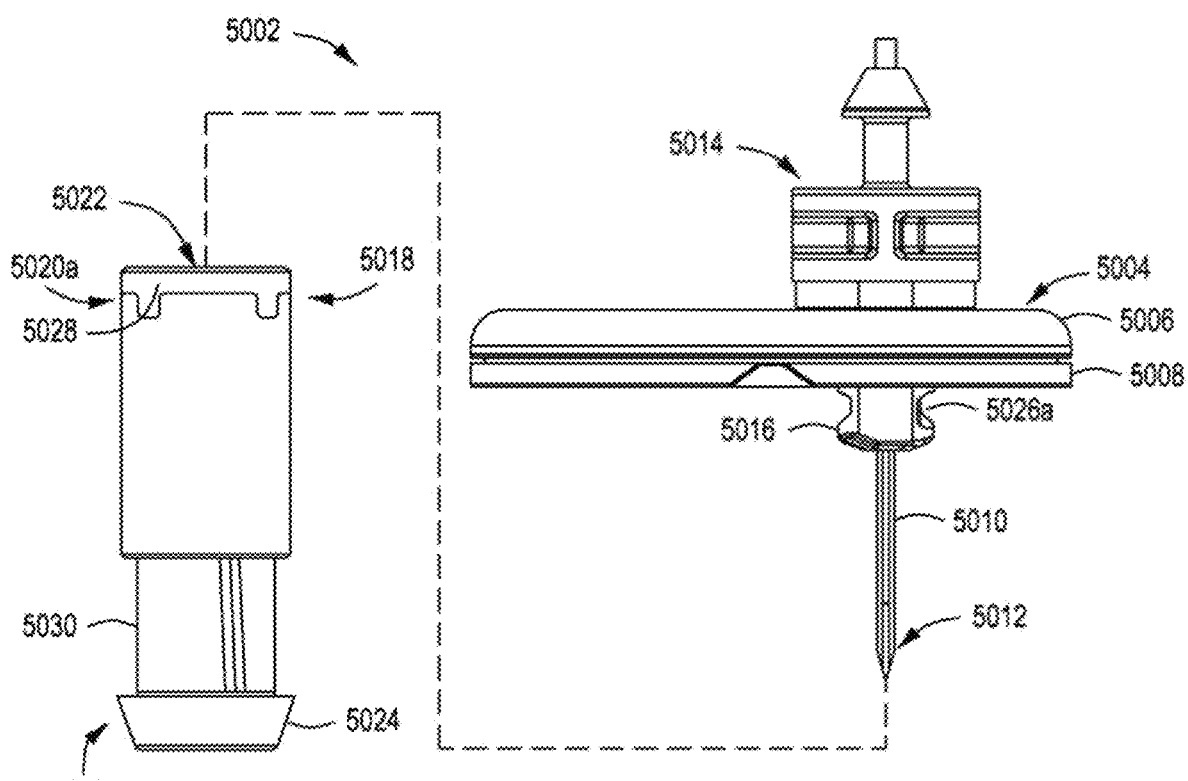

FIGS. 10A and 10B are isometric and side views, respectively, of another example sensor control device 5002, according to one or more embodiments of the present disclosure. The sensor control device 5002 may be similar in some respects to the sensor control device 102 of FIG. 1A and therefore may be best understood with reference thereto. Moreover, the sensor control device 5002 may replace the sensor control device 102 of FIG. 1A and, therefore, may be used in conjunction with the sensor applicator 102 of FIG. 1A, which may deliver the sensor control device 5002 to a target monitoring location on a user's skin.

Unlike the sensor control device 102 of FIG. 1A, however, the sensor control device 5002 may comprise a one-piece system architecture not requiring a user to open multiple packages and finally assemble the sensor control device 5002 prior to application. Rather, upon receipt by the user, the sensor control device 5002 may already be fully assembled and properly positioned within the sensor applicator ISO (FIG. 1A). To use the sensor control device 5002, the user need only open one barrier (e.g., the applicator cap 708 of FIG. 3B) before promptly delivering the sensor control device 5002 to the target monitoring location for use.

As illustrated, the sensor control device 5002 includes an electronics housing 5004 that is generally disc-shaped and may have a circular cross-section. In other embodiments, however, the electronics housing 5004 may exhibit other cross-sectional shapes, such as ovoid or polygonal, without departing from the scope of the disclosure. The electronics housing 5004 may be configured to house or otherwise contain various electrical components used to operate the sensor control device 5002. In at least one embodiment, an adhesive patch (not shown) may be arranged at the bottom of the electronics housing 5004. The adhesive patch may be similar to the adhesive patch 105 of FIG. 1A, and may thus help adhere the sensor control device 5002 to the user's skin for use.

As illustrated, the sensor control device 5002 includes an electronics housing 5004 that includes a shell 5006 and a mount 5008 that is matable with the shell 5006. The shell 5006 may be secured to the mount 5008 via a variety of ways, such as a snap fit engagement, an interference fit, sonic welding, one or more mechanical fasteners (e.g., screws), a gasket, an adhesive, or any combination thereof. In some cases, the shell 5006 may be secured to the mount 5008 such that a sealed interface is generated therebetween.

The sensor control device 5002 may further include a sensor 5010 (partially visible) and a sharp 5012 (partially visible), used to help deliver the sensor 5010 transcutaneously under a user's skin during application of the sensor control device 5002. As illustrated, corresponding portions of the sensor 5010 and the sharp 5012 extend distally from the bottom of the electronics housing 5004 (e.g., the mount 5008). The sharp 5012 may include a sharp hub 5014 configured to secure and carry the sharp 5012. As best seen in FIG. 10B, the sharp hub 5014 may include or otherwise define a mating member 5016. To couple the sharp 5012 to the sensor control device 5002, the sharp 5012 may be advanced axially through the electronics housing 5004 until the sharp hub 5014 engages an upper surface of the shell 5006 and the mating member 5016 extends distally from the bottom of the mount 5008. As the sharp 5012 penetrates the electronics housing 5004, the exposed portion of the sensor 5010 may be received within a hollow or recessed (arcuate)

portion of the sharp 5012. The remaining portion of the sensor 5010 is arranged within the interior of the electronics housing 5004.

The sensor control device 5002 may further include a sensor cap 5018, shown exploded or detached from the electronics housing 5004 in FIGS. 10A-10B. The sensor cap 5016 may be removably coupled to the sensor control device 5002 (e.g., the electronics housing 5004) at or near the bottom of the mount 5008. The sensor cap 5018 may help provide a sealed barrier that surrounds and protects the exposed portions of the sensor 5010 and the sharp 5012 from gaseous chemical sterilization. As illustrated, the sensor cap 5018 may comprise a generally cylindrical body having a first end 5020a and a second end 5020b opposite the first end 5020a. The first end 5020a may be open to provide access into an inner chamber 5022 defined within the body. In contrast, the second end 5020b may be closed and may provide or otherwise define an engagement feature 5024. As described herein, the engagement feature 5024 may help mate the sensor cap 5018 to the cap (e.g., the applicator cap 708 of FIG. 3B) of a sensor applicator (e.g., the sensor applicator 150 of FIGS. 1A and 3A-3F), and may help remove the sensor cap 5018 from the sensor control device 5002 upon removing the cap from the sensor applicator.

The sensor cap 5018 may be removably coupled to the electronics housing 5004 at or near the bottom of the mount 5008. More specifically, the sensor cap 5018 may be removably coupled to the mating member 5016, which extends distally from the bottom of the mount 5008. In at least one embodiment, for example, the mating member 5016 may define a set of external threads 5026a (FIG. 10B) matable with a set of internal threads 5026b (FIG. 10A) defined by the sensor cap 5018. In some embodiments, the external and internal threads 5026a, b may comprise a flat thread design (e.g., lack of helical curvature), which may prove advantageous in molding the parts. Alternatively, the external and internal threads 5026a,b may comprise a helical threaded engagement. Accordingly, the sensor cap 5018 may be threadably coupled to the sensor control device 5002 at the mating member 5016 of the sharp hub 5014. In other embodiments, the sensor cap 5018 may be removably coupled to the mating member 5016 via other types of engagements including, but not limited to, an interference or friction fit, or a frangible member or substance that may be broken with minimal separation force (e.g., axial or rotational force).

In some embodiments, the sensor cap 5018 may comprise a monolithic (singular) structure extending between the first and second ends 5020a, b. In other embodiments, however, the sensor cap 5018 may comprise two or more component parts. In the illustrated embodiment, for example, the sensor cap 5018 may include a seal ring 5028 positioned at the first end 5020a and a desiccant cap 5030 arranged at the second end 5020b. The seal ring 5028 may be configured to help seal the inner chamber 5022, as described in more detail below. In at least one embodiment, the seal ring 5028 may comprise an elastomeric O-ring. The desiccant cap 5030 may house or comprise a desiccant to help maintain preferred humidity levels within the inner chamber 5022. The desiccant cap 5030 may also define or otherwise provide the engagement feature 5024 of the sensor cap 5018.

Figure 11B:
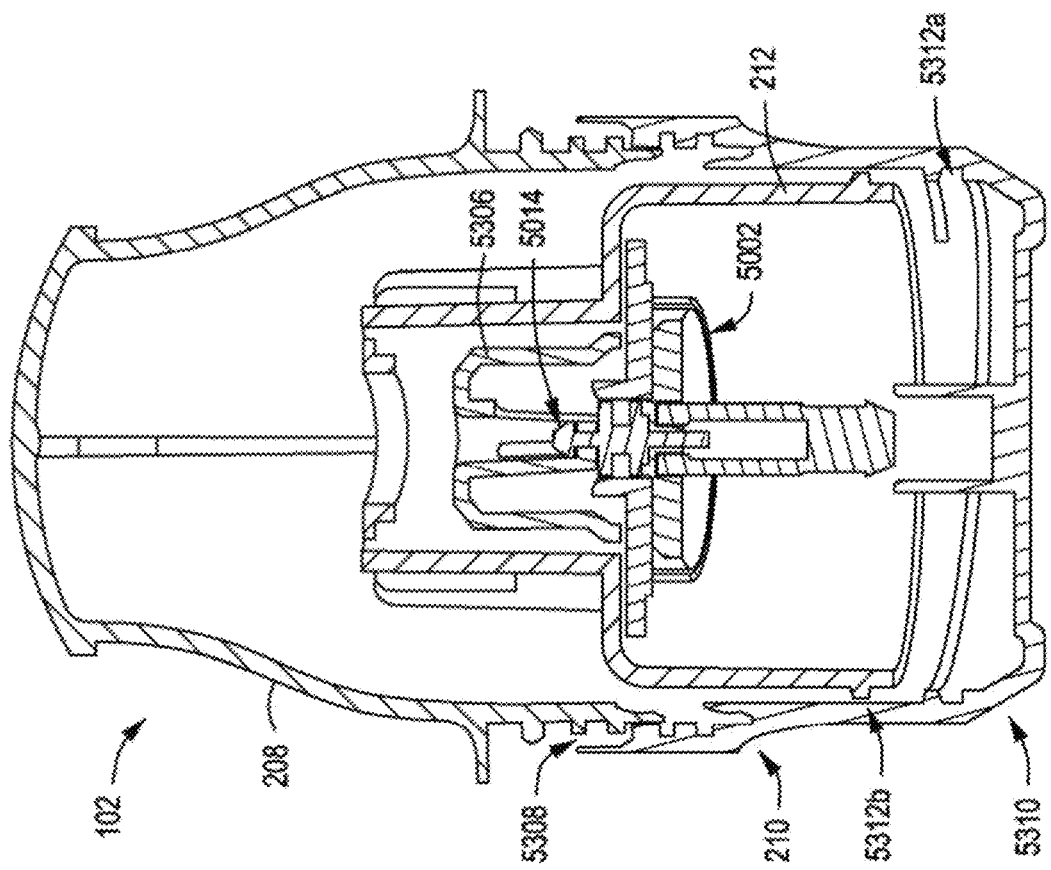
FIGS. 11A-11C are progressive cross-sectional side views showing assembly of the sensor applicator with the sensor control device of FIGS. 10A-10B.
Figure 11A:
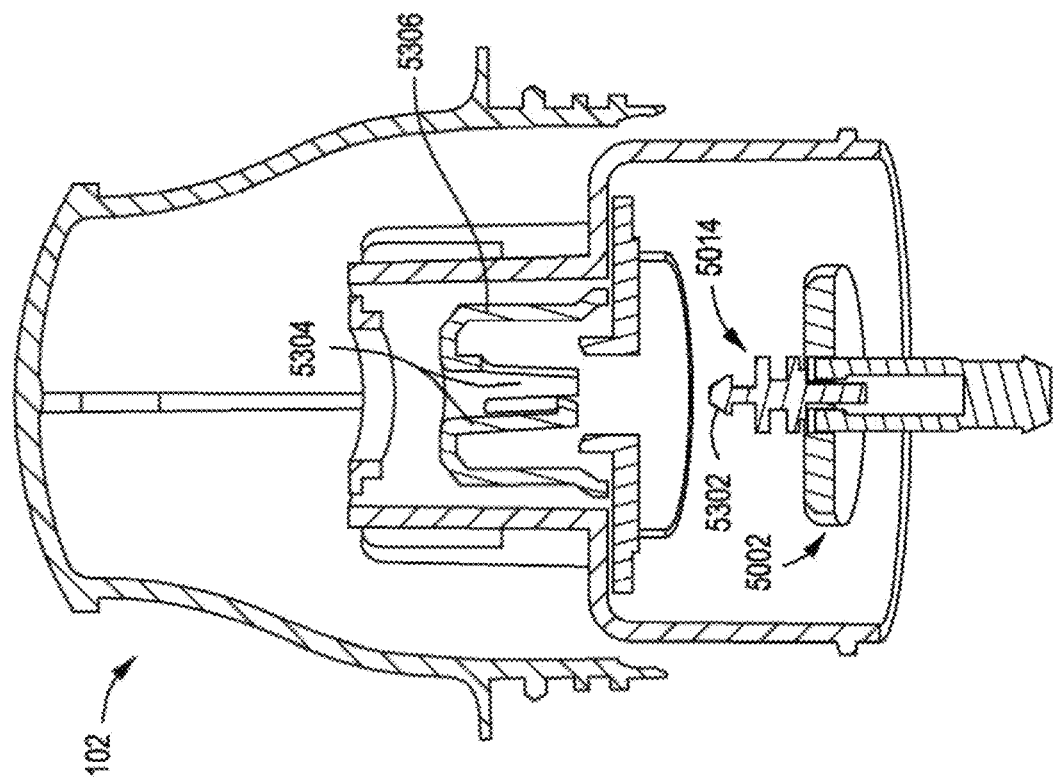
Figure 11C:
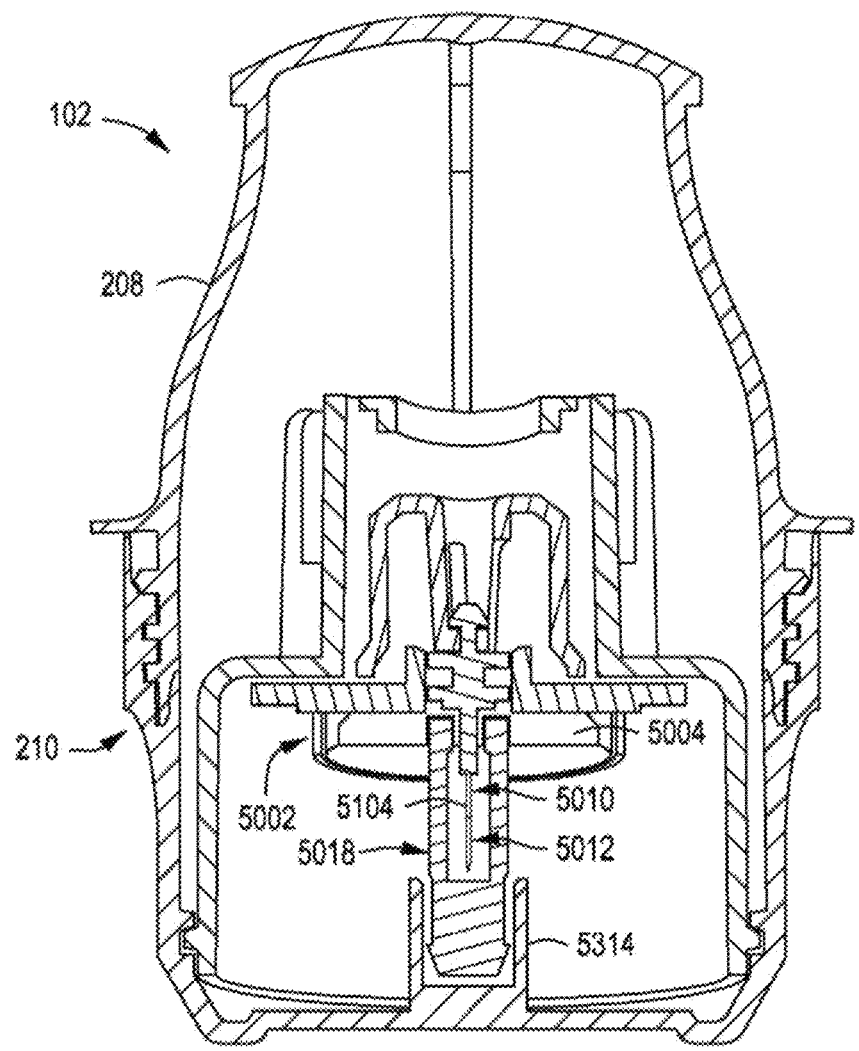

FIGS. 11A-11C are progressive cross-sectional side views showing assembly of the sensor applicator 102 with the sensor control device 5002, according to one or more embodiments. Once the sensor control device 5002 is fully assembled, it may then be loaded into the sensor applicator 102. With reference to FIG. 11A, the sharp hub 5014 may include or otherwise define a hub snap pawl 5302 configured to help couple the sensor control device 5002 to the sensor applicator 102. More specifically, the sensor control device 5002 may be advanced into the interior of the sensor applicator 102 and the hub snap pawl 5302 may be received by corresponding arms 5304 of a sharp carrier 5306 positioned within the sensor applicator 102.

In FIG. 11B, the sensor control device 5002 is shown received by the sharp carrier 5306 and, therefore, secured within the sensor applicator 102. Once the sensor control device 5002 is loaded into the sensor applicator 102, the applicator cap 210 may be coupled to the sensor applicator 102. In some embodiments, the applicator cap 210 and the housing 208 may have opposing, matable sets of threads 5308 that enable the applicator cap 210 to be screwed onto the housing 208 in a clockwise (or counter-clockwise) direction and thereby secure the applicator cap 210 to the sensor applicator 102.

As illustrated, the sheath 212 is also positioned within the sensor applicator 102, and the sensor applicator 102 may include a sheath locking mechanism 5310 configured to ensure that the sheath 212 does not prematurely collapse during a shock event. In the illustrated embodiment, the sheath locking mechanism 5310 may comprise a threaded engagement between the applicator cap 210 and the sheath 212. More specifically, one or more internal threads 5312a may be defined or otherwise provided on the inner surface of the applicator cap 210, and one or more external threads 5312b may be defined or otherwise provided on the sheath 212. The internal and external threads 5312a,b may be configured to threadably mate as the applicator cap 210 is threaded to the sensor applicator 102 at the threads 5308. The internal and external threads 5312a,b may have the same thread pitch as the threads 5308 that enable the applicator cap 210 to be screwed onto the housing 208.

In FIG. 11C, the applicator cap 210 is shown fully threaded (coupled) to the housing 208. As illustrated, the applicator cap 210 may further provide and otherwise define a cap post 5314 centrally located within the interior of the applicator cap 210 and extending proximally from the bottom thereof. The cap post 5314 may be configured to receive at least a portion of the sensor cap 5018 as the applicator cap 210 is screwed onto the housing 208.

With the sensor control device 5002 loaded within the sensor applicator 102 and the applicator cap 210 properly secured, the sensor control device 5002 may then be subjected to a gaseous chemical sterilization configured to sterilize the electronics housing 5004 and any other exposed portions of the sensor control device 5002. Since the distal portions of the sensor 5010 and the sharp 5012 are sealed within the sensor cap 5018, the chemicals used during the gaseous chemical sterilization process are unable to interact with the enzymes, chemistry, and biologics provided on the tail 5104, and other sensor components, such as membrane coatings that regulate analyte influx.

Figure 12B:
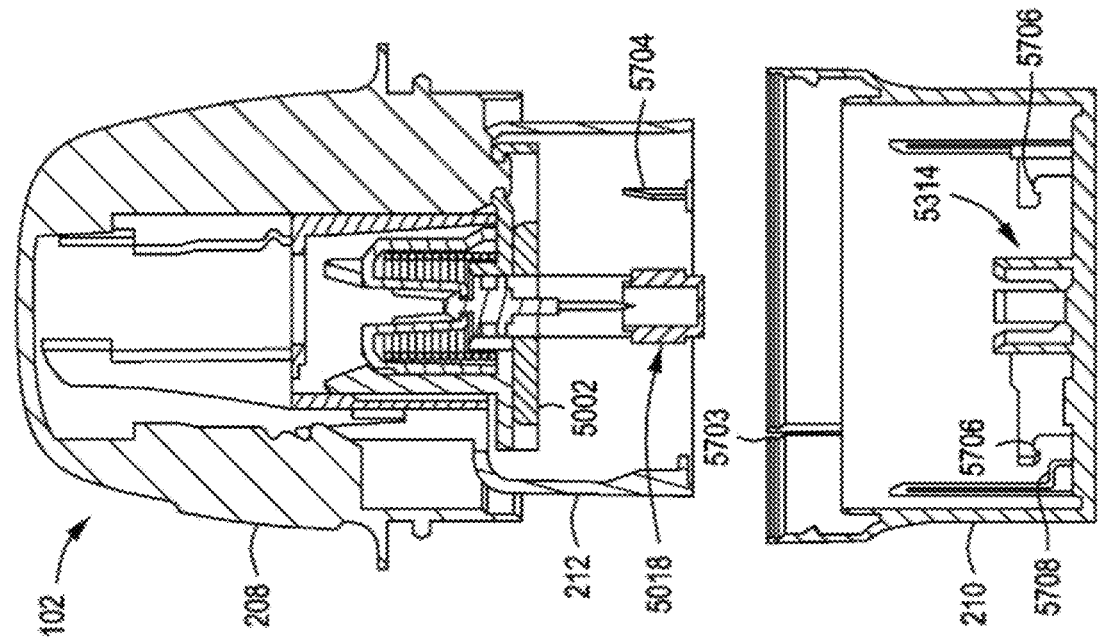
FIGS. 12A-12C are progressive cross-sectional side views showing assembly and disassembly of an example embodiment of the sensor applicator with the sensor control device of FIGS. 10A-10B.
Figure 12A:
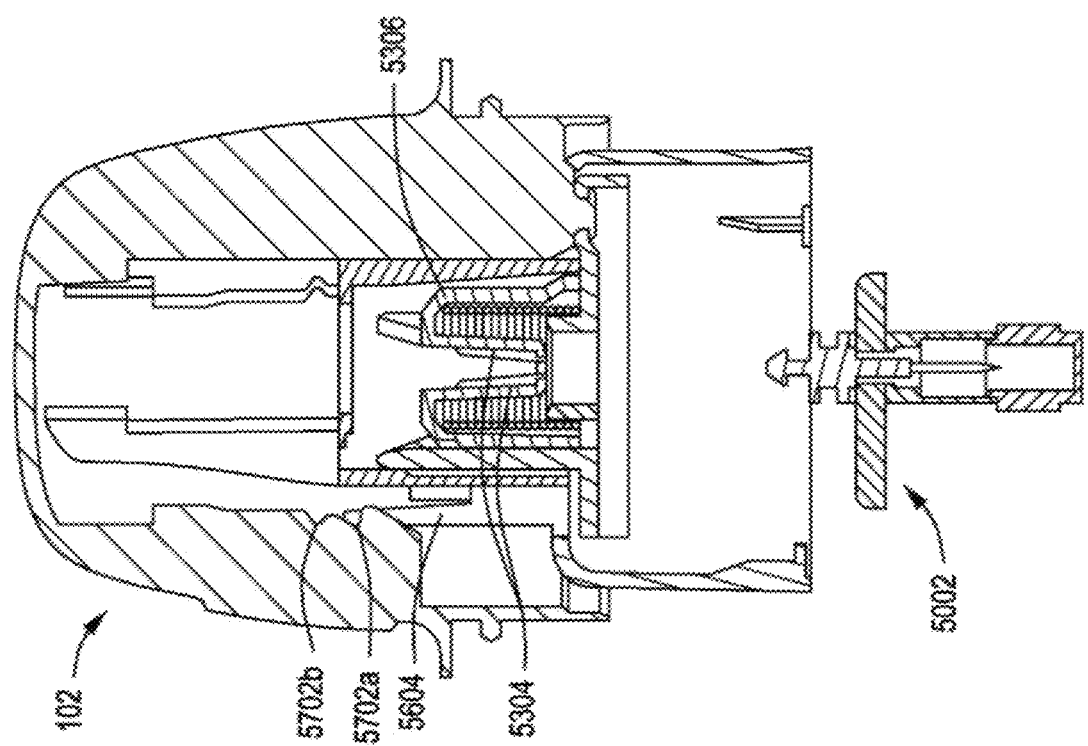
Figure 12C:
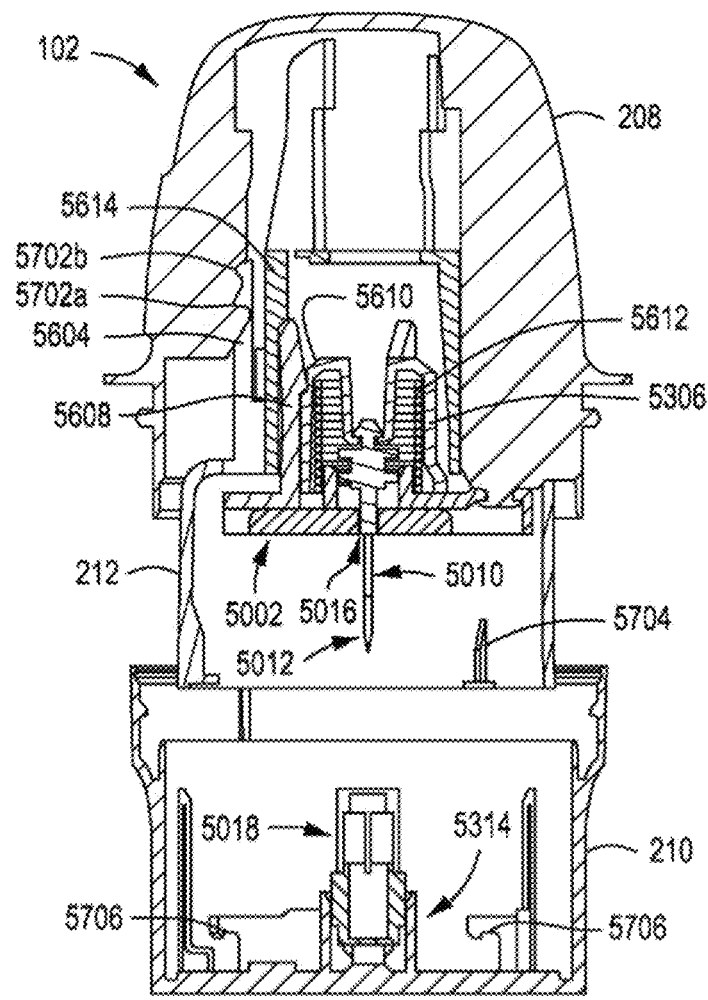

FIGS. 12A-12C are progressive cross-sectional side views showing assembly and disassembly of an alternative embodiment of the sensor applicator 102 with the sensor control device 5002, according to one or more additional embodiments. A fully assembled sensor control device 5002 may be loaded into the sensor applicator 102 by coupling the hub snap pawl 5302 into the arms 5304 of the sharp carrier 5306 positioned within the sensor applicator 102, as generally described above.

In the illustrated embodiment, the sheath arms 5604 of the sheath 212 may be configured to interact with a first detent 5702a and a second detent 5702b defined within the interior of the housing 208. The first detent 5702a may alternately be referred to a "locking" detent, and the second detent 5702b may alternately be referred to as a "firing" detent. When the sensor control device 5002 is initially installed in the sensor applicator 102, the sheath arms 5604 may be received within the first detent 5702a. As discussed below, the sheath 212 may be actuated to move the sheath arms 5604 to the second detent 5702b, which places the sensor applicator 102 in firing position.

In FIG. 12B, the applicator cap 210 is aligned with the housing 208 and advanced toward the housing 208 so that the sheath 212 is received within the applicator cap 210. Instead of rotating the applicator cap 210 relative to the housing 208, the threads of the applicator cap 210 may be snapped onto the corresponding threads of the housing 208 to couple the applicator cap 210 to the housing 208. Axial cuts or slots 5703 (one shown) defined in the applicator cap 210 may allow portions of the applicator cap 210 near its threading to flex outward to be snapped into engagement with the threading of the housing 208. As the applicator cap 210 is snapped to the housing 208, the sensor cap 5018 may correspondingly be snapped into the cap post 5314.

Similar to the embodiment of FIGS. 11A-11C, the sensor applicator 102 may include a sheath locking mechanism configured to ensure that the sheath 212 does not prematurely collapse during a shock event. In the illustrated embodiment, the sheath locking mechanism includes one or more ribs 5704 (one shown) defined near the base of the sheath 212 and configured to interact with one or more ribs 5706 (two shown) and a shoulder 5708 defined near the base of the applicator cap 210. The ribs 5704 may be configured to inter-lock between the ribs 5706 and the shoulder 5708 while attaching the applicator cap 210 to the housing 208. More specifically, once the applicator cap 210 is snapped onto the housing 208, the applicator cap 210 may be rotated (e.g., clockwise), which locates the ribs 5704 of the sheath 212 between the ribs 5706 and the shoulder 5708 of the applicator cap 210 and thereby "locks" the applicator cap 210 in place until the user reverse rotates the applicator cap 210 to remove the applicator cap 210 for use. Engagement of the ribs 5704 between the ribs 5706 and the shoulder 5708 of the applicator cap 210 may also prevent the sheath 212 from collapsing prematurely.

In FIG. 12C, the applicator cap 210 is removed from the housing 208. As with the embodiment of FIGS. 12A-12C, the applicator cap 210 can be removed by reverse rotating the applicator cap 210, which correspondingly rotates the cap post 5314 in the same direction and causes sensor cap 5018 to unthread from the mating member 5016, as generally described above. Moreover, detaching the sensor cap 5018 from the sensor control device 5002 exposes the distal portions of the sensor 5010 and the sharp 5012.

As the applicator cap 210 is unscrewed from the housing 208, the ribs 5704 defined on the sheath 212 may slidingly engage the tops of the ribs 5706 defined on the applicator cap 210. The tops of the ribs 5706 may provide corresponding ramped surfaces that result in an upward displacement of the sheath 212 as the applicator cap 210 is rotated, and moving the sheath 212 upward causes the sheath arms 5604 to flex out of engagement with the first detent 5702a to be received within the second detent 5702b. As the sheath 212 moves to the second detent 5702b, the radial shoulder 5614 moves out of radial engagement with the carrier arm(s) 5608, which allows the passive spring force of the spring 5612 to push upward on the sharp carrier 5306 and force the carrier arm(s) 5608 out of engagement with the groove(s) 5610. As the sharp carrier 5306 moves upward within the housing 208, the mating member 5016 may correspondingly retract until it becomes flush, substantially flush, or sub-flush with the bottom of the sensor control device 5002. At this point, the sensor applicator 102 in firing position. Accordingly, in this embodiment, removing the applicator cap 210 correspondingly causes the mating member 5016 to retract.

I. Exemplary Firing Mechanism of One-Piece and Two-Piece Applicators

FIGS. 13A-13F illustrate example details of embodiments of the internal device mechanics of "firing" the applicator 216 to apply sensor control device 222 to a user and including retracting sharp 1030 safely back into used applicator 216. All together, these drawings represent an example sequence of driving sharp 1030 (supporting a sensor coupled to sensor control device 222) into the skin of a user, withdrawing the sharp while leaving the sensor behind in operative contact with interstitial fluid of the user, and adhering the sensor control device to the skin of the user with an adhesive. Modification of such activity for use with the alternative applicator assembly embodiments and components can be appreciated in reference to the same by those with skill in the art. Moreover, applicator 216 may be a sensor applicator having one-piece architecture or a two-piece architecture as disclosed herein.

Figure 13A:
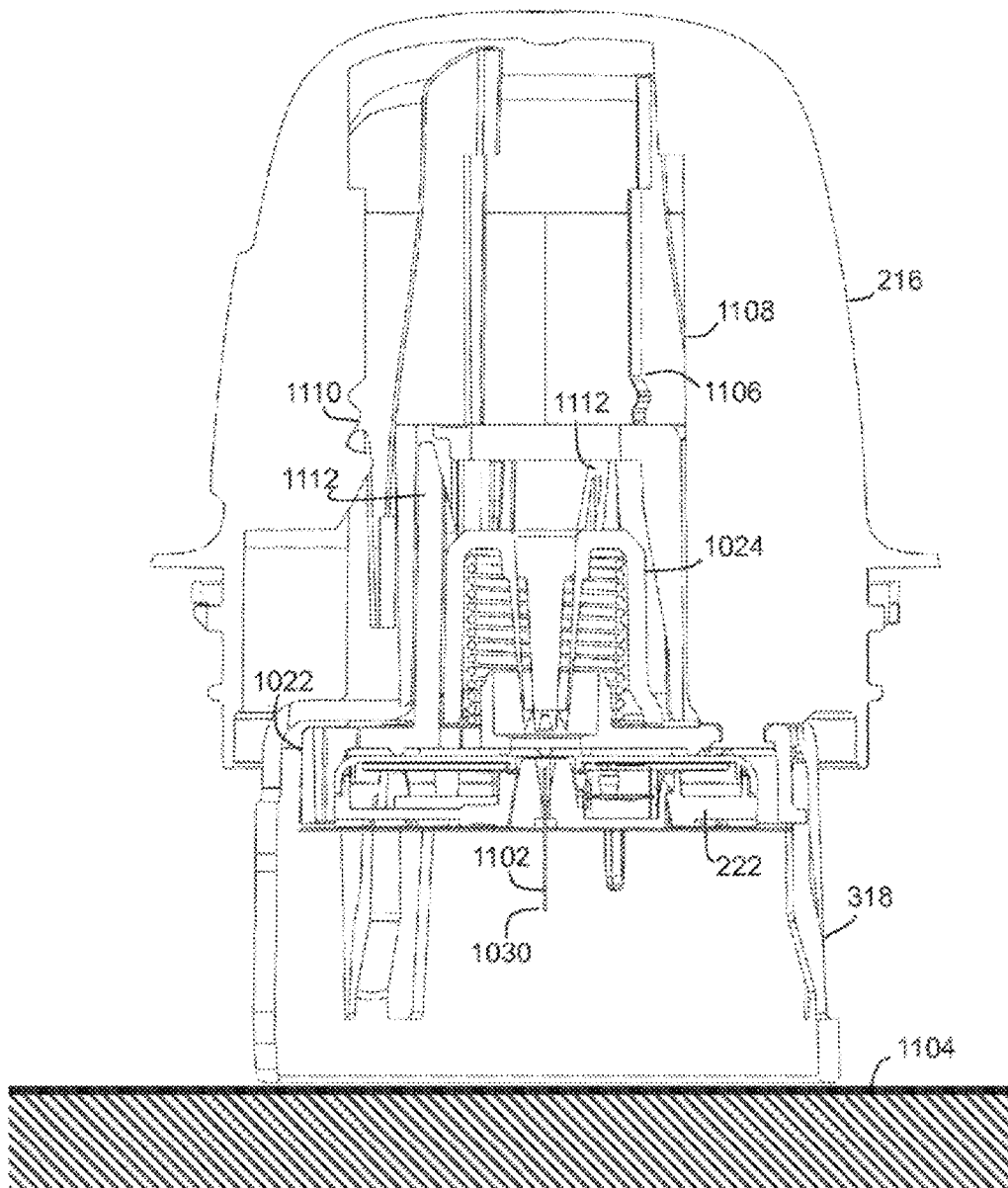
FIGS. 13A-13F illustrate cross-sectional views depicting an example embodiment of an applicator during a stage of deployment.

Turning now to FIG. 13A, a sensor 1102 is supported within sharp 1030, just above the skin 1104 of the user. Rails 1106 (optionally three of them) of an upper guide section 1108 may be provided to control applicator 216 motion relative to sheath 318. The sheath 318 is held by detent features 1110 within the applicator 216 such that appropriate downward force along the longitudinal axis of the applicator 216 will cause the resistance provided by the detent features 1110 to be overcome so that sharp 1030 and sensor control device 222 can translate along the longitudinal axis into (and onto) skin 1104 of the user. In addition, catch arms 1112 of sensor carrier 1022 engage the sharp retraction assembly 1024 to maintain the sharp 1030 in a position relative to the sensor control device 222.

Figure 13B:
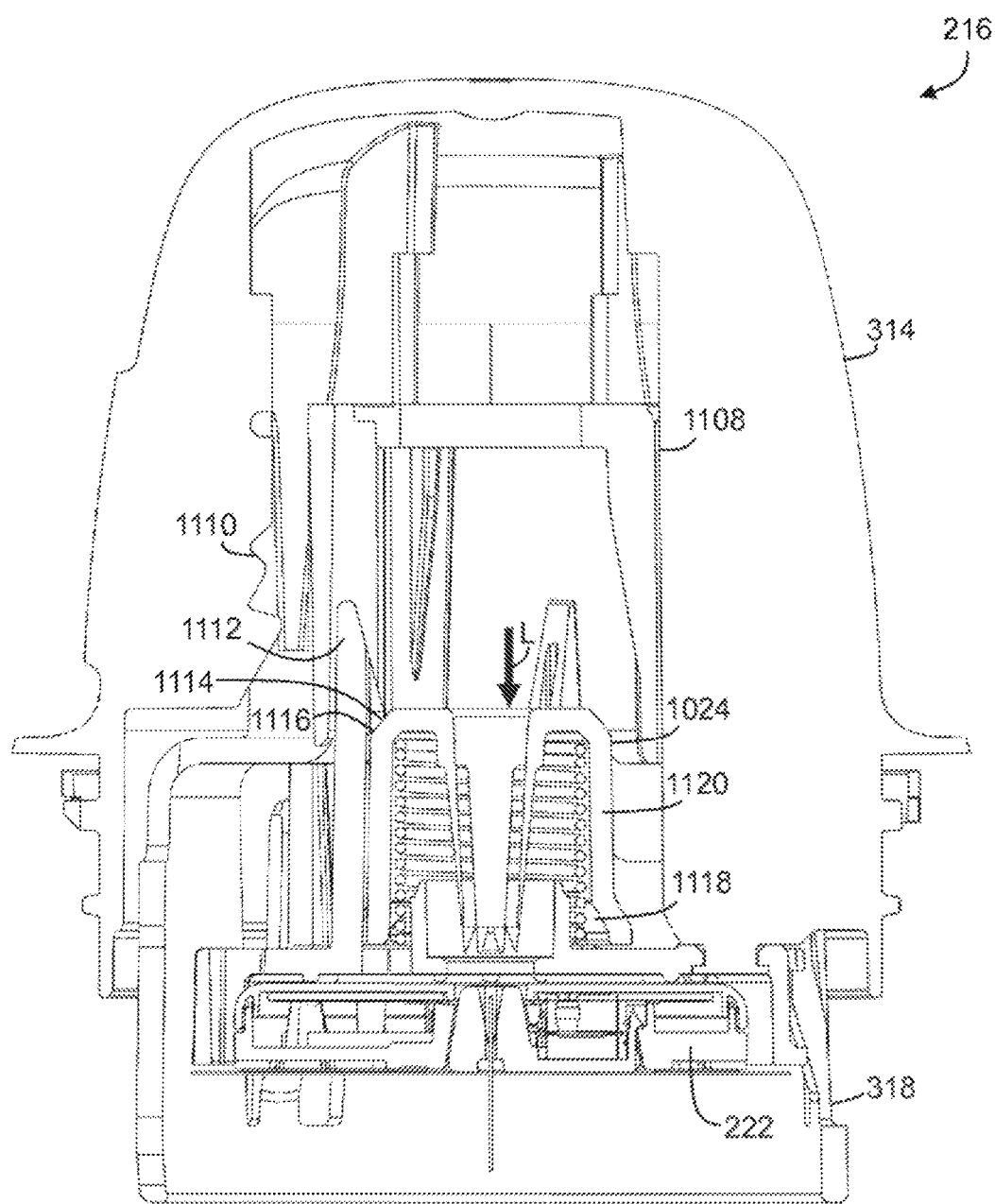

In FIG. 13B, user force is applied to overcome or override detent features 1110 and sheath 318 collapses into housing 314 driving the sensor control device 222 (with associated parts) to translate down as indicated by the arrow L along the longitudinal axis. An inner diameter of the upper guide section 1108 of the sheath 318 constrains the position of carrier arms 1112 through the full stroke of the sensor/sharp insertion process. The retention of the stop surfaces 1114 of carrier arms 1112 against the complimentary faces 1116 of the sharp retraction assembly 1024 maintains the position of the members with return spring 1118 fully energized. According to embodiments, rather than employing user force to drive the sensor control device 222 to translate down as indicated by the arrow L along the longitudinal axis, housing 314 can include a button (for example, not limitation, a push button) which activates a drive spring (for example, not limitation, a coil spring) to drive the sensor control device 222.

Figure 13C:
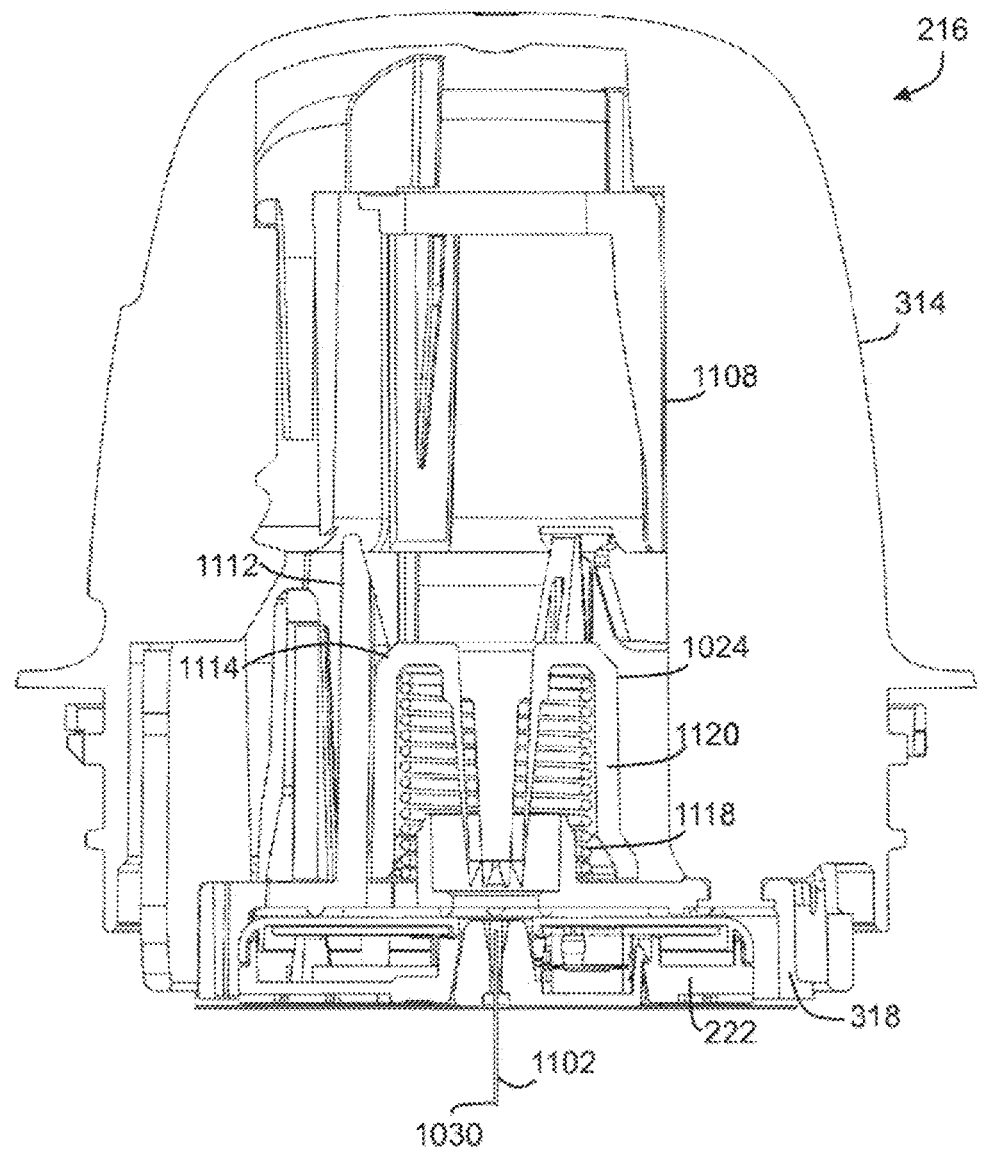
Figure 13D:
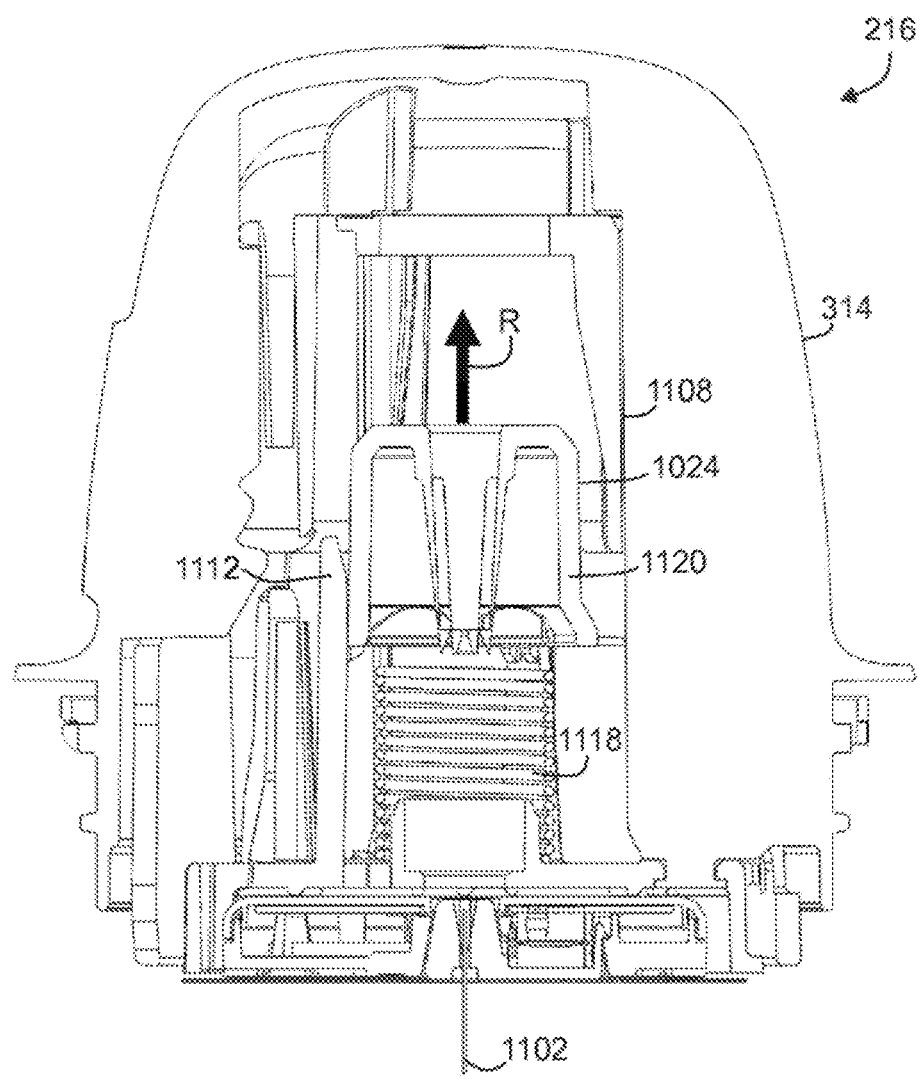

In FIG. 13C, sensor 1102 and sharp 1030 have reached full insertion depth. In so doing, the carrier arms 1112 clear the upper guide section 1108 inner diameter. Then, the compressed force of the coil return spring 1118 drives angled stop surfaces 1114 radially outward, releasing force to drive the sharp carrier 1102 of the sharp retraction assembly 1024 to pull the (slotted or otherwise configured) sharp 1030 out of the user and off of the sensor 1102 as indicated by the arrow R in FIG. 13D.

Figure 13E:
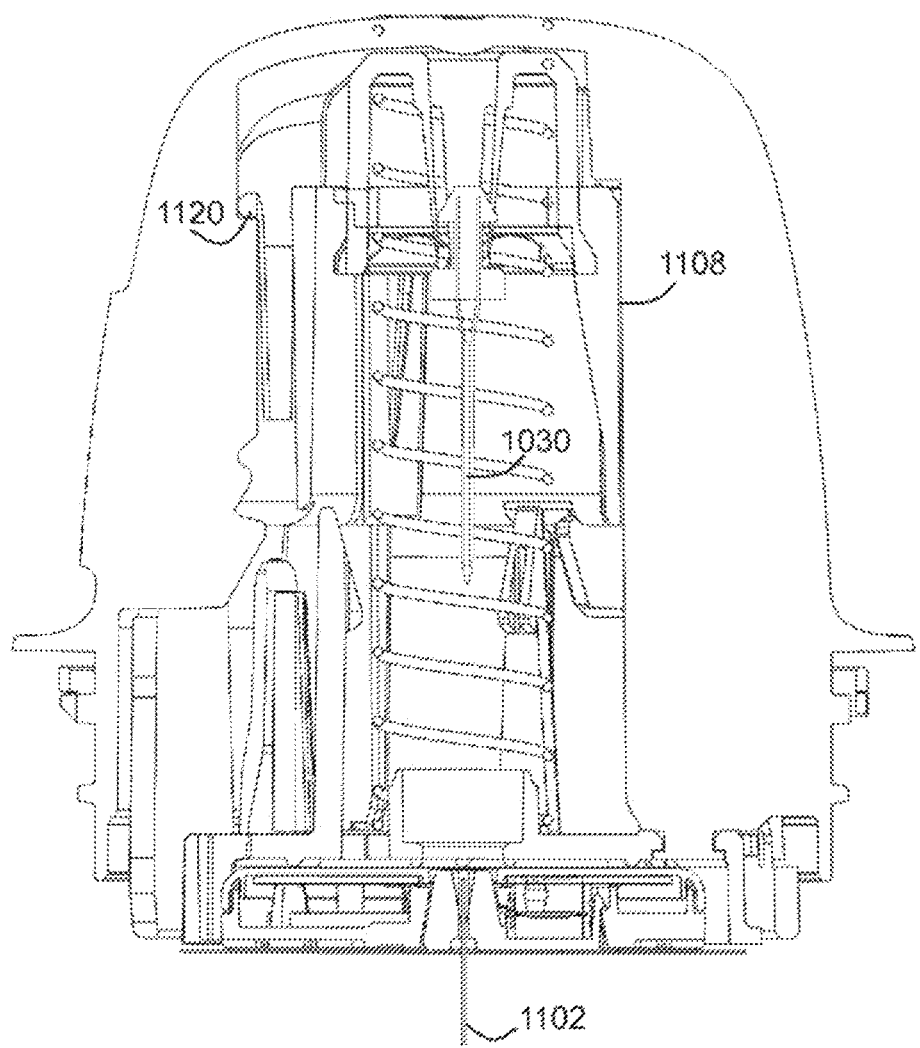
Figure 13F:
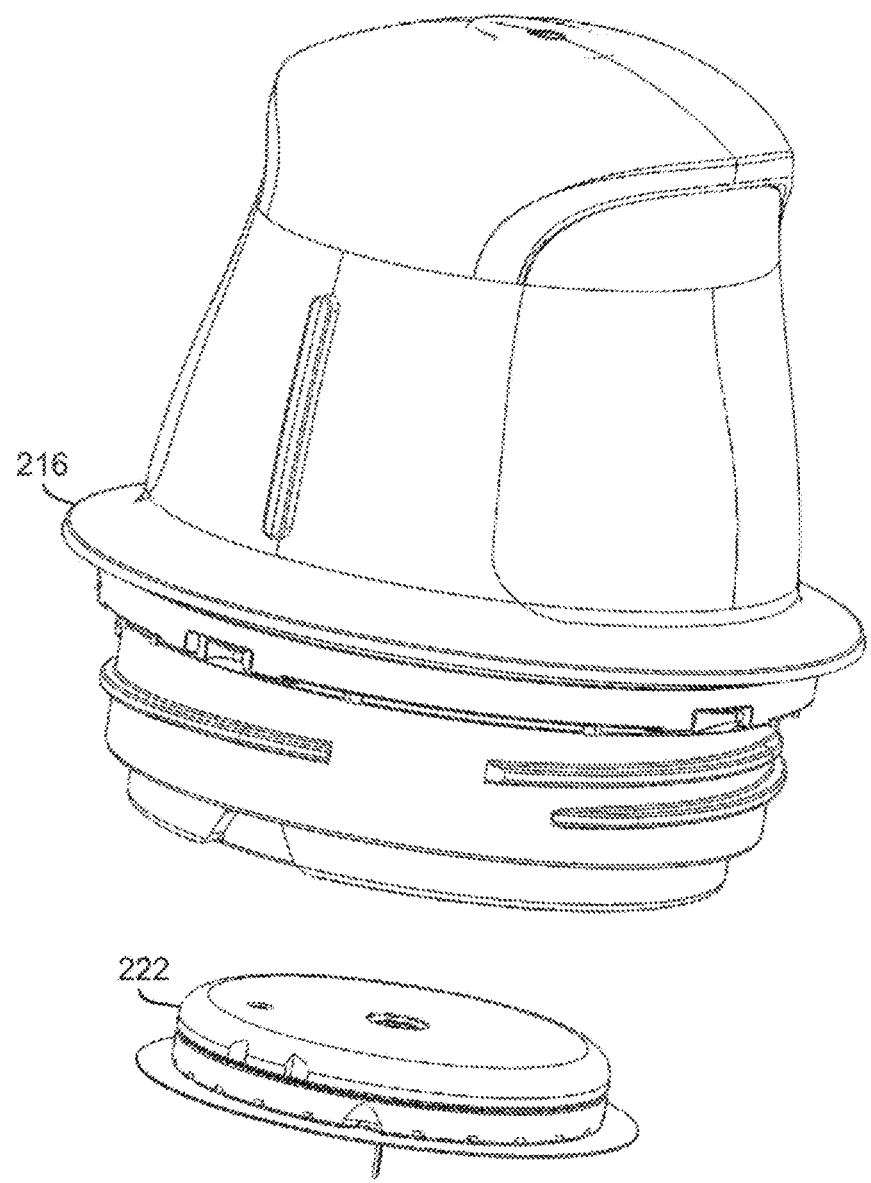

With the sharp 1030 fully retracted as shown in FIG. 13E, the upper guide section 1108 of the sheath 318 is set with a final locking feature 1120. As shown in FIG. 13F, the spent applicator assembly 216 is removed from the insertion site, leaving behind the sensor control device 222, and with the sharp 1030 secured safely inside the applicator assembly 216. The spent applicator assembly 216 is now ready for disposal.

Operation of the applicator 216 when applying the sensor control device 222 is designed to provide the user with a sensation that both the insertion and retraction of the sharp 1030 is performed automatically by the internal mechanisms of the applicator 216. In other words, the present invention avoids the user experiencing the sensation that he is manually driving the sharp 1030 into his skin. Thus, once the user applies sufficient force to overcome the resistance from the detent features of the applicator 216, the resulting actions of the applicator 216 are perceived to be an automated response to the applicator being "triggered." The user does not perceive that he is supplying additional force to drive the sharp 1030 to pierce his skin despite that all the driving force is provided by the user and no additional biasing/driving means are used to insert the sharp 1030. As detailed above in FIG. 13C, the retraction of the sharp 1030 is automated by the coil return spring 1118 of the applicator 216.

With respect to any of the applicator embodiments described herein, as well as any of the components thereof, including but not limited to the sharp, sharp module and sensor module embodiments, those of skill in the art will understand that said embodiments can be dimensioned and configured for use with sensors configured to sense an analyte level in a bodily fluid in the epidermis, dermis, or subcutaneous tissue of a subject. In some embodiments, for example, sharps and distal portions of analyte sensors disclosed herein can both be dimensioned and configured to be positioned at a particular end-depth (i.e., the furthest point of penetration in a tissue or layer of the subject's body, e.g., in the epidermis, dermis, or subcutaneous tissue). With respect to some applicator embodiments, those of skill in the art will appreciate that certain embodiments of sharps can be dimensioned and configured to be positioned at a different end-depth in the subject's body relative to the final end-depth of the analyte sensor. In some embodiments, for example, a sharp can be positioned at a first end-depth in the subject's epidermis prior to retraction, while a distal portion of an analyte sensor can be positioned at a second end-depth in the subject's dermis. In other embodiments, a sharp can be positioned at a first end-depth in the subject's dermis prior to retraction, while a distal portion of an analyte sensor can be positioned at a second end-depth in the subject's subcutaneous tissue. In still other embodiments, a sharp can be positioned at a first end-depth prior to retraction and the analyte sensor can be positioned at a second end-depth, wherein the first end-depth and second end-depths are both in the same layer or tissue of the subject's body.

Additionally, with respect to any of the applicator embodiments described herein, those of skill in the art will understand that an analyte sensor, as well as one or more structural components coupled thereto, including but not limited to one or more spring-mechanisms, can be disposed within the applicator in an off-center position relative to one or more axes of the applicator. In some applicator embodiments, for example, an analyte sensor and a spring mechanism can be disposed in a first off-center position relative to an axis of the applicator on a first side of the applicator, and the sensor electronics can be disposed in a second off-center position relative to the axis of the applicator on a second side of the applicator. In other applicator embodiments, the analyte sensor, spring mechanism, and sensor electronics can be disposed in an off-center position relative to an axis of the applicator on the same side. Those of skill in the art will appreciate that other permutations and configurations in which any or all of the analyte sensor, spring mechanism, sensor electronics, and other components of the applicator are disposed in a centered or off-centered position relative to one or more axes of the applicator are possible and fully within the scope of the present disclosure.

Additional details of suitable devices, systems, methods, components and the operation thereof along with related features are set forth in International Publication No. WO 2018/136898 to Rao et al., International Publication No. WO 2019/236850 to Thomas et al., International Publication No. WO 2019/236859 to Thomas et al., International Publication No. WO 2019/236876 to Thomas et al., and U.S. Patent Publication No. 2020/0196919, filed Jun. 6, 2019, each of which is incorporated by reference in its entirety herein. Further details regarding embodiments of applicators, their components, and variants thereof, are described in U.S. Patent Publication Nos. 2013/0150691, 2016/0331283, and 2018/0235520, all of which are incorporated by reference herein in their entireties and for all purposes. Further details regarding embodiments of sharp modules, sharps, their components, and variants thereof, are described in U.S. Patent Publication No. 2014/0171771, which is incorporated by reference herein in its entirety and for all purposes.

J. Exemplary Methods of Calibrating Analyte Sensors

Biochemical sensors can be described by one or more sensing characteristics. A common sensing characteristic is referred to as the biochemical sensor's sensitivity, which is a measure of the sensor's responsiveness to the concentration of the chemical or composition it is designed to detect. For electrochemical sensors, this response can be in the form of an electrical current (amperometric) or electrical charge (coulometric). For other types of sensors, the response can be in a different form, such as a photonic intensity (e.g., optical light). The sensitivity of a biochemical analyte sensor can vary depending on a number of factors, including whether the sensor is in an in vitro state or an in vivo state.

Figure 14:
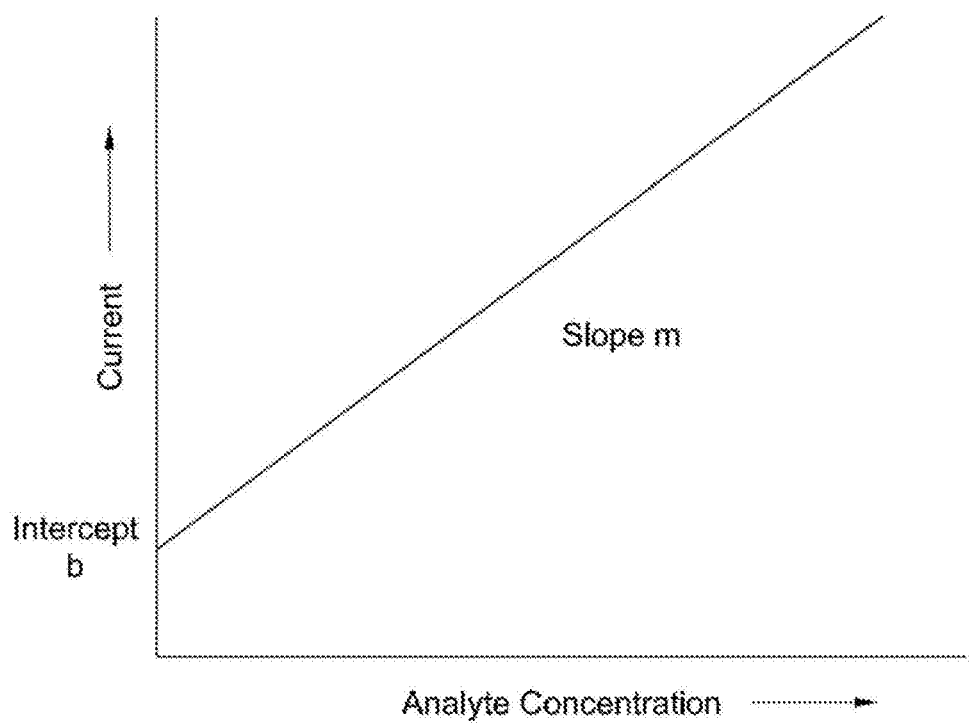
FIG. 14 is a graph depicting an example of an in vitro sensitivity of an analyte sensor.

FIG. 14 is a graph depicting the in vitro sensitivity of an amperometric analyte sensor. The in vitro sensitivity can be obtained by in vitro testing the sensor at various analyte concentrations and then performing a regression (e.g., linear or non-linear) or other curve fitting on the resulting data. In this example, the analyte sensor's sensitivity is linear, or substantially linear, and can be modeled according to the equation $y=mx+b$, where y is the sensor's electrical output current, x is the analyte level (or concentration), m is the slope of the sensitivity and b is the intercept of the sensitivity, where the intercept generally corresponds to a background signal (e.g., noise). For sensors with a linear or substantially linear response, the analyte level that corresponds to a given current can be determined from the slope and intercept of the sensitivity. Sensors with a non-linear sensitivity require additional information to determine the analyte level resulting from the sensor's output current, and those of ordinary skill in the art are familiar with manners by which to model non-linear sensitivities. In certain embodiments of in vivo sensors, the in vitro sensitivity can be the same as the in vivo sensitivity, but in other embodiments a transfer (or conversion) function is used to translate the in vitro sensitivity into the in vivo sensitivity that is applicable to the sensor's intended in vivo use.

Calibration is a technique for improving or maintaining accuracy by adjusting a sensor's measured output to reduce the differences with the sensor's expected output. One or more parameters that describe the sensor's sensing characteristics, like its sensitivity, are established for use in the calibration adjustment.

Certain in vivo analyte monitoring systems require calibration to occur after implantation of the sensor into the user or patient, either by user interaction or by the system itself in an automated fashion. For example, when user interaction is required, the user performs an in vitro measurement (e.g., a blood glucose (BG) measurement using a finger stick and an in vitro test strip) and enters this into the system, while the analyte sensor is implanted. The system then compares the in vitro measurement with the in vivo signal and, using the differential, determines an estimate of the sensor's in vivo sensitivity. The in vivo sensitivity can then be used in an algorithmic process to transform the data collected with the sensor to a value that indicates the user's analyte level. This and other processes that require user action to perform calibration are referred to as "user calibration." Systems can require user calibration due to instability of the sensor's sensitivity, such that the sensitivity drifts or changes over time. Thus, multiple user calibrations (e.g., according to a periodic (e.g., daily) schedule, variable schedule, or on an as-needed basis) can be required to maintain accuracy. While the embodiments described herein can incorporate a degree of user calibration for a particular implementation, generally this is not preferred as it requires the user to perform a painful or otherwise burdensome BG measurement, and can introduce user error.

Some in vivo analyte monitoring systems can regularly adjust the calibration parameters through the use of automated measurements of characteristics of the sensor made by the system itself (e.g., processing circuitry executing software). The repeated adjustment of the sensor's sensitivity based on a variable measured by the system (and not the user) is referred to generally as "system" (or automated) calibration, and can be performed with user calibration, such as an early BG measurement, or without user calibration. Like the case with repeated user calibrations, repeated system calibrations are typically necessitated by drift in the sensor's sensitivity over time. Thus, while the embodiments described herein can be used with a degree of automated system calibration, preferably the sensor's sensitivity is relatively stable over time such that post-implantation calibration is not required.

Some in vivo analyte monitoring systems operate with a sensor that is factory calibrated. Factory calibration refers to the determination or estimation of the one or more calibration parameters prior to distribution to the user or healthcare professional (HCP). The calibration parameter can be determined by the sensor manufacturer (or the manufacturer of the other components of the sensor control device if the two entities are different). Many in vivo sensor manufacturing processes fabricate the sensors in groups or batches referred to as production lots, manufacturing stage lots, or simply lots. A single lot can include thousands of sensors.

Sensors can include a calibration code or parameter which can be derived or determined during one or more sensor manufacturing processes and coded or programmed, as part of the manufacturing process, in the data processing device of the analyte monitoring system or provided on the sensor itself, for example, as a bar code, a laser tag, an RFID tag, or other machine readable information provided on the sensor. User calibration during in vivo use of the sensor can be obviated, or the frequency of in vivo calibrations during sensor wear can be reduced if the code is provided to a receiver (or other data processing device). In embodiments where the calibration code or parameter is provided on the sensor itself, prior to or at the start of the sensor use, the calibration code or parameter can be automatically transmitted or provided to the data processing device in the analyte monitoring system.

Some in vivo analyte monitoring system operate with a sensor that can be one or more of factory calibrated, system calibrated, and/or user calibrated. For example, the sensor can be provided with a calibration code or parameter which can allow for factory calibration. If the information is provided to a receiver (for example, entered by a user), the sensor can operate as a factory calibrated sensor. If the information is not provided to a receiver, the sensor can operate as a user calibrated sensor and/or a system calibrated sensor.

In a further aspect, programming or executable instructions can be provided or stored in the data processing device of the analyte monitoring system, and/or the receiver/controller unit, to provide a time varying adjustment algorithm to the in vivo sensor during use. For example, based on a retrospective statistical analysis of analyte sensors used in vivo and the corresponding glucose level feedback, a predetermined or analytical curve or a database can be generated which is time based, and configured to provide additional adjustment to the one or more in vivo sensor parameters to compensate for potential sensor drift in stability profile, or other factors.

In accordance with the disclosed subject matter, the analyte monitoring system can be configured to compensate or adjust for the sensor sensitivity based on a sensor drift profile. A time varying parameter $\beta(t)$ can be defined or determined based on analysis of sensor behavior during in vivo use, and a time varying drift profile can be determined. In certain aspects, the compensation or adjustment to the sensor sensitivity can be programmed in the receiver unit, the controller or data processor of the analyte monitoring system such that the compensation or the adjustment or both can be performed automatically and/or iteratively when sensor data is received from the analyte sensor. In accordance with the disclosed subject matter, the adjustment or compensation algorithm can be initiated or executed by the user (rather than self-initiating or executing) such that the adjustment or the compensation to the analyte sensor sensitivity profile is performed or executed upon user initiation or activation of the corresponding function or routine, or upon the user entering the sensor calibration code.

In accordance with the disclosed subject matter, each sensor in the sensor lot (in some instances not including sample sensors used for in vitro testing) can be examined non-destructively to determine or measure its characteristics such as membrane thickness at one or more points of the sensor, and other characteristics including physical characteristics such as the surface area/volume of the active area can be measured or determined. Such measurement or determination can be performed in an automated manner using, for example, optical scanners or other suitable measurement devices or systems, and the determined sensor characteristics for each sensor in the sensor lot is compared to the corresponding mean values based on the sample sensors for possible correction of the calibration parameter or code assigned to each sensor. For example, for a calibration parameter defined as the sensor sensitivity, the sensitivity is approximately inversely proportional to the membrane thickness, such that, for example, a sensor having a measured membrane thickness of approximately 4% greater than the mean membrane thickness for the sampled sensors from the same sensor lot as the sensor, the sensitivity assigned to that sensor in one embodiment is the mean sensitivity determined from the sampled sensors divided by 1.04. Likewise, since the sensitivity is approximately proportional to active area of the sensor, a sensor having measured active area of approximately 3% lower than the mean active area for the sampled sensors from the same sensor lot, the sensitivity assigned to that sensor is the mean sensitivity multiplied by 0.97. The assigned sensitivity can be determined from the mean sensitivity from the sampled sensors, by multiple successive adjustments for each examination or measurement of the sensor. In certain embodiments, examination or measurement of each sensor can additionally include measurement of membrane consistency or texture in addition to the membrane thickness and/or surface are or volume of the active sensing area.

Additional information regarding sensor calibration is provided in U.S. Publication No. 2010/00230285 and U.S. Publication No. 2019/0274598, each of which is incorporated by reference herein in its entirety.

K. Exemplary Bluetooth Communication Protocols

The storage memory 5030 of the sensor 110 can include the software blocks related to communication protocols of the communication module. For example, the storage memory 5030 can include a BLE services software block with functions to provide interfaces to make the BLE module 5041 available to the computing hardware of the sensor 110. These software functions can include a BLE logical interface and interface parser. BL E services offered by the communication module 5040 can include the generic access profile service, the generic attribute service, generic access service, device information service, data transmission services, and security services. The data transmission service can be a primary service used for transmitting data such as sensor control data, sensor status data, analyte measurement data (historical and current), and event log data. The sensor status data can include error data, current time active, and software state. The analyte measurement data can include information such as current and historical raw measurement values, current and historical values after processing using an appropriate algorithm or model, projections and trends of measurement levels, comparisons of other values to patient-specific averages, calls to action as determined by the algorithms or models and other similar types of data.

According to aspects of the disclosed subject matter, and as embodied herein, a sensor 110 can be configured to communicate with multiple devices concurrently by adapting the features of a communication protocol or medium supported by the hardware and radios of the sensor 110. As an example, the BLE module 5041 of the communication module 5040 can be provided with software or firmware to enable multiple concurrent connections between the sensor 110 as a central device and the other devices as peripheral devices, or as a peripheral device where another device is a central device.

Connections, and ensuing communication sessions, between two devices using a communication protocol such as BLE can be characterized by a similar physical channel operated between the two devices (e.g., a sensor 110 and data receiving device 120). The physical channel can include a single channel or a series of channels, including for example and without limitation using an agreed upon series of channels determined by a common clock and channel- or frequency-hopping sequence. Communication sessions can use a similar amount of the available communication spectrum, and multiple such communication sessions can exist in proximity. In certain embodiment, each collection of devices in a communication session uses a different physical channel or series of channels, to manage interference of devices in the same proximity.

For purpose of illustration and not limitation, reference is made to an exemplary embodiment of a procedure for a sensor-receiver connection for use with the disclosed subject matter. First, the sensor 110 repeatedly advertises its connection information to its environment in a search for a data receiving device 120. The sensor 110 can repeat advertising on a regular basis until a connection established. The data receiving device 120 detects the advertising packet and scans and filters for the sensor 120 to connect to through the data provided in the advertising packet. Next, data receiving device 120 sends a scan request command and the sensor 110 responds with a scan response packet providing additional details. Then, the data receiving device 120 sends a connection request using the Bluetooth device address associated with the data receiving device 120. The data receiving device 120 can also continuously request to establish a connection to a sensor 110 with a specific Bluetooth device address. Then, the devices establish an initial connection allowing them to begin to exchange data. The devices begin a process to initialize data exchange services and perform a mutual authentication procedure.

During a first connection between the sensor 110 and data receiving device 120, the data receiving device 120 can initialize a service, characteristic, and attribute discovery procedure. The data receiving device 120 can evaluate these features of the sensor 110 and store them for use during subsequent connections. Next, the devices enable a notification for a customized security service used for mutual authentication of the sensor 110 and data receiving device 120. The mutual authentication procedure can be automated and require no user interaction. Following the successful completion of the mutual authentication procedure, the sensor 110 sends a connection parameter update to request the data receiving device 120 to use connection parameter settings preferred by the sensor 110 and configured to maximum longevity.

The data receiving device 120 then performs sensor control procedures to backfill historical data, current data, event log, and factory data. As an example, for each type of data, the data receiving device 120 sends a request to initiate a backfill process. The request can specify a range of records defined based on, for example, the measurement value, timestamp, or similar, as appropriate. The sensor 110 responds with requested data until all previously unsent data in the memory of the sensor 110 is delivered to the data receiving device 120. The sensor 110 can respond to a backfill request from the data receiving device 120 that all data has already been sent. Once backfill is completed, the data receiving device 120 can notify sensor 110 that it is ready to receive regular measurement readings. The sensor 110 can send readings across multiple notifications result on a repeating basis. As embodied herein, the multiple notifications can be redundant notifications to ensure that data is transmitted correctly. Alternatively, multiple notifications can make up a single payload.

For purpose of illustration and not limitation, reference is made to an exemplary embodiment of a procedure to send a shutdown command to the sensor 110. The shutdown operation is executed if the sensor 110 is in, for example, an error state, insertion failed state, or sensor expired state. If the sensor 110 is not in those states, the sensor 110 can log the command and execute the shutdown when sensor 110 transitions into the error state or sensor expired state. The data receiving device 120 sends a properly formatted shutdown command to the sensor 110. If the sensor 110 is actively processing another command, the sensor 110 will respond with a standard error response indicating that the sensor 110 is busy. Otherwise, the sensor 110 sends a response as the command is received. Additionally, the sensor 110 sends a success notification through the sensor control characteristic to acknowledge the sensor 110 has received the command. The sensor 110 registers the shutdown command. At the next appropriate opportunity (e.g., depending on the current sensor state, as described herein), the sensor 110 will shut down.

L. Exemplary Sensor States and Activation

Figure 15:
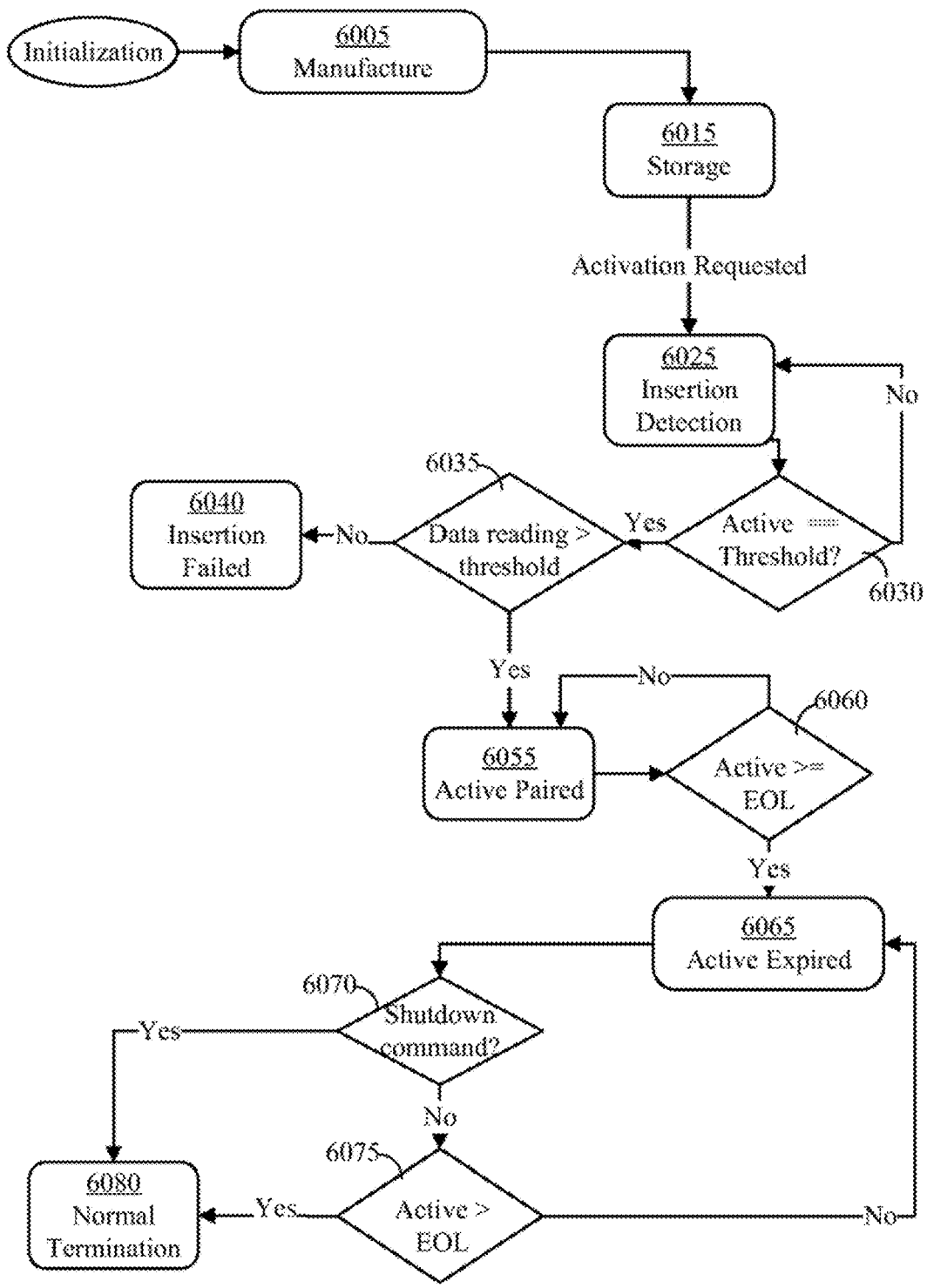
FIG. 15 is a diagram illustrating example operational states of the sensor according to exemplary embodiments of the disclosed subject matter.

For purpose of illustration and not limitation, reference is made to the exemplary embodiment of a high-level depiction of a state machine representation 6000 of the actions that can be taken by the sensor 110 as shown in FIG. 15. After initialization, the sensor enters state 6005, which relates to the manufacture of the sensor 110. In the manufacture state 6005 the sensor 110 can be configured for operation, for example, the storage memory 5030 can be written. At various times while in state 6005, the sensor 110 checks for a received command to go to the storage state 6015. Upon entry to the storage state 6015, the sensor performs a software integrity check. While in the storage state 6015, the sensor can also receive an activation request command before advancing to the insertion detection state 6025.

Upon entry to state 6025, the sensor 110 can store information relating to devices authenticated to communicate with the sensor as set during activation or initialize algorithms related to conducting and interpreting measurements from the sensing hardware 5060. The sensor 110 can also initialize a lifecycle timer, responsible for maintaining an active count of the time of operation of the sensor 110 and begin communication with authenticated devices to transmit recorded data. While in the insertion detection state 6025, the sensor can enter state 6030, where the sensor 110 checks whether the time of operation is equal to a predetermined threshold. This time of operation threshold can correspond to a timeout function for determining whether an insertion has been successful. If the time of operation has reached the threshold, the sensor 110 advances to state 6035, in which the sensor 110 checks whether the average data reading is greater than a threshold amount corresponding to an expected data reading volume for triggering detection of a successful insertion. If the data reading volume is lower than the threshold while in state 6035, the sensor advances to state 6040, corresponding to a failed insertion. If the data reading volume satisfies the threshold, the sensor advances to the active paired state 6055.

The active paired state 6055 of the sensor 110 reflects the state while the sensor 110 is operating as normal by recording measurements, processing the measurements, and reporting them as appropriate. While in the active paired state 6055, the sensor 110 sends measurement results or attempts to establish a connection with a receiving device 120. The sensor 110 also increments the time of operation. Once the sensor 110 reaches a predetermined threshold time of operation (e.g., once the time of operation reaches a predetermined threshold), the sensor 110 transitions to the active expired state 6065. The active expired state 6065 of the sensor 110 reflects the state while the sensor 110 has operated for its maximum predetermined amount of time.

While in the active expired state 6065, the sensor 110 can generally perform operations relating to winding down operation and ensuring that the collected measurements have been securely transmitted to receiving devices as needed. For example, while in the active expired state 6065, the sensor 110 can transmit collected data and, if no connection is available, can increase efforts to discover authenticated devices nearby and establish and connection therewith. While in the active expired state 6065, the sensor 110 can receive a shutdown command at state 6070. If no shutdown command is received, the sensor 110 can also, at state 6075, check if the time of operation has exceeded a final operation threshold. The final operation threshold can be based on the battery life of the sensor 110. The normal termination state 6080 corresponds to the final operations of the sensor 110 and ultimately shutting down the sensor 110.

Before a sensor is activated, the ASIC 5000 resides in a low power storage mode state. The activation process can begin, for example, when an incoming RF field (e.g., NFC field) drives the voltage of the power supply to the ASIC 5000 above a reset threshold, which causes the sensor 110 to enter a wake-up state. While in the wake-up state, the ASIC 5000 enters an activation sequence state. The ASIC 5000 then wakes the communication module 5040. The communication module 5040 is initialized, triggering a power on self-test. The power on self-test can include the ASIC 5000 communicating with the communication module 5040 using a prescribed sequence of reading and writing data to verify the memory and one-time programmable memory are not corrupted.

When the ASIC 5000 enters the measurement mode for the first time, an insertion detection sequence is performed to verify that the sensor 110 has been properly installed onto the patient's body before a proper measurement can take place. First, the sensor 110 interprets a command to activate the measurement configuration process, causing the ASIC 5000 to enter measurement command mode. The sensor 110 then temporarily enters the measurement lifecycle state to run a number of consecutive measurements to test whether the insertion has been successful. The communication module 5040 or ASIC 5000 evaluates the measurement results to determine insertion success. When insertion is deemed successful, the sensor 110 enters a measurement state, in which the sensor 110 begins taking regular measurements using sensing hardware 5060. If the sensor 110 determines that the insertion was not successful, sensor 110 is triggered into an insertion failure mode, in which the ASIC 5000 is commanded back to storage mode while the communication module 5040 disables itself.

M. Exemplary Over-the-Air Updates

Figure 1B:
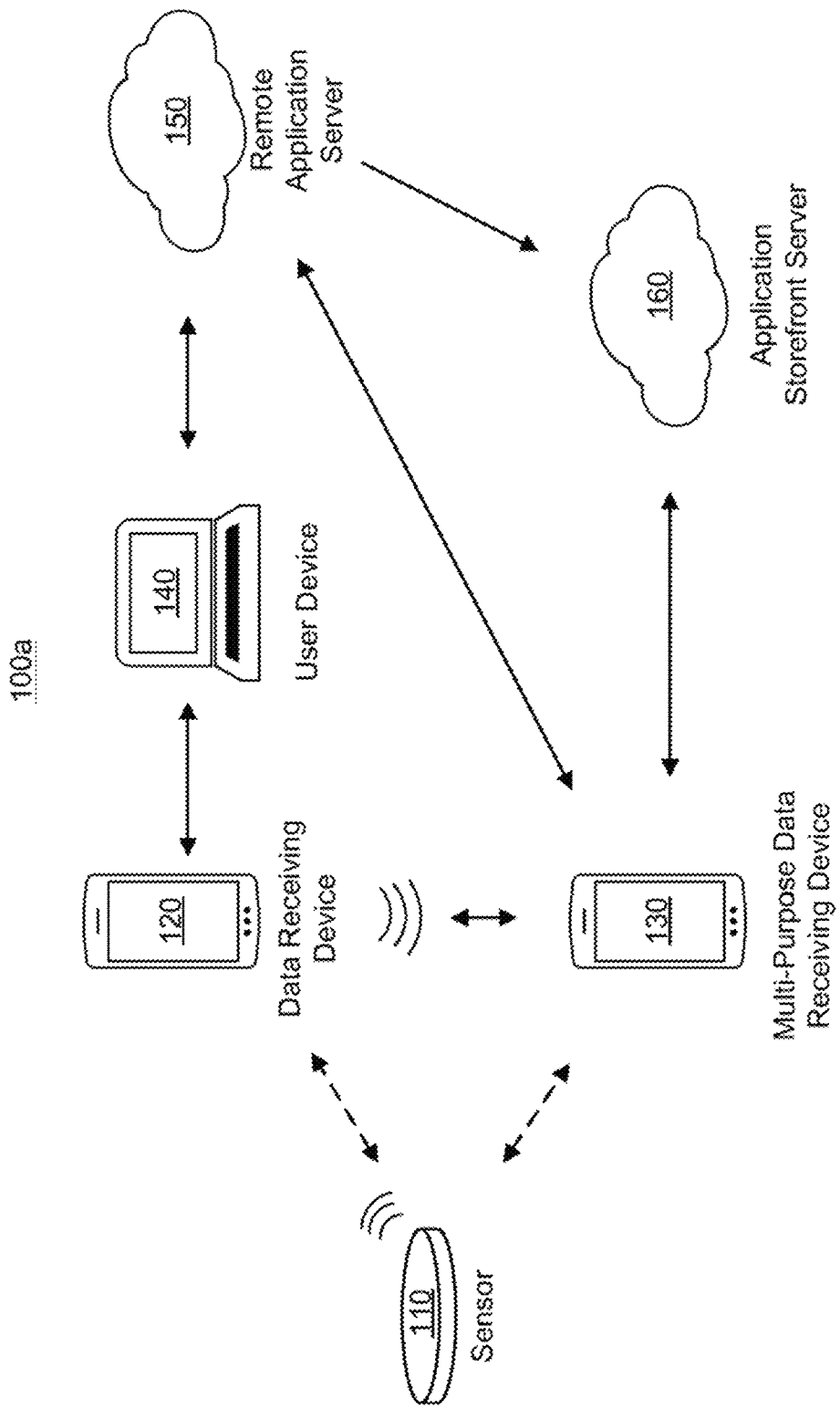
FIG. 1B is a diagram illustrating an operating environment of an example analyte monitoring system for use with the techniques described herein.

FIG. 1B further illustrates an example operating environment for providing over-the-air ("OTA") updates for use with the techniques described herein. An operator of the analyte monitoring system 100 can bundle updates for the data receiving device 120 or sensor 110 into updates for an application executing on the multi-purpose data receiving device 130. Using available communication channels between the data receiving device 120, the multi-purpose data receiving device 130, and the sensor 110, the multi-purpose data receiving device 130 can receive regular updates for the data receiving device 120 or sensor 110 and initiate installation of the updates on the data receiving device 120 or sensor 110. The multi-purpose data receiving device 130 acts as an installation or update platform for the data receiving device 120 or sensor 110 because the application that enables the multi-purpose data receiving device 130 to communicate with an analyte sensor 110, data receiving device 120 and/or remote application server 150 can update software or firmware on a data receiving device 120 or sensor 110 without wide-area networking capabilities.

As embodied herein, a remote application server 150 operated by the manufacturer of the analyte sensor 110 and/or the operator of the analyte monitoring system 100 can provide software and firmware updates to the devices of the analyte monitoring system 100. In particular embodiments, the remote application server 150 can provides the updated software and firmware to a user device 140 or directly to a multi-purpose data receiving device. As embodied herein, the remote application server 150 can also provide application software updates to an application storefront server 160 using interfaces provided by the application storefront. The multi-purpose data receiving device 130 can contact the application storefront server 160 periodically to download and install the updates.

After the multi-purpose data receiving device 130 downloads an application update including a firmware or software update for a data receiving device 120 or sensor 110, the data receiving device 120 or sensor 110 and multi-purpose data receiving device 130 establish a connection. The multi-purpose data receiving device 130 determines that a firmware or software update is available for the data receiving device 120 or sensor 110. The multi-purpose data receiving device 130 can prepare the software or firmware update for delivery to the data receiving device 120 or sensor 110. As an example, the multi-purpose data receiving device 130 can compress or segment the data associated with the software or firmware update, can encrypt or decrypt the firmware or software update, or can perform an integrity check of the firmware or software update. The multi-purpose data receiving device 130 sends the data for the firmware or software update to the data receiving device 120 or sensor 110. The multi-purpose data receiving device 130 can also send a command to the data receiving device 120 or sensor 110 to initiate the update. Additionally or alternatively, the multi-purpose data receiving device 130 can provide a notification to the user of the multi-purpose data receiving device 130 and include instructions for facilitating the update, such as instructions to keep the data receiving device 120 and the multi-purpose data receiving device 130 connected to a power source and in close proximity until the update is complete.

The data receiving device 120 or sensor 110 receives the data for the update and the command to initiate the update from the multi-purpose data receiving device 130. The data receiving device 120 can then install the firmware or software update. To install the update, the data receiving device 120 or sensor 110 can place or restart itself in a so-called "safe" mode with limited operational capabilities. Once the update is completed, the data receiving device 120 or sensor 110 re-enters or resets into a standard operational mode. The data receiving device 120 or sensor 110 can perform one or more self-tests to determine that the firmware or software update was installed successfully. The multi-purpose data receiving device 130 can receive the notification of the successful update. The multi-purpose data receiving device 130 can then report a confirmation of the successful update to the remote application server 150.

In particular embodiments, the storage memory 5030 of the sensor 110 includes one-time programmable (OTP) memory. The term OTP memory can refer to memory that includes access restrictions and security to facilitate writing to particular addresses or segments in the memory a predetermined number of times. The memory 5030 can be prearranged into multiple pre-allocated memory blocks or containers. The containers are pre-allocated into a fixed size. If storage memory 5030 is one-time programming memory, the containers can be considered to be in a non-programmable state. Additional containers which have not yet been written to can be placed into a programmable or writable state. Containerizing the storage memory 5030 in this fashion can improve the transportability of code and data to be written to the storage memory 5030. Updating the software of a device (e.g., the sensor device described herein) stored in an OTP memory can be performed by superseding only the code in a particular previously-written container or containers with updated code written to a new container or containers, rather than replacing the entire code in the memory. In a second embodiment, the memory is not prearranged. Instead, the space allocated for data is dynamically allocated or determined as needed. Incremental updates can be issued, as containers of varying sizes can be defined where updates are anticipated.

Figure 16:
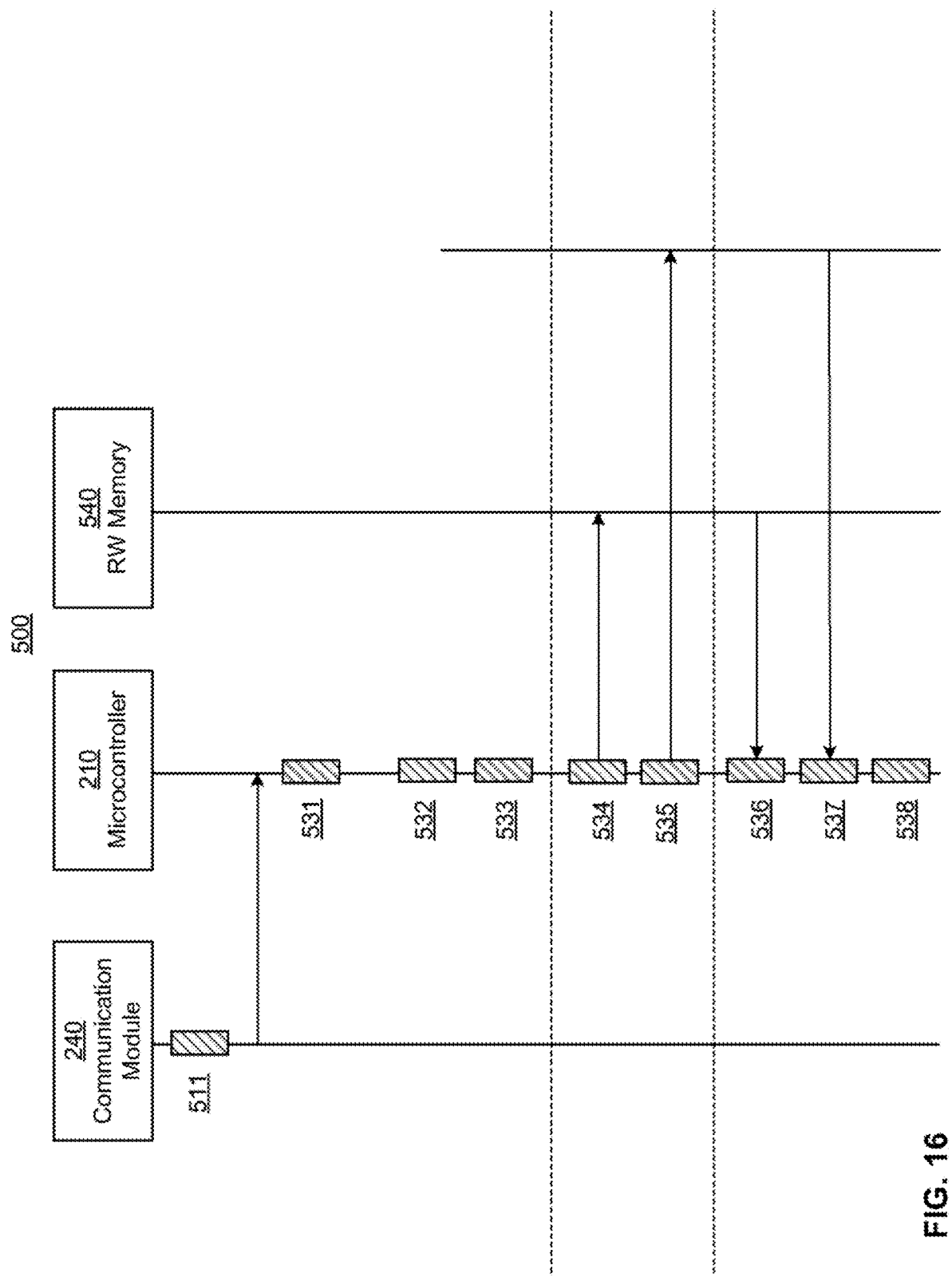
FIG. 16 is a diagram illustrating an example operational and data flow for over-the-air programming of a sensor according to the disclosed subject matter.

FIG. 16 is a diagram illustrating an example operational and data flow for over-the-air (OTA) programming of a storage memory 5030 in a sensor device 100 as well as use of the memory after the OTA programming in execution of processes by the sensor device 110 according to the disclosed subject matter. In the example OTA programming 500 illustrated in FIG. 5, a request is sent from an external device (e.g., the data receiving device 130) to initiate OTA programming (or re-programming). At 511, a communication module 5040 of a sensor device 110 receives an OTA programming command. The communication module 5040 sends the OTA programming command to the microcontroller 5010 of the sensor device 110.

At 531, after receiving the OTA programming command, the microcontroller 5010 validates the OTA programming command. The microcontroller 5010 can determine, for example, whether the OTA programming command is signed with an appropriate digital signature token. Upon determining that the OTA programming command is valid, the microcontroller 5010 can set the sensor device into an OTA programming mode. At 532, the microcontroller 5010 can validate the OTA programming data. At 533, The microcontroller 5010 can reset the sensor device 110 to re-initialize the sensor device 110 in a programming state. Once the sensor device 110 has transitioned into the OTA programming state, the microcontroller 5010 can begin to write data to the rewriteable memory 540 (e.g., memory 5020) of the sensor device at 534 and write data to the OTP memory 550 of the sensor device at 535 (e.g., storage memory 5030). The data written by the microcontroller 5010 can be based on the validated OTA programming data. The microcontroller 5010 can write data to cause one or more programming blocks or regions of the OTP memory 550 to be marked invalid or inaccessible. The data written to the free or unused portion of the OTP memory can be used to replace invalidated or inaccessible programming blocks of the OTP memory 550. After the microcontroller 5010 writes the data to the respective memories at 534 and 535, the microcontroller 5010 can perform one or more software integrity checks to ensure that errors were not introduced into the programming blocks during the writing process. Once the microcontroller 5010 is able to determine that the data has been written without errors, the microcontroller 5010 can resume standard operations of the sensor device.

In execution mode, at 536, the microcontroller 5010 can retrieve a programming manifest or profile from the rewriteable memory 540. The programming manifest or profile can include a listing of the valid software programming blocks and can include a guide to program execution for the sensor 110. By following the programming manifest or profile, the microcontroller 5010 can determine which memory blocks of the OTP memory 550 are appropriate to execute and avoid execution of out-of-date or invalidated programming blocks or reference to out-of-date data. At 537, the microcontroller 5010 can selectively retrieve memory blocks from the OTP memory 550. At 538, the microcontroller 5010 can use the retrieved memory blocks, by executing programming code stored or using variable stored in the memory.

N. Exemplary Security and Other Architecture Features

As embodied herein a first layer of security for communications between the analyte sensor 110 and other devices can be established based on security protocols specified by and integrated in the communication protocols used for the communication. Another layer of security can be based on communication protocols that necessitate close proximity of communicating devices. Furthermore, certain packets and/or certain data included within packets can be encrypted while other packets and/or data within packets is otherwise encrypted or not encrypted. Additionally or alternatively, application layer encryption can be used with one or more block ciphers or stream ciphers to establish mutual authentication and communication encryption with other devices in the analyte monitoring system 100.

The ASIC 5000 of the analyte sensor 110 can be configured to dynamically generate authentication and encryption keys using data retained within the storage memory 5030. The storage memory 5030 can also be pre-programmed with a set of valid authentication and encryption keys to use with particular classes of devices. The ASIC 5000 can be further configured to perform authentication procedures with other devices using received data and apply the generated key to sensitive data prior to transmitting the sensitive data. The generated key can be unique to the analyte sensor 110, unique to a pair of devices, unique to a communication session between an analyte sensor 110 and other device, unique to a message sent during a communication session, or unique to a block of data contained within a message.

Both the sensor 110 and a data receiving device 120 can ensure the authorization of the other party in a communication session to, for example, issue a command or receive data. In particular embodiments, identity authentication can be performed through two features. First, the party asserting its identity provides a validated certificate signed by the manufacturer of the device or the operator of the analyte monitoring system 100. Second, authentication can be enforced through the use of public keys and private keys, and shared secrets derived therefrom, established by the devices of the analyte monitoring system 100 or established by the operator of the analyte monitoring system 100. To confirm the identity of the other party, the party can provide proof that the party has control of its private key.

The manufacturer of the analyte sensor 110, data receiving device 120, or provider of the application for multi-purpose data receiving device 130 can provide information and programming necessary for the devices to securely communicate through secured programming and updates. For example, the manufacturer can provide information that can be used to generate encryption keys for each device, including secured root keys for the analyte sensor 110 and optionally for the data receiving device 120 that can be used in combination with device-specific information and operational data (e.g., entropy-based random values) to generate encryption values unique to the device, session, or data transmission as need.

Analyte data associated with a user is sensitive data at least in part because this information can be used for a variety of purposes, including for health monitoring and medication dosing decisions. In addition to user data, the analyte monitoring system 100 can enforce security hardening against efforts by outside parties to reverse-engineering. Communication connections can be encrypted using a device-unique or session-unique encryption key. Encrypted communications or unencrypted communications between any two devices can be verified with transmission integrity checks built into the communications. Analyte sensor 110 operations can be protected from tampering by restricting access to mad and write functions to the memory 5020 via a communication interface. The sensor can be configured to grant access only to known or "trusted" devices, provided in a "whitelist" or only to devices that can provide a predetermined code associated with the manufacturer or an otherwise authenticated user. A whitelist can represent an exclusive range, meaning that no connection identifiers besides those included in the whitelist will be used, or a preferred range, in which the whitelist is searched first, but other devices can still be used. The sensor 110 can further deny and shut down connection requests if the requestor cannot complete a login procedure over a communication interface within a predetermined period of time (e.g., within four seconds). These characteristics safeguard against specific denial of service attacks, and in particular against denial of service attacks on a BLE interface.

As embodied herein, the analyte monitoring system 100 can employ periodic key rotation to further reduce the likelihood of key compromise and exploitation. A key rotation strategy employed by the analyte monitoring system 100 can be designed to support backward compatibility of field-deployed or distributed devices. As an example, the analyte monitoring system 100 can employ keys for downstream devices (e.g., devices that are in the field or cannot be feasibly provided updates) that are designed to be compatible with multiple generations of keys used by upstream devices.

Figure 17:
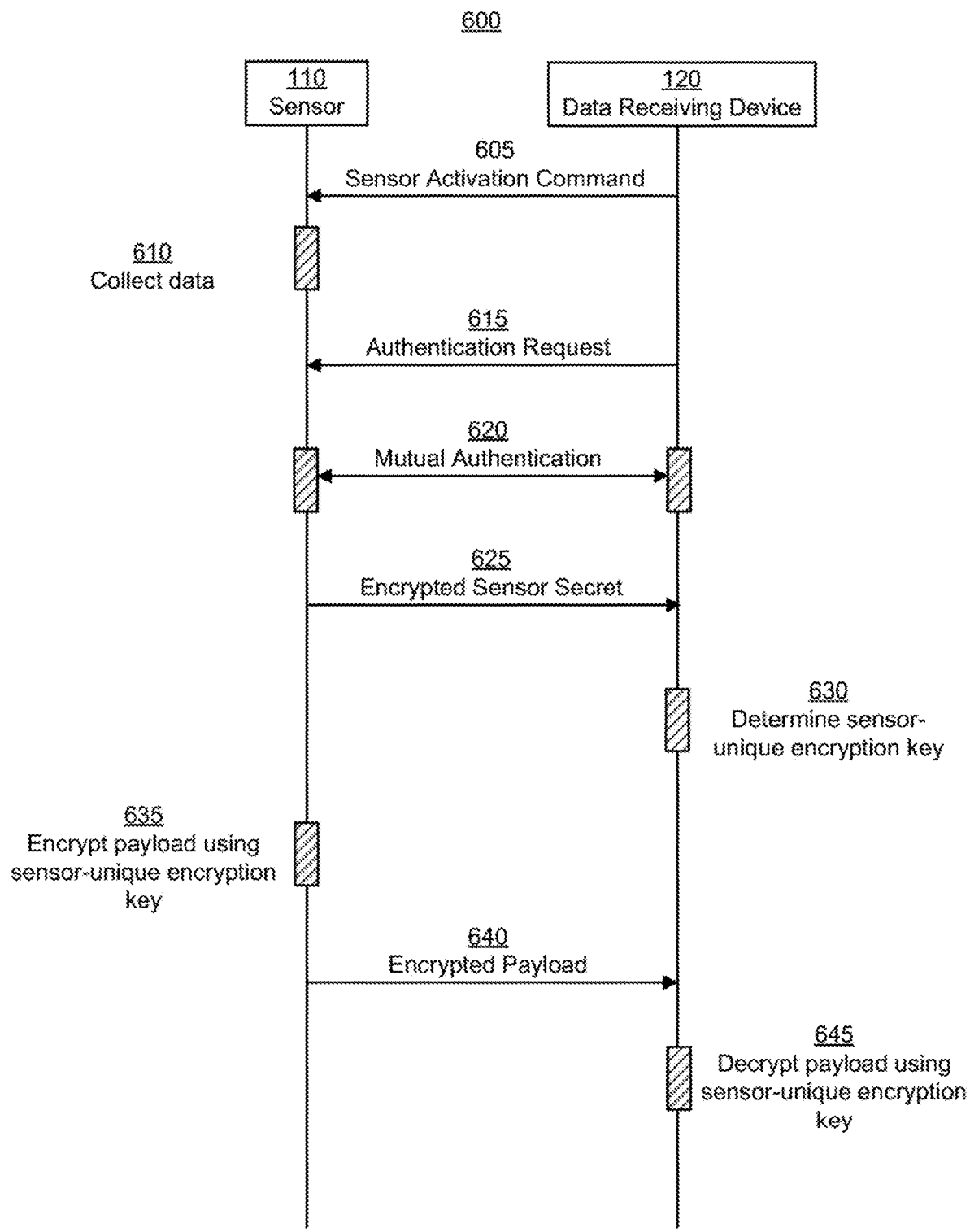
FIG. 17 is a diagram illustrating an example data flow for secure exchange of data between two devices according to the disclosed subject matter.

For purpose of illustration and not limitation, reference is made to the exemplary embodiment of a message sequence diagram 600 for use with the disclosed subject matter as shown in FIG. 17 and demonstrating an example exchange of data between a pair of devices, particularly a sensor 110 and a data receiving device 120. The data receiving device 120 can, as embodied herein, be a data receiving device 120 or a multi-purpose data receiving device 130. At step 605, the data receiving device 120 can transmit a sensor activation command 605 to the sensor 110, for example via a short-range communication protocol. The sensor 110 can, prior to step 605 be in a primarily dormant state, preserving its battery until full activation is needed. After activation during step 610, the sensor 110 can collect data or perform other operations as appropriate to the sensing hardware 5060 of the sensor 110. At step 615 the data receiving device 120 can initiate an authentication request command 615. In response to the authentication request command 615, both the sensor 110 and data receiving device 120 can engage in a mutual authentication process 620. The mutual authentication process 620 can involve the transfer of data, including challenge parameters that allow the sensor 110 and data receiving device 120 to ensure that the other device is sufficiently capable of adhering to an agreed-upon security framework described herein. Mutual authentication can be based on mechanisms for authentication of two or more entities to each other with or without on-line trusted third parties to verify establishment of a secret key via challenge-response. Mutual authentication can be performed using two-, three-, four-, or five-pass authentication, or similar versions thereof.

Following a successful mutual authentication process 620, at step 625 the sensor 110 can provide the data receiving device 120 with a sensor secret 625. The sensor secret can contain sensor-unique values and be derived from random values generated during manufacture. The sensor secret can be encrypted prior to or during transmission to prevent third-parties from accessing the secret. The sensor secret 625 can be encrypted via one or more of the keys generated by or in response to the mutual authentication process 620. At step 630, the data receiving device 120 can derive a sensor-unique encryption key from the sensor secret. The sensor-unique encryption key can further be session-unique. As such, the sensor-unique encryption key can be determined by each device without being transmitted between the sensor 110 or data receiving device 120. At step 635, the sensor 110 can encrypt data to be included in payload. At step 640, the sensor 110 can transmit the encrypted payload 640 to the data receiving device 120 using the communication link established between the appropriate communication models of the sensor 110 and data receiving device 120. At step 645, the data receiving device 120 can decrypt the payload using the sensor-unique encryption key derived during step 630. Following step 645, the sensor 110 can deliver additional (including newly collected) data and the data receiving device 120 can process the received data appropriately.

As discussed herein, the sensor 110 can be a device with restricted processing power, battery supply, and storage. The encryption techniques used by the sensor 110 (e.g., the cipher algorithm or the choice of implementation of the algorithm) can be selected based at least in part on these restrictions. The data receiving device 120 can be a more powerful device with fewer restrictions of this nature. Therefore, the data receiving device 120 can employ more sophisticated, computationally intense encryption techniques, such as cipher algorithms and implementations.

O. Exemplary Payload/Communication Frequencies

The analyte sensor 110 can be configured to alter its discoverability behavior to attempt to increase the probability of the receiving device receiving an appropriate data packet and/or provide an acknowledgement signal or otherwise reduce restrictions that can be causing an inability to receive an acknowledgement signal. Altering the discoverability behavior of the analyte sensor 110 can include, for example and without limitation, altering the frequency at which connection data is included in a data packet, altering how frequently data packets are transmitted generally, lengthening or shortening the broadcast window for data packets, altering the amount of time that the analyte sensor 110 listens for acknowledgement or scan signals after broadcasting, including directed transmissions to one or more devices (e.g., through one or more attempted transmissions) that have previously communicated with the analyte sensor 110 and/or to one or more devices on a whitelist, altering a transmission power associated with the communication module when broadcasting the data packets (e.g., to increase the range of the broadcast or decrease energy consumed and extend the life of the battery of the analyte sensor), altering the rate of preparing and broadcasting data packets, or a combination of one or more other alterations. Additionally, or alternatively, the receiving device can similarly adjust parameters relating to the listening behavior of the device to increase the likelihood of receiving a data packet including connection data.

As embodied herein, the analyte sensor 110 can be configured to broadcast data packets using two types of windows. The first window refers to the rate at which the analyte sensor 110 is configured to operate the communication hardware. The second window refers to the rate at which the analyte sensor 110 is configured to be actively transmitting data packets (e.g., broadcasting). As an example, the first window can indicate that the analyte sensor 110 operates the communication hardware to send and/or receive data packets (including connection data) during the first 2 seconds of each 60 second period. The second window can indicate that, during each 2 second window, the analyte sensor 110 transmits a data packet every 60 milliseconds. The rest of the time during the 2 second window, the analyte sensor 110 is scanning. The analyte sensor 110 can lengthen or shorten either window to modify the discoverability behavior of the analyte sensor 110.

In particular embodiments, the discoverability behavior of the analyte sensor can be stored in a discoverability profile, and alterations can be made based on one or more factors, such as the status of the analyte sensor 110 and/or by applying rules based on the status of the analyte sensor 110. For example, when the battery level of the analyte sensor 110 is below a certain amount, the rules can cause the analyte sensor 110 to decrease the power consumed by the broadcast process. As another example, configuration settings associated with broadcasting or otherwise transmitting packets can be adjusted based on the ambient temperature, the temperature of the analyte sensor 110, or the temperature of certain components of communication hardware of the analyte sensor 110. In addition to modifying the transmission power, other parameters associated with the transmission capabilities or processes of the communication hardware of the analyte sensor 110 can be modified, including, but not limited to, transmission rate, frequency, and timing. As another example, when the analyte data indicates that the subject is, or is about to be, experiencing a negative health event, the rules can cause the analyte sensor 110 to increase its discoverability to alert the receiving device of the negative health event.

P. Exemplary Sensor Sensitivity Initialization/Adjustment Features

As embodied herein, certain calibration features for the sensing hardware 5060 of the analyte sensor 110 can be adjusted based on external or interval environment features as well as to compensate for the decay of the sensing hardware 5060 during expended period of disuse (e.g., a "shelf time" prior to use). The calibration features of the sensing hardware 5060 can be autonomously adjusted by the sensor 110 (e.g., by operation of the ASIC 5000 to modify features in the memory 5020 or storage 5030) or can be adjusted by other devices of the analyte monitoring system 100.

As an example, sensor sensitivity of the sensing hardware 5060 can be adjusted based on external temperature data or the time since manufacture. When external temperatures are monitored during the storage of the sensors, the disclosed subject matter can adaptively change the compensation to sensor sensitivity over time when the device experiences changing storage conditions. For purpose of illustration not limitations, adaptive sensitivity adjustment can be performed in an "active" storage mode where the analyte sensor 110 wakes up periodically to measure temperature. These features can save the battery of the analyte device and extend the lifespan of the analyte sensors. At each temperature measurement, the analyte sensor 110 can calculate a sensitivity adjustment for that time period based on the measured temperature. Then, the temperature-weighted adjustments can be accumulated over the active storage mode period to calculate a total sensor sensitivity adjustment value at the end of the active storage mode (e.g., at insertion). Similarly, at insertion, the sensor 110 can determine the time difference between manufacture of the sensor 110 (which can be written to the storage 5030 of the ASIC 5000) or the sensing hardware 5060 and modify sensor sensitivity or other calibration features according to one or more known decay rates or formulas.

Additionally, for purpose of illustration and not limitation, as embodied herein, sensor sensitivity adjustments can account for other sensor conditions, such as sensor drift. Sensor sensitivity adjustments can be hardcoded into the sensor 110 during manufacture, for example in the case of sensor drift, based on an estimate of how much an average sensor would drift. Sensor 110 can use a calibration function that has time-varying functions for sensor offset and gain, which can account for drift over a wear period of the sensor. Thus, sensor 110 can utilize a function used to transform an interstitial current to interstitial glucose utilizing device-dependent functions describing sensor 110 drift over time, and which can represent sensor sensitivity, and can be device specific, combined with a baseline of the glucose profile. Such functions to account for sensor sensitivity and drift can improve sensor 110 accuracy over a wear period and without involving user calibration.

Q. Exemplary Model-Based Analyte Measurements

The sensor 110 detects raw measurement values from sensing hardware 5060. On-sensor processing can be performed, such as by one or more models trained to interpret the raw measurement values. Models can be machine learned models trained off-device to detect, predict, or interpret the raw measurement values to detect, predict, or interpret the levels of one or more analytes. Additional trained models can operate on the output of the machine learning models trained to interact with raw measurement values. As an example, models can be used to detect, predict, or recommend events based on the raw measurements and type of analyte(s) detected by the sensing hardware 5060. Events can include, initiation or completion of physical activity, meals, application of medical treatment or medication, emergent health events, and other events of a similar nature.

Models can be provided to the sensor 110, data receiving device 120, or multi-purpose data receiving device 130 during manufacture or during firmware or software updates. Models can be periodically refined, such as by the manufacturer of the sensor 110 or the operator of the analyte monitoring system 100, based on data received from the sensor 110 and data receiving devices of an individual user or multiple users collectively. In certain embodiments, the sensor 110 includes sufficient computational components to assist with further training or refinement of the machine learned models, such as based on unique features of the user to which the sensor 110 is attached. Machine learning models can include, by way of example and not limitation, models trained using or encompassing decision tree analysis, gradient boosting, ada boosting, artificial neural networks or variants thereof, linear discriminant analysis, nearest neighbor analysis, support vector machines, supervised or unsupervised classification, and others. The models can also include algorithmic or rules-based models in addition to machine learned models. Model-based processing can be performed by other devices, including the data receiving device 120 or multi-purpose data receiving device 130, upon receiving data from the sensor 110 (or other downstream devices).

R. Exemplary Alarm Features

Data transmitted between the sensor 110 and a data receiving device 120 can include raw or processed measurement values. Data transmitted between the sensor 110 and data receiving device 120 can further include alarms or notification for display to a user. The data receiving device 120 can display or otherwise convey notifications to the user based on the raw or processed measurement values or can display alarms when received from the sensor 110. Alarms that may be triggered for display to the user include alarms based on direct analyte values (e.g., one-time reading exceeding a threshold or failing to satisfy a threshold), analyte value trends (e.g., average reading over a set period of time exceeding a threshold or failing to satisfy a threshold; slope); analyte value predictions (e.g., algorithmic calculation based on analyte values exceeds a threshold or fails to satisfy a threshold), sensor alerts (e.g., suspected malfunction detected), communication alerts (e.g., no communication between sensor 110 and data receiving device 120 for a threshold period of time; unknown device attempting or failing to initiate a communication session with the sensor 110), reminders (e.g., reminder to charge data receiving device 120; reminder to take a medication or perform other activity), and other alerts of a similar nature. For purpose of illustration and not limitation, as embodied herein, the alarm parameters described herein can be configurable by a user or can be fixed during manufacture, or combinations of user-settable and non-user-settable parameters.

S. Exemplary Electrode Configurations

Figure 18A:
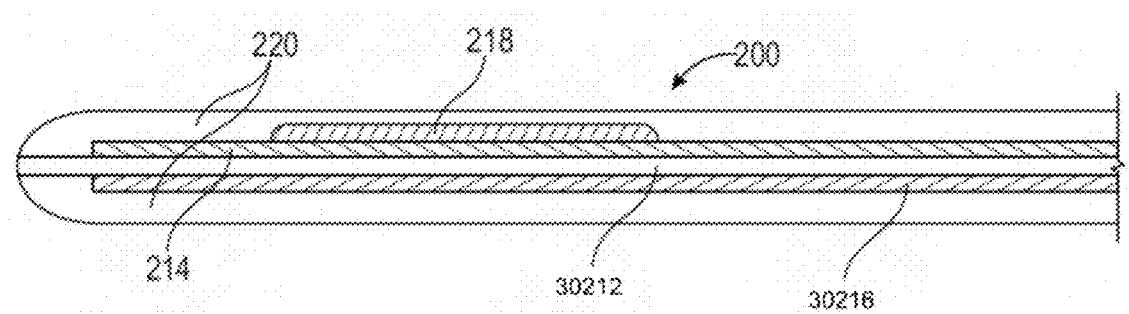
FIGS. 18A-18C show cross-sectional diagrams of analyte sensors including a single active area.
Figure 18B:
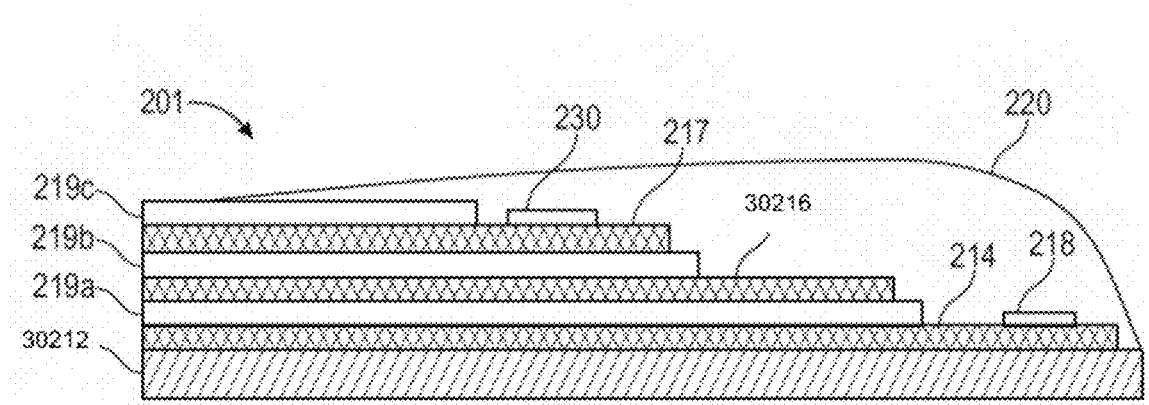
Figure 18C:
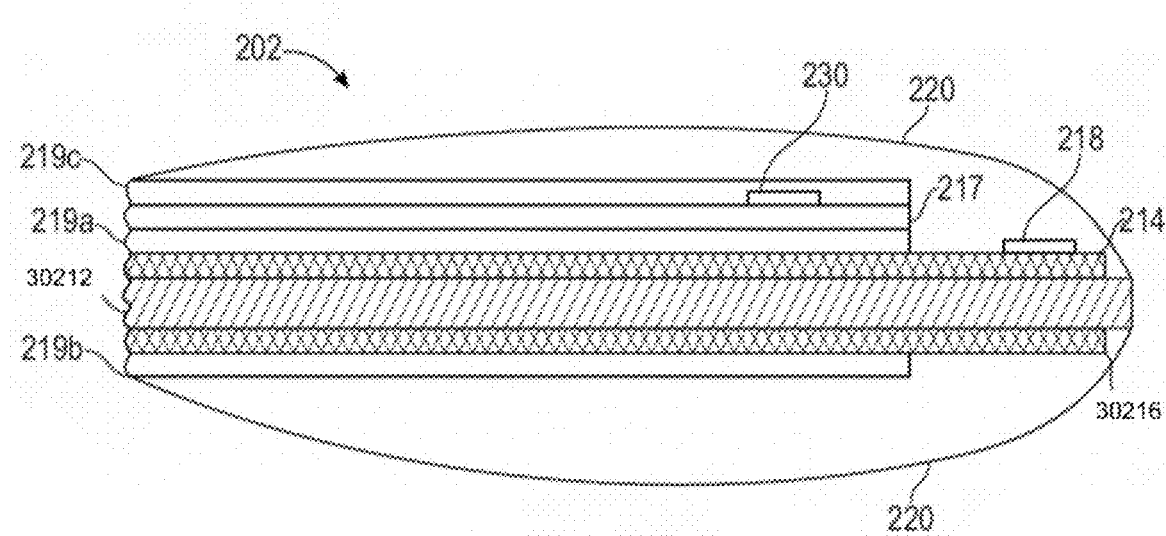

Sensor configurations featuring a single active area that is configured for the detection of a corresponding single analyte can employ two-electrode or three-electrode detection motifs, as described further herein in reference to FIGS. 18A-18C. Sensor configurations featuring two different active areas for detection of the same or separate analytes, either upon separate working electrodes or upon the same working electrode, are described separately thereafter in reference to FIGS. 19A-21C. Sensor configurations having multiple working electrodes can be particularly advantageous for incorporating two different active areas within the same sensor tail, since the signal contribution from each active area can be determined readily.

When a single working electrode is present in an analyte sensor, three-electrode sensor configurations can include a working electrode, a counter electrode, and a reference electrode. Related two-electrode sensor configurations can include a working electrode and a second electrode, in which the second electrode can function as both a counter electrode and a reference electrode (i.e., a counter/reference electrode). The various electrodes can be at least partially stacked (layered) upon one another and/or laterally spaced apart from one another upon the sensor tail. Suitable sensor configurations can be substantially flat in shape, substantially cylindrical in shape or any suitable shape. In any of the sensor configurations disclosed herein, the various electrodes can be electrically isolated from one another by a dielectric material or similar insulator.

Analyte sensors featuring multiple working electrodes can similarly include at least one additional electrode. When one additional electrode is present, the one additional electrode can function as a counter/reference electrode for each of the multiple working electrodes. When two additional electrodes are present, one of the additional electrodes can function as a counter electrode for each of the multiple working electrodes and the other of the additional electrodes can function as a reference electrode for each of the multiple working electrodes.

FIG. 18A shows a diagram of an illustrative two-electrode analyte sensor configuration, which is compatible for use in the disclosure herein. As shown, analyte sensor 200 includes substrate 30212 disposed between working electrode 214 and counter/reference electrode 30216. Alternately, working electrode 214 and counter/reference electrode 30216 can be located upon the same side of substrate 30212 with a dielectric material interposed in between (configuration not shown). Active area 218 is disposed as at least one layer upon at least a portion of working electrode 214. Active area 218 can include multiple spots or a single spot configured for detection of an analyte, as discussed further herein. In certain embodiments, active area 218 is configured to detect aspartate and/or asparagine as described herein.

Referring still to FIG. 18A, membrane 220 overcoats at least active area 218. In certain embodiments, membrane 220 can also overcoat some or all of working electrode 214 and/or counter/reference electrode 30216, or the entirety of analyte sensor 200. One or both faces of analyte sensor 200 can be overcoated with membrane 220. Membrane 220 can include one or more polymeric membrane materials having capabilities of limiting analyte flux to active area 218 (i.e., membrane 220 is a mass transport limiting membrane having some permeability for the analyte of interest). According to the disclosure herein, and further described below, membrane 220 can be crosslinked with a branched crosslinker in certain particular sensor configurations. For example, but not by way of limitation, membrane 220 is crosslinked with a crosslinking agent described herein. The composition and thickness of membrane 220 can vary to promote a desired analyte flux to active area 218, thereby providing a desired signal intensity and stability. Analyte sensor 200 can be operable for assaying an analyte by any of coulometric, amperometric, voltammetric, or potentiometric electrochemical detection techniques.

FIGS. 18B and 18C show diagrams of illustrative three-electrode analyte sensor configurations, which are also compatible for use in the disclosure herein. Three-electrode analyte sensor configurations can be similar to that shown for analyte sensor 200 in FIG. 18A, except for the inclusion of additional electrode 217 in analyte sensors 201 and 202 (FIGS. 18B and 18C). With additional electrode 217, counter/reference electrode 30216 can then function as either a counter electrode or a reference electrode, and additional electrode 217 fulfills the other electrode function not otherwise accounted for. Working electrode 214 continues to fulfill its original function. Additional electrode 217 can be disposed upon either working electrode 214 or electrode 30216, with a separating layer of dielectric material in between. For example, and not by the way of limitation, as depicted in FIG. 18B, dielectric layers 219a, 219b and 219c separate electrodes 214, 30216 and 217 from one another and provide electrical isolation. Alternatively, at least one of electrodes 214, 30216 and 217 can be located upon opposite faces of substrate 30212, as shown in FIG. 18C. Thus, in certain embodiments, electrode 214 (working electrode) and electrode 30216 (counter electrode) can be located upon opposite faces of substrate 30212, with electrode 217 (reference electrode) being located upon one of electrodes 214 or 30216 and spaced apart therefrom with a dielectric material. Reference material layer 230 (e.g., Ag/AgCl) can be present upon electrode 217, with the location of reference material layer 230 not being limited to that depicted in FIGS. 18B and 18C. As with sensor 200 shown in FIG. 18A, active area 218 in analyte sensors 201 and 202 can include multiple spots or a single spot. Additionally, analyte sensors 201 and 202 can be operable for assaying an analyte by any of coulometric, amperometric, voltammetric, or potentiometric electrochemical detection techniques.

Like analyte sensor 200, membrane 220 can also overcoat active area 218, as well as other sensor components, in analyte sensors 201 and 202, thereby serving as a mass transport limiting membrane. In certain embodiments, the additional electrode 217 can be overcoated with membrane 220. Although FIGS. 18B and 18C have depicted electrodes 214, 30216 and 217 as being overcoated with membrane 220, it is to be recognized that in certain embodiments only working electrode 214 is overcoated. Moreover, the thickness of membrane 220 at each of electrodes 214, 30216 and 217 can be the same or different. As in two-electrode analyte sensor configurations (FIG. 18A), one or both faces of analyte sensors 201 and 202 can be overcoated with membrane 220 in the sensor configurations of FIGS. 18B and 18C, or the entirety of analyte sensors 201 and 202 can be overcoated. Accordingly, the three-electrode sensor configurations shown in FIGS. 18B and 18C should be understood as being non-limiting of the embodiments disclosed herein, with alternative electrode and/or layer configurations remaining within the scope of the present disclosure.

Figure 19A:
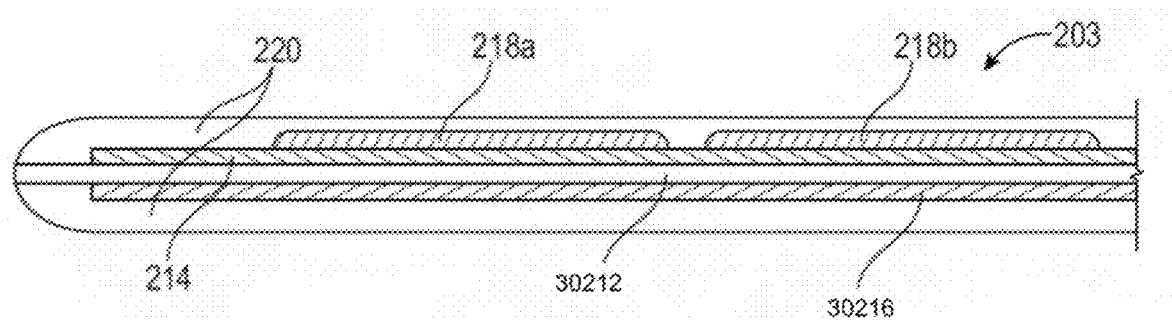
FIGS. 19A-19C show cross-sectional diagrams of analyte sensors including two active areas.

FIG. 19A shows an illustrative configuration for sensor 203 having a single working electrode with two different active areas disposed thereon. FIG. 19A is similar to FIG. 18A, except for the presence of two active areas upon working electrode 214: first active area 218a and second active area 218b, which are responsive to the same or different analytes and are laterally spaced apart from one another upon the surface of working electrode 214. Active areas 218a and 218b can include multiple spots or a single spot configured for detection of each analyte. The composition of membrane 220 can vary or be compositionally the same at active areas 218a and 218b. First active area 218a and second active area 218b can be configured to detect their corresponding analytes at working electrode potentials that differ from one another, as discussed further below.

In certain embodiments, any one of active areas 218a and 218b, or both, can be configured to detect aspartate. In certain embodiments, only one active area of 218a and 218b is configured to detect aspartate. In certain embodiments, the other active area is configured to detect a second analyte that is different from aspartate. In certain embodiments, any one of active areas 218a and 218b, or both, can be configured to detect asparagine. In certain embodiments, only one active area of 218a and 218b is configured to detect asparagine. In certain embodiments, the other active area is configured to detect a second analyte that is different from asparagine. Non-limiting examples of second analytes are described herein. In certain embodiments, one of active areas 218a and 218 is configured to detect aspartate and the other active area is configured to detect asparagine.

Figure 19B:
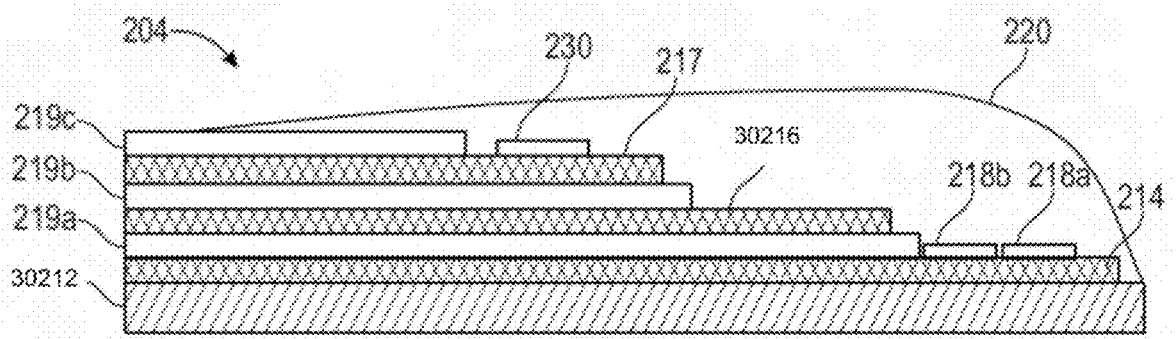
Figure 19C:
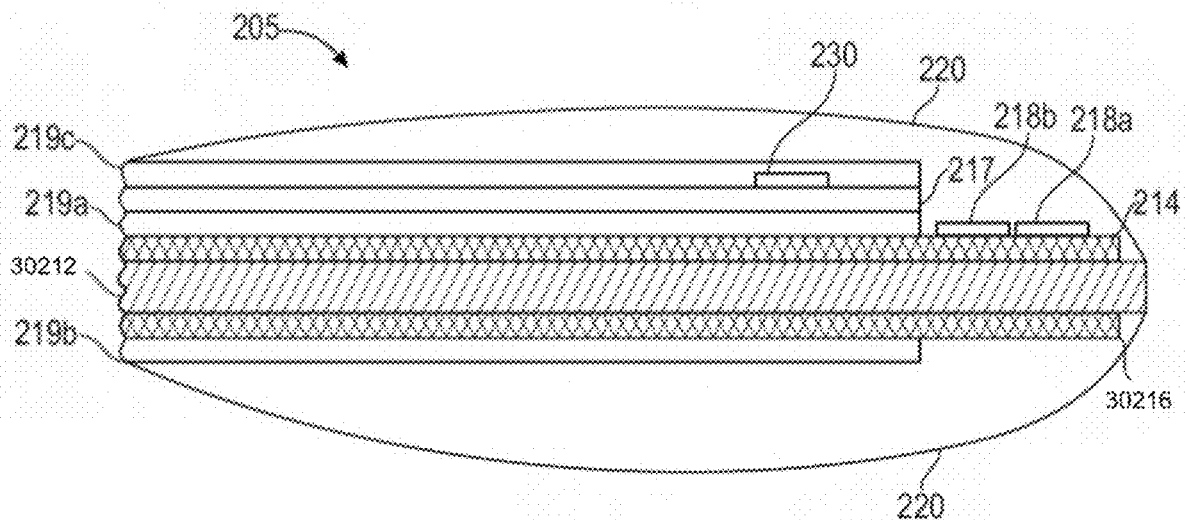

FIGS. 19B and 19C show cross-sectional diagrams of illustrative three-electrode sensor configurations for sensors 204 and 205, respectively, each featuring a single working electrode having first active area 218a and second active area 218b disposed thereon. FIGS. 19B and 19C are otherwise similar to FIGS. 18B and 18C and can be better understood by reference thereto. As with FIG. 19A, the composition of membrane 220 can vary or be compositionally the same at active areas 218a and 218b.

Figure 20:
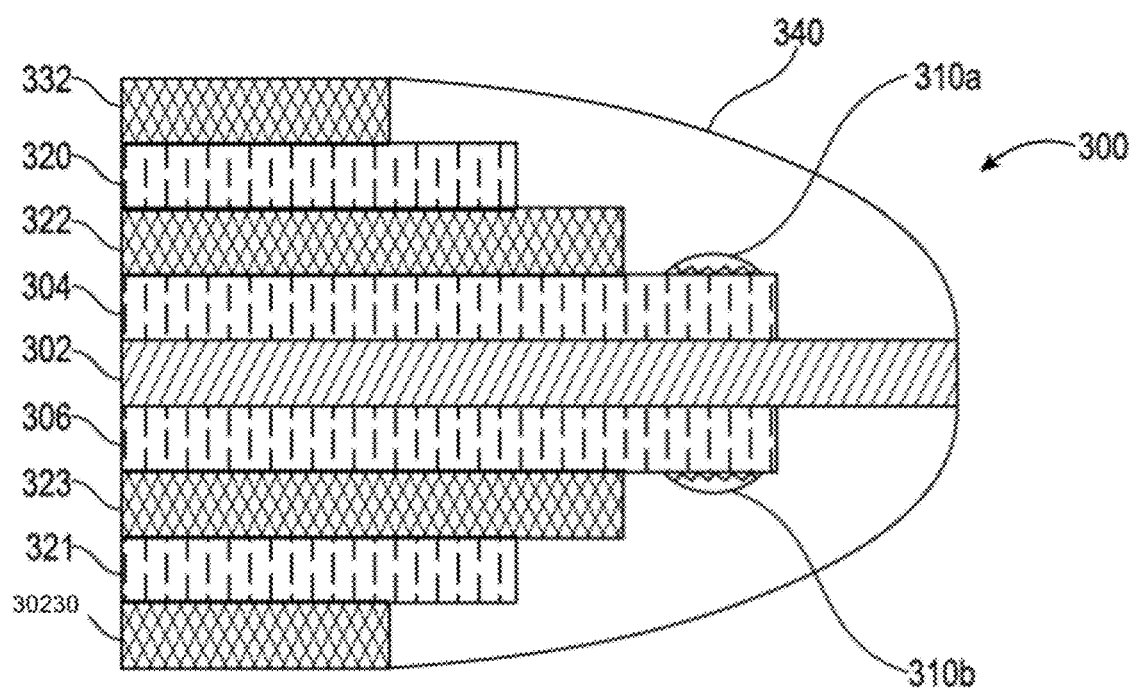
FIG. 20 shows a cross-sectional diagram of an analyte sensor including two active areas.
Figure 21A:
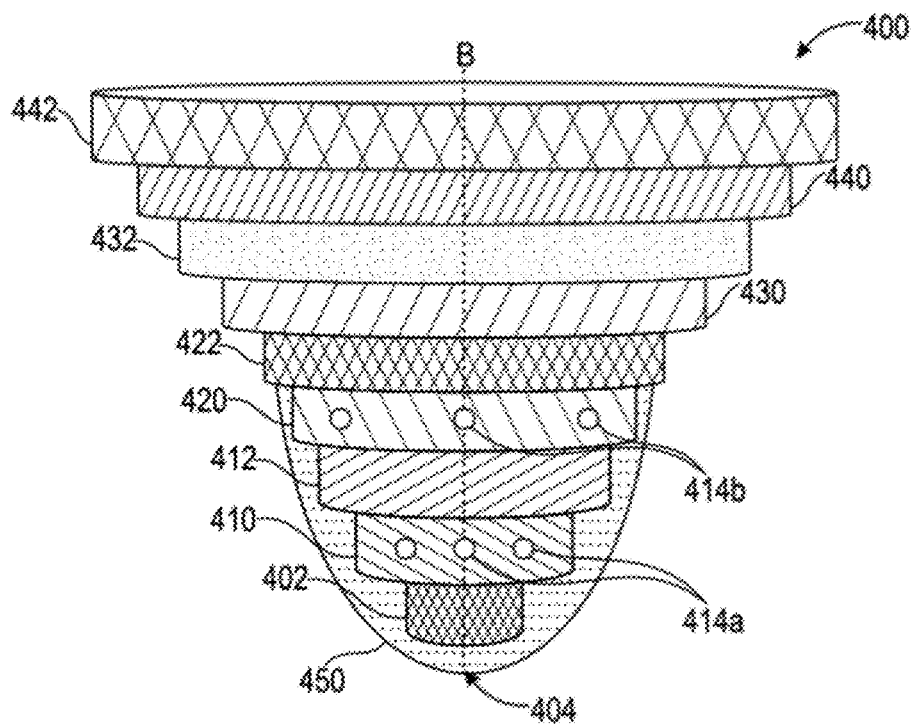
FIGS. 21A-21C show perspective views of analyte sensors including two active areas upon separate working electrodes.
Figure 21B:
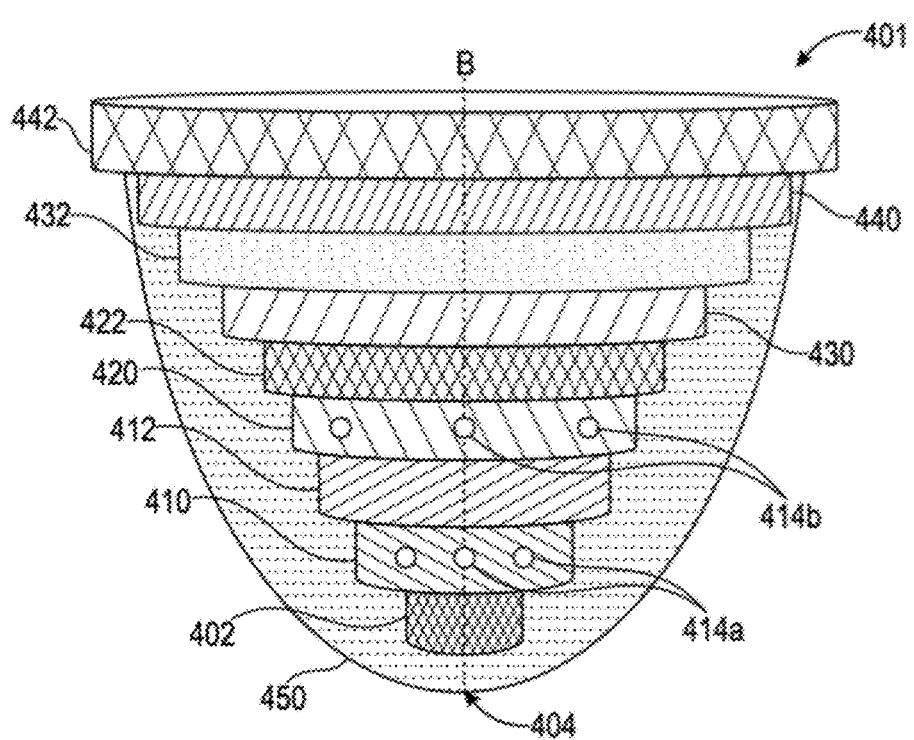
Figure 21C:
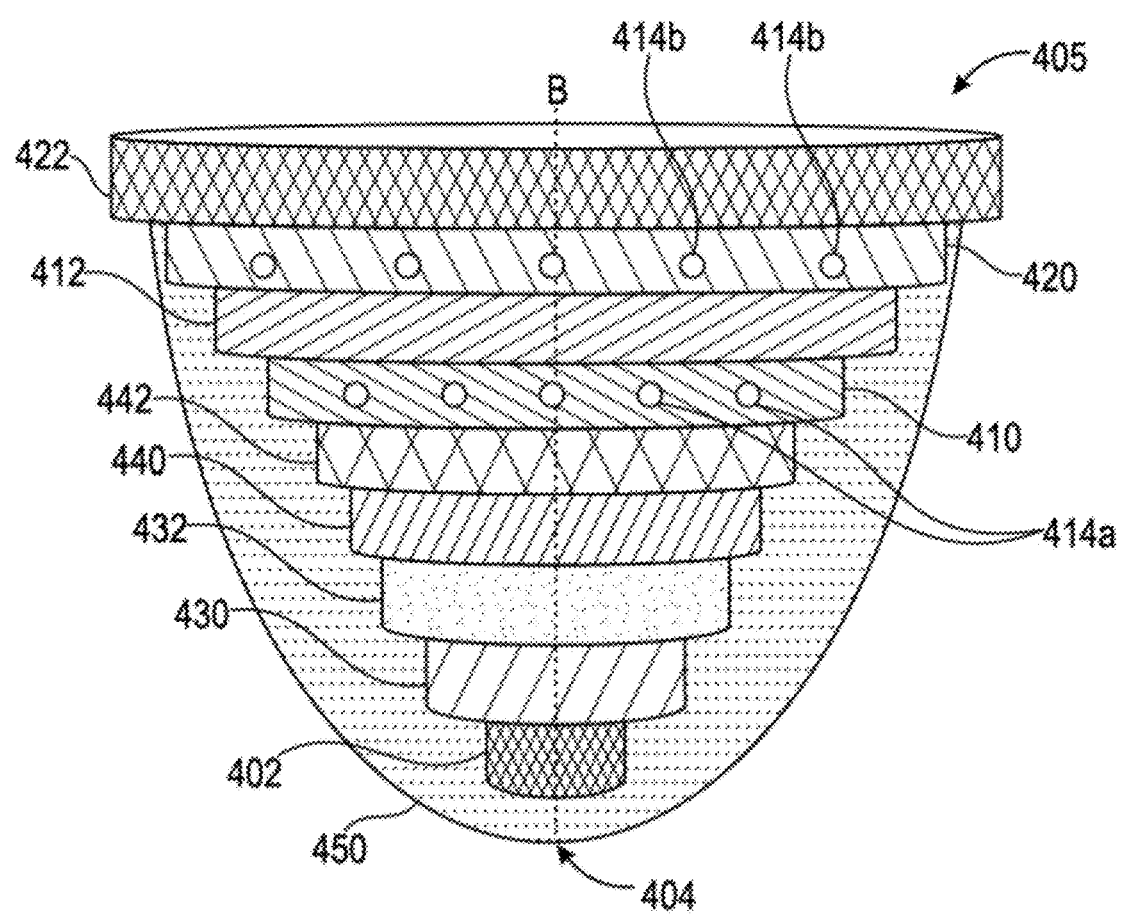

Illustrative sensor configurations having multiple working electrodes, specifically two working electrodes, are described in further detail in reference to FIGS. 20-21C. Although the following description is primarily directed to sensor configurations having two working electrodes, it is to be appreciated that more than two working electrodes can be incorporated through extension of the disclosure herein. Additional working electrodes can be used to impart additional sensing capabilities to the analyte sensors beyond just a first analyte and a second analyte, e.g., for the detection of a third and/or fourth analyte.

FIG. 20 shows a cross-sectional diagram of an illustrative analyte sensor configuration having two working electrodes, a reference electrode and a counter electrode, which is compatible for use in the disclosure herein. As shown, analyte sensor 300 includes working electrodes 304 and 306 disposed upon opposite faces of substrate 302. First active area 310a is disposed upon the surface of working electrode 304, and second active area 310b is disposed upon the surface of working electrode 306. Counter electrode 320 is electrically isolated from working electrode 304 by dielectric layer 322, and reference electrode 321 is electrically isolated from working electrode 306 by dielectric layer 323. Outer dielectric layers 30230 and 332 are positioned upon reference electrode 321 and counter electrode 320, respectively. Membrane 340 can overcoat at least active areas 310a and 310b, according to various embodiments, with other components of analyte sensor 300 or the entirety of analyte sensor 300 optionally being overcoated with membrane 340. Again, membrane 340 can be continuous but vary compositionally within a first membrane portion 340a and a second membrane portion 340b (i.e., upon active areas 310a and 310b) in order to afford different permeability values for differentially regulating the analyte flux at each location. In certain embodiments, different membrane formulations can be sprayed and/or printed onto the opposing faces of analyte sensor 300. For example, but not byway of limitation, a first membrane portion 340a can overcoat at least active area 310a and a second membrane portion 340b can overcoat at least active area 310b, according to various embodiments, with other components of analyte sensor 300 or the entirety of analyte sensor 300. Dip coating techniques can also be appropriate, particularly for depositing at least a portion of a bilayer membrane upon one of active areas 310a and 310b. In certain embodiments, membrane 340 can be the same or vary compositionally at active areas 310a and 310b. For example, but not by way of limitation, membrane 340 can include a bilayer overcoating active area 310a and be a homogeneous membrane overcoating active area 310b, or membrane 340 can include a bilayer overcoating active area 310b and be a homogeneous membrane overcoating active area 310a. In certain embodiments, one of the first membrane portion 340a and the second membrane portion 340b can comprise a bilayer membrane and the other of the first membrane portion 340a and the second membrane portion 340b can comprise a single membrane polymer, according to particular embodiments of the present disclosure. In certain embodiments, an analyte sensor can include more than one membrane 340, e.g., two or more membranes. For example, but not by way of limitation, an analyte sensor can include a membrane that overcoats the one or more active areas, e.g., 310a and 310b, and an additional membrane that overcoats the entire sensor as shown in FIG. 20. In such configurations, a bilayer membrane can be formed over the one or more active areas, e.g., 310a and 310b.

In certain embodiments, any one of active areas 310a and 310b, or both, can be configured to detect aspartate. In certain embodiments, only one active area of 310a and 310b is configured to detect aspartate. In certain embodiments, the other active area is configured to detect a second analyte that is different from aspartate. In certain embodiments, any one of active areas 310a and 310b, or both, can be configured to detect asparagine. In certain embodiments, only one active area of 310a and 310b is configured to detect asparagine. In certain embodiments, the other active area is configured to detect a second analyte that is different from asparagine. Non-limiting examples of second analytes are described herein. In certain embodiments, one of active areas 310a and 310b is configured to detect aspartate and the other active area is configured to detect asparagine.

Like analyte sensors 200, 201 and 202, analyte sensor 300 can be operable for assaying aspartate and/or asparagine by any of coulometric, amperometric, voltammetric, or potentiometric electrochemical detection techniques.

Alternative sensor configurations having multiple working electrodes and differing from the configuration shown in FIG. 20 can feature a counter/reference electrode instead of separate counter and reference electrodes 320, 321, and/or feature layer and/or membrane arrangements varying from those expressly depicted. For example, and not by the way of limitation the positioning of counter electrode 320 and reference electrode 321 can be reversed from that depicted in FIG. 20. In addition, working electrodes 304 and 306 need not necessarily reside upon opposing faces of substrate 302 in the manner shown in FIG. 20.

Although suitable sensor configurations can feature electrodes that are substantially planar in character, it is to be appreciated that sensor configurations featuring non-planar electrodes can be advantageous and particularly suitable for use in the disclosure herein. In particular, substantially cylindrical electrodes that are disposed concentrically with respect to one another can facilitate deposition of a mass transport limiting membrane, as described hereinbelow. FIGS. 21A-21C show perspective views of analyte sensors featuring two working electrodes that are disposed concentrically with respect to one another. It is to be appreciated that sensor configurations having a concentric electrode disposition but lacking a second working electrode are also possible in the present disclosure. In particular, concentric working electrodes that are spaced apart along the length of a sensor tail can facilitate membrane deposition through sequential dip coating operations, in a similar manner to that described above for substantially planar sensor configurations.

FIG. 21A shows a perspective view of an illustrative sensor configuration in which multiple electrodes are substantially cylindrical and are disposed concentrically with respect to one another about a central substrate. As shown, analyte sensor 400 includes central substrate 402 about which all electrodes and dielectric layers are disposed concentrically with respect to one another. In particular, working electrode 410 is disposed upon the surface of central substrate 402, and dielectric layer 412 is disposed upon a portion of working electrode 410 distal to sensor tip 404. Working electrode 420 is disposed upon dielectric layer 412, and dielectric layer 422 is disposed upon a portion of working electrode 420 distal to sensor tip 404. Counter electrode 430 is disposed upon dielectric layer 422, and dielectric layer 432 is disposed upon a portion of counter electrode 430 distal to sensor tip 404. Reference electrode 440 is disposed upon dielectric layer 432, and dielectric layer 442 is disposed upon a portion of reference electrode 440 distal to sensor tip 404. As such, exposed surfaces of working electrode 410, working electrode 420, counter electrode 430, and reference electrode 440 are spaced apart from one another along longitudinal axis B of analyte sensor 400.

Referring still to FIG. 21A, first active areas 414a and second active areas 414b, which are responsive to different analytes or the same analyte, are disposed upon the exposed surfaces of working electrodes 410 and 420, respectively, thereby allowing contact with a fluid to take place for sensing. Although active areas 414*a* and 414*b* have been depicted as three discrete spots in FIG. 21A, it is to be appreciated that fewer or greater than three spots, including a continuous layer of active area, can be present in alternative sensor configurations. In certain embodiments, any one of active areas 414*a* and 414*b*, or both, can be configured to detect aspartate. In certain embodiments, only one active area of 414*a* and 414*b* is configured to detect aspartate. In certain embodiments, the other active area is configured to detect a second analyte that is different from aspartate. In certain embodiments, any one of active areas 414*a* and 414*b*, or both, can be configured to detect asparagine. In certain embodiments, only one active area of 414*a* and 414*b* is configured to detect asparagine. In certain embodiments, the other active area is configured to detect a second analyte that is different from asparagine. Non-limiting examples of second analytes are described herein. In certain embodiments, one of active areas 414*a* and 414*b* is configured to detect aspartate and the other active area is configured to detect asparagine.

In FIG. 21A, sensor 400 is partially coated with membrane 450 upon working electrodes 410 and 420 and active areas 414*a* and 414*b* disposed thereon. FIG. 21B shows an alternative sensor configuration in which the substantial entirety of sensor 401 is overcoated with membrane 450. Membrane 450 can be the same or vary compositionally at active areas 414*a* and 414*b*. For example, membrane 450 can include a bilayer overcoating active areas 414*a* and be a homogeneous membrane overcoating active areas 414*b*.

It is to be further appreciated that the positioning of the various electrodes in FIGS. 21A and 21B can differ from that expressly depicted. For example, the positions of counter electrode 430 and reference electrode 440 can be reversed from the depicted configurations in FIGS. 21A and 21B. Similarly, the positions of working electrodes 410 and 420 are not limited to those that are expressly depicted in FIGS. 21A and 21B. FIG. 21C shows an alternative sensor configuration to that shown in FIG. 21B, in which sensor 405 contains counter electrode 430 and reference electrode 440 that are located more proximal to sensor tip 404 and working electrodes 410 and 420 that are located more distal to sensor tip 404. Sensor configurations in which working electrodes 410 and 420 are located more distal to sensor tip 404 can be advantageous by providing a larger surface area for deposition of active areas 414*a* and 414*b* (five discrete sensing spots illustratively shown in FIG. 21C), thereby facilitating an increased signal strength in some cases. Similarly, central substrate 402 can be omitted in any concentric sensor configuration disclosed herein, wherein the innermost electrode can instead support subsequently deposited layers.

In certain embodiments, one or more electrodes of an analyte sensor described herein is a wire electrode, e.g., a permeable wire electrode. In certain embodiments, the sensor tail comprises a working electrode and a reference electrode helically wound around the working electrode. In certain embodiments, an insulator is disposed between the working and reference electrodes. In certain embodiments, portions of the electrodes are exposed to allow reaction of the one or more enzymes with an analyte on the electrode. In certain embodiments, each electrode is formed from a fine wire with a diameter of from about 0.001 inches or less to about 0.010 inches or more. In certain embodiments, the working electrode has a diameter of from about 0.001 inches or less to about 0.010 inches or more, e.g., from about 0.002 inches to about 0.008 inches, and more preferably from about 0.004 inches to about 0.005 inches. In certain embodiments, an electrode is formed from a plated insulator, a plated wire or bulk electrically conductive material. In certain embodiments, the working electrode comprises a wire formed from a conductive material, such as platinum, platinum-iridium, palladium, graphite, gold, carbon, conductive polymer, alloys or the like. In certain embodiments, the conductive material is a permeable conductive material. In certain embodiments, the electrodes can be formed by a variety of manufacturing techniques (e.g., bulk metal processing, deposition of metal onto a substrate or the like), the electrodes can be formed from plated wire (e.g., platinum on steel wire) or bulk metal (e.g., platinum wire). In certain embodiments, the electrode is formed from tantalum wire, e.g., coated with a conductive material.

In certain embodiments, the reference electrode, which can function as a reference electrode alone, or as a dual reference and counter electrode, is formed from silver, silver/silver chloride or the like. In certain embodiments, the reference electrode is juxtaposed and/or twisted with or around the working electrode. In certain embodiments, the reference electrode is helically wound around the working electrode. In certain embodiments, the assembly of wires can be coated or adhered together with an insulating material so as to provide an insulating attachment.

In certain embodiments, additional electrodes can be included in the sensor tail. For example, but not by way of limitation, a three-electrode system (a working electrode, a reference electrode and a counter electrode) and/or an additional working electrode (e.g., an electrode for detecting a second analyte). In certain embodiments where the sensor comprises two working electrodes, the two working electrodes can be juxtaposed around which the reference electrode is disposed upon (e.g., helically wound around the two or more working electrodes). In certain embodiments, the two or more working electrodes can extend parallel to each other. In certain embodiments, the reference electrode is coiled around the working electrode and extends towards the distal end (i.e., in vivo end) of the sensor tail. In certain embodiments, the reference electrode extends (e.g., helically) to the exposed region of the working electrode.

In certain embodiments, one or more working electrodes are helically wound around a reference electrode. In certain embodiments where two or more working electrodes are provided, the working electrodes can be formed in a double-, triple-, quad-, etc. helix configuration along the length of the sensor tail (for example, surrounding a reference electrode, insulated rod or other support structure). In certain embodiments, the electrodes, e.g., two or more working electrodes, are coaxially formed. For example, but not by way of limitation, the electrodes all share the same central axis.

In certain embodiments, the working electrode comprises a tube with a reference electrode disposed or coiled inside, including an insulator therebetween. Alternatively, the reference electrode comprises a tube with a working electrode disposed or coiled inside, including an insulator therebetween. In certain embodiments, a polymer (e.g., insulating) rod is provided, wherein the one or more electrodes (e.g., one or more electrode layers) are disposed upon (e.g., by electro-plating). In certain embodiments, a metallic (e.g., steel or tantalum) rod or wire is provided, coated with an insulating material (described herein), onto which the one or more working and reference electrodes are disposed upon. For example, but not by way of limitation, the present disclosure provides a sensor, e.g., a sensor tail, that comprises one or more tantalum wires, where a conductive material is disposed upon a portion of the one or more tantalum wires to function as a working electrode. In certain embodiments, the platinum-clad tantalum wire is covered with an insulating material, where the insulating material is partially covered with a silver/silver chloride composition to function as a reference and/or counter electrode.

In certain embodiments where an insulator is disposed upon the working electrode (e.g., upon the platinum surface of the electrode), a portion of the insulator can be stripped or otherwise removed to expose the electroactive surface of the working electrode. For example, but not by way of limitation, a portion of the insulator can be removed by hand, excimer lasing, chemical etching, laser ablation, grit-blasting or the like. Alternatively, a portion of the electrode can be masked prior to depositing the insulator to maintain an exposed electroactive surface area. In certain embodiments, the portion of the insulator that is stripped and/or removed can be from about 0.1 mm (about 0.004 inches) or less to about 2 mm (about 0.078 inches) or more in length, e.g., from about 0.5 mm (about 0.02 inches) to about 0.75 mm (0.03 inches) in length. In certain embodiments, the insulator is a non-conductive polymer. In certain embodiments, the insulator comprises parylene, fluorinated polymers, polyethylene terephthalate, polyvinylpyrrolidone, polyurethane, polyimide and other non-conducting polymers. In certain embodiments, glass or ceramic materials can also be used in the insulator layer. In certain embodiments, the insulator comprises parylene. In certain embodiments, the insulator comprises a polyurethane. In certain embodiments, the insulator comprises a polyurethane and polyvinylpyrrolidone.

Several parts of the sensor, including the active areas, are further described below.

2. Enzymes

An active area of a presently disclosed analyte sensor can be configured for detecting an analyte. Non-limiting examples of analytes that can be detected using the disclosed analyte sensors include asparagine and aspartate. In certain embodiments, an active area of a presently disclosed analyte sensor is configured to detect asparagine. In certain embodiments, an active area of a presently disclosed analyte sensor is configured to detect aspartate.

In certain embodiments, an active area of an analyte sensor of the present disclosure can be configured to detect two or more analytes. For example, but not by way of limitation, an active area can be configured to detect asparagine and aspartate. Alternatively, an active area can be configured to detect asparagine and/or aspartate and a second analyte. Non-limiting examples of second analytes include glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, aspartate, asparagine, total protein, uric acid, etc.

In certain embodiments, an analyte sensor of the present disclosure can include two or more active areas, where each active area is configured to detect a different analyte. In certain embodiments, the first active area can be configured to detect asparagine and the second active area can be configured to detect aspartate. In certain embodiments, the first active area can be configured to detect asparagine and/or aspartate and the second active area can be configured to detect a second analyte, e.g., glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, aspartate, asparagine, total protein and/or uric acid.

In certain embodiments, an analyte sensor of the present disclosure can include an asparagine-responsive active area or an aspartate-responsive active area. In certain embodiments, an asparagine-responsive active area can include one or more enzymes for detecting asparagine. In certain embodiments, an aspartate-responsive active area can include one or more enzymes for detecting aspartate.

Figure 22:
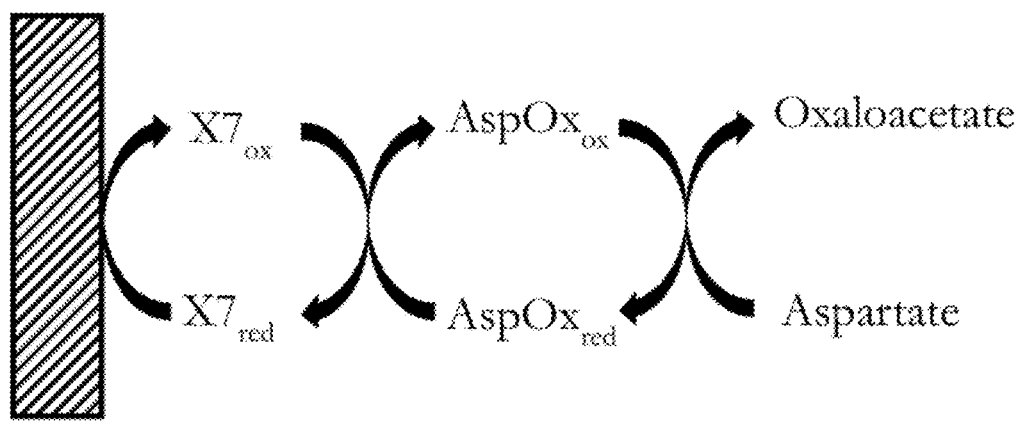
FIG. 22 shows a diagram of a particular enzyme system that can be used for detecting aspartate according to the present disclosure.

In certain embodiments, an analyte sensor of the present disclosure includes at least one active area configured to detect aspartate. A particular enzyme system that can be used for detecting aspartate is shown in FIG. 22. In the depicted enzymatic reaction, aspartate oxidase (depicted as AspOx in FIG. 22) can be used for detecting aspartate according to the disclosure herein. When an aspartate-responsive active area contains this enzyme system, aspartate oxidase can catalyze the oxidation of aspartate to oxaloacetate and the reduction of its coenzyme flavin adenine dinucleotide (FAD) to $FADH_2$. An electron transfer agent can then mediate the electron transfer from $FADH_2$ to the working electrode. The electrons transferred during this reaction provides the basis for aspartate detection at the working electrode. The electrochemical signal obtained at the working electrode can then be correlated to the amount of aspartate that was initially present in the sample.

Figure 23:
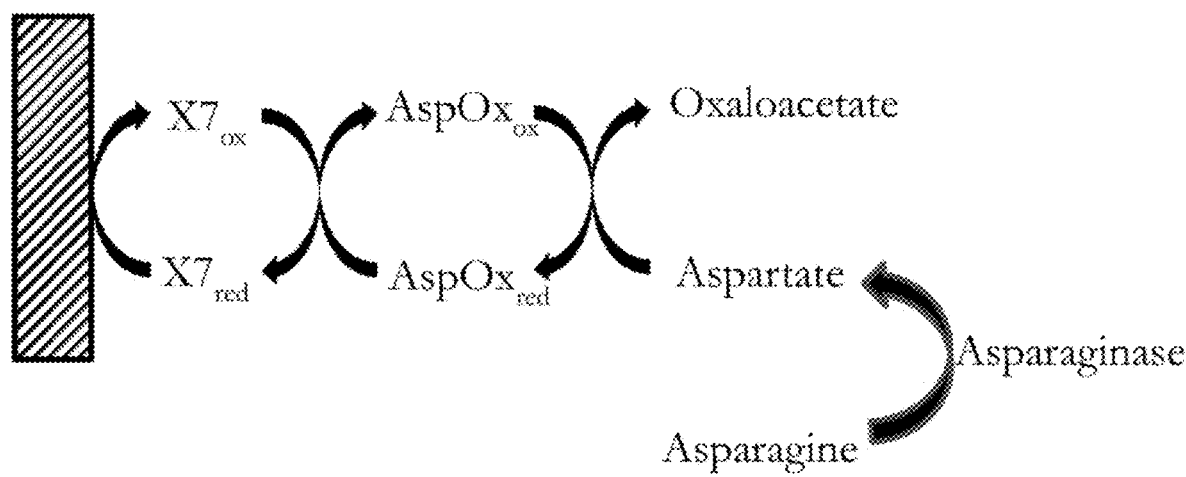
FIG. 23 shows a diagram of a particular enzyme system that can be used for detecting asparagine according to the present disclosure.

In certain embodiments, an analyte sensor of the present disclosure includes at least one active area configured to detect asparagine. A particular enzyme system that can be used for detecting asparagine is shown in FIG. 23. As shown in FIG. 23, the enzymatic system for detecting aspartate as depicted in FIG. 22 can be modified to detect asparagine by the addition of an asparaginase. In certain embodiments, the enzyme system can include an aspartate oxidase and an asparaginase. As shown in FIG. 23, the asparaginase catalyzes the hydrolysis of asparagine to produce aspartate. The produced aspartate can then, in turn, be oxidized by aspartate oxidase, as depicted in FIGS. 22 and 23 and described above. For example, but not way of limitation, aspartate oxidase catalyzes the oxidation of aspartate to oxaloacetate and the reduction of its coenzyme FAD to $FADH_2$, and then the electron transfer agent mediates the electron transfer from $FADH_2$ to the working electrode. The electrochemical signal obtained at the working electrode can then be correlated to the amount of asparagine that was initially present in the sample.

Any suitable aspartate oxidase can be used in an analyte sensor of the present disclosure. Particular examples of aspartate oxidases suitable for use in the analyte sensors disclosed herein include, but are not limited to, potassium-dependent and potassium-independent aspartate oxidases. In certain embodiments, the aspartate oxidase used in the enzyme system is potassium-dependent. In certain other embodiments, the aspartate oxidase used in the enzyme system is potassium-independent. Non-limiting examples of an aspartate oxidase include L-aspartate oxidases from *Sulfolobus tokodaii, Escherichia coli, Arabidopis thaliana* or *Thermococcus litoralis*. For example, but not by way of limitation, L-aspartate oxidases for use in the aspartate and asparagine sensors of the present disclosure are disclosed in Nasu et al, J. of Biological Chemistry 257(2):626-32 (1982); Bifulco et al., Appl. Microbiol. Biotechnol. 97(16):7285-95 (2013); Washio et al., Extremophiles 22(1):59-71 (2018); and Hao et al., Plant Science 271:133-142 (2018), the contents of which are incorporated herein by reference in their entireties.

Any suitable asparaginase can be used in an analyte sensor of the present disclosure. Particular examples of asparaginases suitable for use in the analyte sensors disclosed herein include, but are not limited to, potassium-dependent and potassium-independent asparaginases. In certain embodiments, the asparaginase used in the enzyme system is potassium-dependent. In certain other embodiments, the asparaginase used in the enzyme system is potassium-independent. Non-limiting examples of potassium-independent and -dependent asparaginases are disclosed in Ajewole et al., FEBS Journal 285(8):1528-1539 (2018) and Bejger et al., Acta Crystallogr. D. Biol. Crystallogr. 70(Pt 7):1854-72 (2014), the contents of which are incorporated herein by reference in their entireties. In certain embodiments, an asparaginase for use in the present disclosure is the potassium-dependent (PvAspG1) and/or potassium-independent (PvAspG-T2) asparaginases from *Phaseolus vulgaris*.

In certain embodiments, the present disclosure provides an analyte sensor for detecting aspartate. In certain embodiments, the analyte sensor for detecting aspartate can include a sensor tail comprising at least one working electrode and at least one aspartate-responsive active area disposed upon a surface of the working electrode, where the aspartate-responsive active area includes an aspartate oxidase. In certain embodiments, the aspartate oxidase is potassium-independent.

The present disclosure further provides an analyte sensor for detecting asparagine. In certain embodiments, an analyte sensor for detecting asparagine can include a sensor tail comprising at least one working electrode and at least one asparagine-responsive active area disposed upon a surface of the working electrode, where the asparagine-responsive active area includes an enzyme system comprising an oxidase and a hydrolase. In certain embodiments, the oxidase is an aspartate oxidase. In certain embodiments, the hydrolase is an asparaginase. In certain embodiments, the asparagine-responsive active area includes a first enzymatic layer that includes the oxidase, e.g., an aspartate oxidase, and a second layer disposed upon the first enzymatic layer that includes a hydrolase, e.g., an asparaginase. Alternatively or additionally, the oxidase, e.g., an aspartate oxidase, and the hydrolase, e.g., an asparaginase, are retained within the same enzymatic layer. In certain embodiments, both the aspartate oxidase and asparaginase present in the asparagine-responsive active area are potassium-independent.

In certain embodiments, an asparagine-responsive active area of the present disclosure can include a ratio of aspartate oxidase to asparaginase from about 100:1 to about 1:100, e.g., from about 95:1 to about 1:95, from about 90:1 to about 1:90, from about 85:1 to about 1:85, from about 80:1 to about 1:80, from about 75:1 to about 1:75, from about 60:1 to about 1:60, from about 55:1 to about 1:55, from about 50:1 to about 1:50, from about 45:1 to about 1:45, from about 40:1 to about 1:40, from about 35:1 to about 1:35, from about 30:1 to about 1:30, from about 25:1 to about 1:25, from about 20:1 to about 1:20, from about 15:1 to about 1:15, from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3 or from about 2:1 to about 1:2. In certain embodiments, the asparagine-responsive active area can include a ratio of aspartate oxidase to asparaginase from about 5:1 to about 1:5. In certain embodiments, the asparagine-responsive active area can include a ratio of aspartate oxidase to asparaginase from about 2:1 to about 1:2. In certain embodiments, the asparagine-responsive active area can include a ratio of aspartate oxidase to asparaginase of about 1:1.

In certain embodiments, the analyte-responsive active area, e.g., an aspartate-responsive active area or an asparagine-responsive active area, can include from about 10% to about 80% by weight, e.g., from about 10% to about 75%, from about 10% to about 70%, from about 10% to about 65%, from about 10% to about 60%, from about 10% to about 55%, from about 10% to about 50%, from about 10% to about 45%, from about 15% to about 50%, from about 15% to about 45%, from about 20% to about 40%, from about 20% to about 35%, from about 20% to about 30% by weight of an aspartate oxidase. In certain embodiments, the analyte-responsive active area, e.g., an aspartate-responsive active area or an asparagine-responsive active area, can include from about 10% to about 50% by weight of aspartate oxidase. In certain embodiments, the analyte-responsive active area, e.g., an aspartate-responsive active area or an asparagine-responsive active area, can include from about 15% to about 45% by weight of aspartate oxidase. In certain embodiments, the analyte-responsive active area, e.g., an aspartate-responsive active area or an asparagine-responsive active area, can include from about 15% to about 35% by weight of aspartate oxidase. In certain embodiments, the analyte-responsive active area, e.g., an aspartate-responsive active area or an asparagine-responsive active area, can include from about 10% to about 35% by weight of aspartate oxidase.

In certain embodiments, the analyte-responsive active area, e.g., an asparagine-responsive active area, can include from about 0.1% to about 50% by weight, e.g., from about 0.1% to about 45%, from about 0.1% to about 40%, from about 0.1% to about 35%, from about 0.1% to about 30%, from about 0.1% to about 25%, from about 0.1% to about 20%, from about 0.1% to about 15%, from about 0.1% to about 10%, from about 0.5% to about 45%, from about 0.5% to about 40%, from about 0.5% to about 30%, from about 0.5% to about 25%, from about 0.5% to about 20%, from about 0.5% to about 15%, from about 0.5% to about 10%, from about 0.5% to about 5%, from about 20% a to about 40%, from about 20% to about 35%, from about 20% to about 30% by weight of an asparaginase. In certain embodiments, the analyte-responsive active area, e.g., an asparagine-responsive active area, can include from about 0.1% to about 20% by weight of asparaginase. In certain embodiments, the analyte-responsive active area, e.g., an asparagine-responsive active area, can include from about 5% to about 20% by weight of asparaginase. In certain embodiments, the analyte-responsive active area, e.g., an asparagine-responsive active area, can include from about 0.1% to about 5% by weight of asparaginase. In certain embodiments, the analyte-responsive active area, e.g., an asparagine-responsive active area, can include from about 0.1% to about 2% by weight of asparaginase.

In certain embodiments, an aspartate-responsive active area or an asparagine-responsive active area can further include a stabilizing agent, e.g., for stabilizing the one or more enzymes. For example, but not by way of limitation, the stabilizing agent can be an albumin, e.g., a serum albumin. Non-limiting examples of serum albumins include bovine serum albumin and human serum albumin. In certain embodiments, the stabilizing agent is a human serum albumin. In certain embodiments, the stabilizing agent is a bovine serum albumin. In certain embodiments, an aspartate-responsive active area or an asparagine-responsive active area of the present disclosure can include a ratio of stabilizing agent, e.g., a serum albumin, to asparaginase and/or aspartate oxidase from about 100:1 to about 1:100, e.g., from about 95:1 to about 1:95, from about 90:1 to about 1:90, from about 85:1 to about 1:85, from about 80:1 to about 1:80, from about 75:1 to about 1:75, from about 60:1 to about 1:60, from about 55:1 to about 1:55, from about 50:1 to about 1:50, from about 45:1 to about 1:45, from about 40:1 to about 1:40, from about 35:1 to about 1:35, from about 30:1 to about 1:30, from about 25:1 to about 1:25, from about 20:1 to about 1:20, from about 15:1 to about 1:15, from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3 or from about 2:1 to about 1:2. In certain embodiments, an aspartate-responsive active area or an asparagine-responsive active area can include a ratio of stabilizing agent to asparaginase and/or aspartate oxidase from about 80:1 to about 1:80. In certain embodiments, an aspartate-responsive active area or an asparagine-responsive active area can include a ratio of stabilizing agent to asparaginase and/or aspartate oxidase from about 50:1 to about 1:50. In certain embodiments, an aspartate-responsive active area or an asparagine-responsive active area can include a ratio of stabilizing agent to asparaginase and/or aspartate oxidase from about 10:1 to about 1:10. In certain embodiments, an aspartate-responsive active area or an asparagine-responsive active area can include a ratio of stabilizing agent to asparaginase and/or aspartate oxidase from about 7:1 to about 1:7. In certain embodiments, an aspartate-responsive active area or an asparagine-responsive active area can include a ratio of stabilizing agent to asparaginase and/or aspartate oxidase from about 6:1 to about 1:6. In certain embodiments, an aspartate-responsive active area or an asparagine-responsive active area can include a ratio of stabilizing agent to asparaginase and/or aspartate oxidase from about 5:1 to about 1:5. In certain embodiments, an aspartate-responsive active area or an asparagine-responsive active area can include a ratio of stabilizing agent to asparaginase and/or aspartate oxidase from about 4:1 to about 1:4. In certain embodiments, an aspartate-responsive active area or an asparagine-responsive active area can include a ratio of stabilizing agent to asparaginase and/or aspartate oxidase from about 2:1 to about 1:2. In certain embodiments, an aspartate-responsive active area or an asparagine-responsive active area can include a ratio of stabilizing agent to asparaginase and/or aspartate oxidase of about 1:1. In certain embodiments, the an aspartate-responsive active area or an asparagine-responsive active area can include by weight from about 5% to about 50%, e.g., from about 10% to about 50%, from about 15% to about 45%, from about 20% to about 40%, from about 20% to about 35%, from about 20% to about 30%, of the stabilizer. In certain embodiments, the aspartate-responsive active area or an asparagine-responsive active area can include from about 5% to about 40% of the stabilizing agent by weight. In certain embodiments, the aspartate-responsive active area or an asparagine-responsive active area can include from about 5% to about 35% of the stabilizing agent by weight. In certain embodiments, the aspartate-responsive active area or an asparagine-responsive active area can include from about 5% to about 30% of the stabilizing agent by weight. In certain embodiments, the aspartate-responsive active area or an asparagine-responsive active area can include from about 10% to about 30% of the stabilizing agent by weight. In certain embodiments, the aspartate-responsive active area or an asparagine-responsive active area can include from about 15% to about 35% of the stabilizing agent by weight.

In certain embodiments, an analyte-responsive active area, e.g., an aspartate-responsive active area or an asparagine-responsive active area, can further include a cofactor for one or more enzymes present in the analyte-responsive active area. In certain embodiments, the cofactor is NAD(P) or FAD. In certain embodiments, the cofactor can be physically retained within the analyte-responsive active area. For example, but not by way of limitation, a membrane overcoating the analyte-responsive active area can aid in retaining the cofactor within the analyte-responsive active area while still permitting sufficient inward diffusion of the analyte to permit detection thereof.

In certain embodiments, an analyte sensor can include two working electrodes, e.g., a first active area disposed on a first working electrode and a second active area disposed on a second working electrode. In certain embodiments, an analyte sensor disclosed herein can feature an aspartate-responsive active area and a second active area for detecting an analyte different from aspartate. In certain embodiments, an analyte sensor disclosed herein can feature an asparagine-responsive active area and a second active area for detecting an analyte different from aspartate. For example, but not by way of limitation, such analyte sensors can include a sensor tail with at least a first working electrode and a second working electrode, an aspartate-responsive active area or an asparagine-responsive active area disposed upon a surface of the first working electrode and a second active area, e.g., a second enzyme-responsive active area, configured to detect a different analyte disposed upon a surface of the second working electrode. Alternatively, in certain embodiments, an analyte sensor of the present disclosure can include a sensor tail with at least a first working electrode and a second working electrode, an aspartate-responsive active area disposed upon a surface of the first working electrode and an asparagine-responsive active area disposed upon a surface of the second working electrode. In certain embodiments, when the sensor is configured to detect two or more analytes, detection of each analyte can include applying a potential to each working electrode separately, such that separate signals are obtained from each analyte. The signal obtained from each analyte can then be correlated to an analyte concentration through use of a calibration curve or function, or by employing a lookup table. In certain particular embodiments, correlation of the analyte signal to an analyte concentration can be conducted through use of a processor.

In certain other analyte sensor configurations, the first active area and the second active area can be disposed upon a single working electrode. A first signal can be obtained from the first active area, e.g., at a low potential, and a second signal containing a signal contribution from both active areas can be obtained at a higher potential. Subtraction of the first signal from the second signal can then allow the signal contribution arising from the second analyte to be determined. The signal contribution from each analyte can then be correlated to an analyte concentration in a similar manner to that described for sensor configurations having multiple working electrodes. In certain embodiments, when the aspartate-responsive active area or asparagine-responsive active area and the second active area, e.g., a second enzyme-responsive active area, configured to detect a different analyte are arranged upon a single working electrode in this manner, one of the active areas can be configured such that it can be interrogated separately to facilitate detection of each analyte. For example, either the aspartate/asparagine-responsive active area or the second active area responsive to the second analyte can produce a signal independently of the other active area.

It is also to be appreciated that the sensitivity (output current) of the analyte sensors toward each analyte can be varied by changing the coverage (area or size) of the active areas, the area ratio of the active areas with respect to one another, the identity, thickness and/or composition of a mass transport limiting membrane overcoating the active areas. Variation of these parameters can be conducted readily by one having ordinary skill in the art once granted the benefit of the disclosure herein.

3. Redox Mediators

In certain embodiments, an analyte sensor disclosed herein can include an electron transfer agent. For example, but not way of limitation, at least one active area of a presently disclosed analyte sensor can include an electron transfer agent. In certain embodiments, an analyte sensor of the present disclosure can include at least one aspartate-responsive active area that includes an electron transfer agent. In certain embodiments, an analyte sensor of the present disclosure can include at least one asparagine-responsive active area that includes an electron transfer agent.

In certain embodiments, an analyte sensor of the present disclosure can include two or more active areas, where only one active area includes an electron transfer agent, e.g., the aspartate-responsive active area or the asparagine-responsive active area. In certain embodiments, an analyte sensor of the present disclosure can include two or more active areas, where each active area includes an electron transfer agent. For example, but not way of limitation, an analyte sensor of the present disclosure can include a sensor tail with at least a first working electrode and a second working electrode, an aspartate-responsive active area or an asparagine-responsive active area comprising a first electron transfer agent disposed upon a surface of the first working electrode and a second analyte-responsive active area comprising at least one enzyme responsive to the second analyte and a second electron transfer agent disposed upon a surface of the second working electrode. In certain embodiments, the first electron agent and the second electron transfer agent are the same. Alternatively, the first electron agent and the second electron transfer agent are different.

Suitable electron transfer agents can facilitate conveyance of electrons to the adjacent working electrode after an analyte undergoes an enzymatic oxidation-reduction reaction within the corresponding active area, thereby generating a current that is indicative of the presence of that particular analyte. The amount of current generated is proportional to the quantity of analyte that is present.

In certain embodiments, suitable electron transfer agents can include electroreducible and electrooxidizable ions, complexes or molecules (e.g., quinones) having oxidation-reduction potentials that are a few hundred millivolts above or below the oxidation-reduction potential of the standard calomel electrode (SCE). In certain embodiments, the redox mediators can include osmium complexes and other transition metal complexes, such as those described in U.S. Pat. Nos. 6,134,461 and 6,605,200, which are incorporated herein by reference in their entirety. Additional examples of suitable redox mediators include those described in U.S. Pat. Nos. 6,736,957, 7,501,053 and 7,754,093, the disclosures of each of which are also incorporated herein by reference in their entirety. Other examples of suitable redox mediators include metal compounds or complexes of ruthenium, osmium, iron (e.g., polyvinylferrocene or hexacyanoferrate), or cobalt, including metallocene compounds thereof, for example. Suitable ligands for the metal complexes can also include, for example, bidentate or higher denticity ligands such as, for example, bipyridine, biimidazole, phenanthroline or pyridyl(imidazole). Other suitable bidentate ligands can include, for example, amino acids, oxalic acid, acetylacetone, diaminoalkanes, or o-diaminoarenes. Any combination of monodentate, bidentate, tridentate, tetradentate or higher denticity ligands can be present in a metal complex, e.g., osmium complex, to achieve a full coordination sphere. In certain embodiments, the electron transfer agent is an osmium complex. In certain embodiments, the electron transfer agent is osmium complexed with bidentate ligands.

In certain embodiments, electron transfer agents disclosed herein can comprise suitable functionality to promote covalent bonding to a polymer (also referred to herein as a polymeric backbone) within the active areas as discussed further below. For example, but not by way of limitation, an electron transfer agent for use in the present disclosure can include a polymer-bound electron transfer agent. Suitable non-limiting examples of polymer-bound electron transfer agents include those described in U.S. Pat. Nos. 8,444,834, 8,268,143 and 6,605,201, the disclosures of which are incorporated herein by reference in their entirety. In certain embodiments, the electron transfer agent is a bidentate osmium complex bound to a polymer described herein. In certain embodiments, the electron transfer agent is a bidentate osmium complex bound to a polymer described herein, e.g., a polymeric backbone described in Section 4 below. In certain embodiments, the polymer-bound electron transfer agent shown in FIG. 3 of U.S. Pat. No. 8,444,834 can be used in a sensor of the present disclosure.

In certain embodiments, an analyte sensor of the present disclosure can include a sensor tail comprising a working electrode, an aspartate-responsive active area comprising an aspartate oxidase and an electron transfer agent disposed upon a surface of the working electrode.

In certain embodiments, an analyte sensor of the present disclosure can include a sensor tail comprising a working electrode, an asparagine-responsive active area comprising an asparaginase, an aspartate oxidase and an electron transfer agent disposed upon a surface of the working electrode. In certain embodiments, the asparagine-responsive active area includes a first enzymatic layer that includes an aspartate oxidase and an electron transfer agent, and a second layer disposed upon the first enzymatic layer that includes an asparaginase. Alternatively or additionally, the aspartate oxidase, the asparaginase and the electron transfer agent are retained within the same enzymatic layer.

In certain embodiments, an aspartate-responsive active area or an asparagine-responsive active area of the present disclosure can include a ratio of aspartate oxidase and/or asparaginase to redox mediator from about 100:1 to about 1:100, e.g., from about 95:1 to about 1:95, from about 90:1 to about 1:90, from about 85:1 to about 1:85, from about 80:1 to about 1:80, from about 75:1 to about 1:75, from about 60:1 to about 1:60, from about 55:1 to about 1:55, from about 50:1 to about 1:50, from about 45:1 to about 1:45, from about 40:1 to about 1:40, from about 35:1 to about 1:35, from about 30:1 to about 1:30, from about 25:1 to about 1:25, from about 20:1 to about 1:20, from about 15:1 to about 1:15, from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3 or from about 2:1 to about 1:2. In certain embodiments, an aspartate-responsive active area or an asparagine-responsive active area can include a ratio of aspartate oxidase and/or asparaginase to redox mediator from about 7:1 to about 1:7. In certain embodiments, an aspartate-responsive active area or an asparagine-responsive active area can include a ratio of aspartate oxidase and/or asparaginase to redox mediator from about 6:1 to about 1:6. In certain embodiments, an aspartate-responsive active area or an asparagine-responsive active area can include a ratio of aspartate oxidase and/or asparaginase to redox mediator from about 5:1 to about 1:5. In certain embodiments, an aspartate-responsive active area or an asparagine-responsive active area can include a ratio of aspartate oxidase and/or asparaginase to redox mediator from about 4:1 to about 1:4. In certain embodiments, an aspartate-responsive active area or an asparagine-responsive active area can include a ratio of aspartate oxidase and/or asparaginase to redox mediator from about 3:1 to about 1:3. In certain embodiments, an aspartate-responsive active area or an asparagine-responsive active area can include a ratio of aspartate oxidase and/or asparaginase to redox mediator from about 2:1 to about 1:2. In certain embodiments, an aspartate-responsive active area or an asparagine-responsive active area can include a ratio of aspartate oxidase and/or asparaginase to redox mediator of about 1:1. In certain embodiments, the analyte-responsive active area, e.g., an aspartate-responsive active area or an asparagine-responsive active area, can include by weight from about 10% to about 50% of the redox mediator, e.g., from about 15% to about 45%, from about 20% to about 40%, from about 20% to about 35% or from about 20% to about 30% of the redox mediator. In certain embodiments, the analyte-responsive active area, e.g., an aspartate-responsive active area or an asparagine-responsive active area, can include from about 5% to about 35% by weight of the redox mediator. In certain embodiments, the analyte-responsive active area, e.g., an aspartate-responsive active area or an asparagine-responsive active area, can include from about 10% to about 35% by weight of the redox mediator. In certain embodiments, the analyte-responsive active area, e.g., an aspartate-responsive active area or an asparagine-responsive active area, can include from about 10% to about 30% by weight of the redox mediator. In certain embodiments, the analyte-responsive active area, e.g., an aspartate-responsive active area or an asparagine-responsive active area, can include from about 15% to about 35% by weight of the redox mediator.

4. Polymeric Backbone

In certain embodiments, one or more active sites for promoting analyte detection can include a polymer to which an enzyme and/or redox mediator is covalently bound. Any suitable polymeric backbone can be present in the active area for facilitating detection of an analyte through covalent bonding of the enzyme and/or redox mediator thereto. Non-limiting examples of suitable polymers within the active area include polyvinylpyridines, e.g., poly(4-vinylpyridine) and/or poly(2-vinylpyridine), and polyvinylimidazoles, e.g., poly(N-vinylimidazole) and poly(1-vinylimidazole), or a copolymer thereof, for example, in which quaternized pyridine groups serve as a point of attachment for the redox mediator or enzyme thereto. Illustrative copolymers that can be suitable for inclusion in the active areas include those containing monomer units such as styrene, acrylamide, methacrylamide, or acrylonitrile, for example. In certain embodiments, the polymer is a co-polymer of vinylpyridine and styrene. In certain embodiments, polymers that can be present in an active area include a polyurethane or a copolymer thereof, and/or polyvinylpyrrolidone. Additional non-limiting examples of polymers that can be present in the active area include those described in U.S. Pat. No. 6,605,200, incorporated herein by reference in its entirety, such as poly(acrylic acid), styrene/maleic anhydride copolymer, methylvinylether/maleic anhydride copolymer (GANTREZ polymer), poly(vinylbenzylchloride), poly(allylamine), polylysine, poly(4-vinylpyridine) quaternized with carboxypentyl groups, and poly(sodium 4-styrene sulfonate). In certain embodiments where the analyte sensor includes two active sites, the polymer within each active area can be the same or different.

In certain embodiments, the polymer is a polyvinylpyridine-based polymer. In certain embodiments, the polymer is a polyvinylpyridine or a copolymer thereof. In certain embodiments, the polymer is a co-polymer of vinylpyridine and styrene.

In certain embodiments, one or more enzymes of an analyte-responsive active area can be covalently bonded to the polymer. In certain embodiments, one or more enzymes of an aspartate-responsive active area can be covalently bonded to the polymer. For example, but not by way of limitation, an aspartate oxidase can be covalently bonded to a polymer within an aspartate-responsive active area.

In certain embodiments, when an enzyme system with multiple enzymes is present in a given active area, all of the multiple enzymes can be covalently bonded to the polymer. In certain other embodiments, only a subset of the multiple enzymes is covalently bonded to the polymer. For example, and not by the way of limitation, one or more enzymes within an enzyme system can be covalently bonded to the polymer and at least one enzyme can be non-covalently associated with the polymer, such that the non-covalently bonded enzyme is physically retained within the polymer. For example, but not by way of limitation, aspartate oxidase can be covalently bonded to a polymer within an asparagine-responsive active area of the disclosed analyte sensors. In certain embodiments, aspartate oxidase can be covalently bonded to a polymer within an aspartate-responsive active area of the disclosed analyte sensors. In certain embodiments, asparaginase can be covalently bonded to a polymer within an asparagine-responsive active area. In certain embodiments, aspartate oxidase can be covalently bonded to the polymer and asparaginase can be non-covalently associated with the polymer. Alternatively, asparaginase can be covalently bonded to the polymer and aspartate oxidase can be non-covalently associated with the polymer. In certain embodiments where one or more enzymes is not covalently bonded, it can be physically retained within the aspartate or asparagine-responsive active area.

In certain embodiments, a membrane overcoating the aspartate or asparagine-responsive active area can aid in retaining the one or more enzymes within the aspartate or asparagine-responsive active area while still permitting sufficient inward diffusion of aspartate or asparagine to permit detection thereof. Suitable membrane polymers for overcoating the analyte-responsive active area are discussed further herein.

In certain embodiments, when a stabilizer is present in an active area, one or more enzymes within the area can be covalently bonded to the stabilizer. For example, and not by the way of limitation, one or more enzymes can be covalently bonded to the stabilizer, e.g., albumin, present in the active area. In certain embodiments, aspartate oxidase present in an active area of the present disclosure can be covalently bonded to the stabilizer. In certain embodiments, asparaginase present in an active area of the present disclosure can be covalently bonded to the stabilizer.

In certain particular embodiments, covalent bonding of the one or more enzymes and/or redox mediators to the polymer and/or stabilizer in a given active area can take place via crosslinking introduced by a suitable crosslinking agent. In certain embodiments, crosslinking of the polymer and/or stabilizer to the one or more enzymes and/or redox mediators can reduce the occurrence of delamination of the enzyme compositions from an electrode. Suitable crosslinking agents can include one or more crosslinkable functionalities such as, but not limited to, vinyl, alkoxy, acetoxy, enoxy, oxime, amino, hydroxyl, cyano, halo, acrylate, epoxide and isocyanato groups. In certain embodiments, the crosslinking agent comprises one or more, two or more, three or more or four or more epoxide groups. For example, but not by way of limitation, a crosslinker for use in the present disclosure can include mono-, di-, tri- and tetra-ethylene oxides. In certain embodiments, crosslinking agents for reaction with free amino groups in the enzyme (e.g., with the free side chain amine in lysine) can include crosslinking agents such as, for example, polyethylene glycol dibutyl ethers, polypropylene glycol dimethyl ethers, polyalkylene glycol allyl methyl ethers, polyethylene glycol diglycidyl ether (PEGDGE) or other polyepoxides, cyanuric chloride, N-hydroxysuccinimide, imidoesters, epichlorohydrin, or derivatized variants thereof. In certain embodiments, the crosslinking agent is PEGDGE, e.g., having an average molecular weight ($M_n$) from about 200 to 1,000, e.g., about 400. In certain embodiments, the crosslinking agent is PEGDGE 400. In certain embodiments, the crosslinking agent can be glutaraldehyde. In certain embodiments, the crosslinking of the enzyme to the polymer is generally intermolecular. In certain embodiments, the crosslinking of the enzyme to the polymer is generally intramolecular.

In certain embodiments, the aspartate and/or asparagine-responsive active area can include a ratio of crosslinking agent to one or more enzymes of the active area, e.g., asparagine and/or aspartate oxidase, from about 100:1 to about 1:100. In certain embodiments, the aspartate and/or asparagine-responsive active area can include a ratio of crosslinking agent to one or more enzymes of the active area, e.g., asparagine and/or aspartate oxidase, from about 40:1 to about 1:40, e.g., from about 35:1 to about 1:35, from about 30:1 to about 1:30, from about 25:1 to about 1:25, from about 20:1 to about 1:20, from about 15:1 to about 1:15, from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3, from about 2:1 to about 1:2 or about 1:1. In certain embodiments, the aspartate and/or asparagine-responsive active area can include by weight from about 5% to about 50%, e.g., from about 5% to about 45%, from about 5% to about 40%, from about 5% to about 35%, from about 10% to about 30% or from about 10% to about 25%, of the crosslinking agent.

5. Mass Transport Limiting Membranes

In certain embodiments, the analyte sensors disclosed herein further include a membrane that overcoats at least one active area, e.g., a first active area and/or a second active area, and is permeable to one or more analytes. For example, but not by way of limitation, the membrane is permeable to aspartate and/or asparagine. In certain embodiments, the membrane overcoats each of the active areas of an analyte sensor. Alternatively, a first membrane overcoats one of the active areas and a second membrane overcoats the second active area. Alternatively, a first membrane overcoats one of the active areas and a second membrane overcoats both the first and second active areas.

In certain embodiments, a membrane overcoating an analyte-responsive active area can function as a mass transport limiting membrane and/or to improve biocompatibility. A mass transport limiting membrane can act as a diffusion-limiting barrier to reduce the rate of mass transport of the analyte. For example, but not by way of limitation, limiting access of an analyte, e.g., aspartate or asparagine, to the analyte-responsive active area with a mass transport limiting membrane can aid in avoiding sensor overload (saturation), thereby improving detection performance and accuracy.

In certain embodiments, the mass transport limiting membrane can be homogeneous and can be single-component (contain a single membrane polymer). Alternatively, the mass transport limiting membrane can be multi-component (contain two or more different membrane polymers). In certain embodiments, the multi-component membrane can be present as a bilayer membrane or as a homogeneous admixture of two or more membrane polymers. A homogeneous admixture can be deposited by combining the two or more membrane polymers in a solution and then depositing the solution upon a working electrode, e.g., dip coating.

In certain embodiments, the mass transport limiting membrane can include two or more layers, e.g., a bilayer or trilayer membrane. In certain embodiments, each layer can comprise a different polymer or the same polymer at different concentrations or thicknesses. In certain embodiments, the first analyte-responsive active area can be covered by a multi-layered membrane, e.g., a bilayer membrane, and the second analyte-responsive active area can be covered by a single membrane. In certain embodiments, the first analyte-responsive active area can be covered by a multi-layered membrane, e.g., a bilayer membrane, and the second analyte-responsive active area can be covered by a multi-layered membrane, e.g., a bilayer membrane. In certain embodiments, the first analyte-responsive active area can be covered by a single membrane and the second analyte-responsive active area can be covered by a multi-layered membrane, e.g., a bilayer membrane be covered by a single membrane. In certain embodiments, the first analyte-responsive active area can be covered by a single membrane and the second analyte-responsive active area can be covered by a single membrane.

In certain embodiments, a mass transport limiting membrane can include polymers containing heterocyclic nitrogen groups. In certain embodiments, a mass transport limiting membrane can include a polyvinylpyridine, a polyvinylimidazole, a copolymer of vinylpyridine and styrene, a polyurethane or a polyether urethane, or a chemically related material, or membranes that are made of silicone, and the like. In certain embodiments, a mass transport limiting membrane can include a polyvinylpyridine-based polymer. Non-limiting examples of polyvinylpyridine-based polymers are disclosed in U.S. Patent Publication No. 2003/0042137 (e.g., Formula 2b), the contents of which are incorporated by reference herein in its entirety.

In certain embodiments, a mass transport limiting membrane can include a polyvinylpyridine (e.g., poly(4-vinylpyridine) or poly(4-vinylpyridine)), a polyvinylimidazole, a polyvinylpyridine copolymer (e.g., a copolymer of vinylpyridine and styrene), a polyacrylate, a polyurethane, a polyether urethane, a silicone, a polytetrafluoroethylene, a polyethylene-co-tetrafluoroethylene, a polyolefin, a polyester, a polycarbonate, a biostable polytetrafluoroethylene, homopolymers, copolymers or terpolymers of polyurethanes, a polypropylene, a polyvinylchloride, a polyvinylidene difluoride, a polybutylene terephthalate, a polymethylmethacrylate, a polyether ether ketone, cellulosic polymers, polysulfones and block copolymers thereof including, for example, di-block, tri-block, alternating, random and graft copolymers or a chemically related material and the like.

In certain embodiments, a membrane for use in the present disclosure, e.g., a single-component membrane, can include a polyvinylpyridine (e.g., poly(4-vinylpyridine) and/or poly(2-vinylpyridine)). In certain embodiments, a membrane for use in the present disclosure, e.g., a single-component membrane, can include poly(4-vinylpyridine). In certain embodiments, a membrane for use in the present disclosure, e.g., a single-component membrane, can include a copolymer of vinylpyridine and styrene. In certain embodiments, the membrane can comprise a polyvinylpyridine-co-styrene copolymer. For example, but not by way of limitation, a polyvinylpyridine-co-styrene copolymer for use in the present disclosure can include a polyvinylpyridine-co-styrene copolymer in which a portion of the pyridine nitrogen atoms were functionalized with a non-crosslinked polyethylene glycol tail and a portion of the pyridine nitrogen atoms were functionalized with an alkylsulfonic acid, e.g., a propylsulfonic acid, group. In certain embodiments, a derivatized polyvinylpyridine-co-styrene copolymer for use as a membrane polymer can be the 10Q5 polymer as described in U.S. Pat. No. 8,761,857, the contents of which are incorporated by reference herein in its entirety. In certain embodiments, the polyvinylpyridine-based polymer has a molecular weight from about 50 Da to about 500 kDa.

A suitable copolymer of vinylpyridine and styrene can have a styrene content ranging from about 0.01% to about 50% mole percent, or from about 0.05% to about 45% mole percent, or from about 0.1% to about 40% mole percent, or from about 0.5% to about 35% mole percent, or from about 1% to about 30% mole percent, or from about 2% to about 25% mole percent, or from about 5% to about 20% mole percent. Substituted styrenes can be used similarly and in similar amounts. A suitable copolymer of vinylpyridine and styrene can have a molecular weight of 5 kDa or more, or about 10 kDa or more, or about 15 kDa or more, or about 20 kDa or more, or about 25 kDa or more, or about 30 kDa or more, or about 40 kDa or more, or about 50 kDa or more, or about 75 kDa or more, or about 90 kDa or more, or about 100 kDa or more. In non-limiting examples, a suitable copolymer of vinylpyridine and styrene can have a molecular weight ranging from about 5 kDa to about 150 kDa, or from about 10 kDa to about 125 kDa, or from about 15 kDa to about 100 kDa, or from about 20 kDa to about 80 kDa, or from about 25 kDa to about 75 kDa, or from about 30 kDa to about 60 kDa.

In certain embodiments, the membrane can comprise polymers such as, but not limited to, poly(styrene co-maleic anhydride), dodecylamine and poly(propylene glycol)-block-polyethylene glycol)-block-poly(propylene glycol) (2-aminopropyl ether) crosslinked with poly(propylene glycol)-block-poly(ethylene glycol)-block-poly(propylene glycol) bis(2-aminopropyl ether); poly(N-isopropyl acrylamide); a copolymer of poly(ethylene oxide) and poly (propylene oxide); or a combination thereof.

In certain embodiments, the membrane includes a polyurethane membrane that includes both hydrophilic and hydrophobic regions. In certain embodiments, a hydrophobic polymer component is a polyurethane, a polyurethane urea or poly(ether-urethane-urea). In certain embodiments, a polyurethane is a polymer produced by the condensation reaction of a diisocyanate and a difunctional hydroxyl-containing material. In certain embodiments, a polyurethane urea is a polymer produced by the condensation reaction of a diisocyanate and a difunctional amine-containing material. In certain embodiments, diisocyanates for use herein include aliphatic diisocyanates, e.g., containing from about 4 to about 8 methylene units, or diisocyanates containing cycloaliphatic moieties. Additional non-limiting examples of polymers that can be used for the generation of a membrane of a presently disclosed sensor include vinyl polymers, polyethers, polyesters, polyamides, inorganic polymers (e.g., polysiloxanes and polycarbosiloxanes), natural polymers (e.g., cellulosic and protein based materials) and mixtures (e.g., admixtures or layered structures) or combinations thereof. In certain embodiments, the hydrophilic polymer component is polyethylene oxide and/or polyethylene glycol. In certain embodiments, the hydrophilic polymer component is a polyurethane copolymer. For example, but not by way of limitation, a hydrophobic-hydrophilic copolymer component for use in the present disclosure is a polyurethane polymer that comprises about 10% to about 50%, e.g., about 20%, hydrophilic polyethylene oxide.

In certain embodiments, the membrane includes a silicone polymer/hydrophobic-hydrophilic polymer blend. In certain embodiments, the hydrophobic-hydrophilic polymer for use in the blend can be any suitable hydrophobic-hydrophilic polymer such as, but not limited to, polyvinylpyrrolidone, polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic and graft copolymers. In certain embodiments, the hydrophobic-hydrophilic polymer is a copolymer of poly(ethylene oxide) (PEO) and poly(propylene oxide) (PPO). Non-limiting examples of PEO and PPO copolymers include PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide and blends thereof. In certain embodiments, the copolymers can be substituted with hydroxy substituents.

In certain embodiments, hydrophilic or hydrophobic modifiers can be used to "fine-tune" the permeability of the resulting membrane to an analyte of interest. In certain embodiments, hydrophilic modifiers such as poly(ethylene) glycol, hydroxyl or polyhydroxyl modifiers and the like, and any combinations thereof, can be used to enhance the biocompatibility of the polymer or the resulting membrane.

In certain embodiments where multiple active areas are present, the mass transport limiting membrane can overcoat each active area, including the option of compositional variation upon differing active areas, which can be achieved through sequential dip coating operations to produce a bilayer membrane portion upon a working electrode located closer to the sensor tip.

In certain embodiments where multiple active areas are present, a separate mass transport limiting membrane can overcoat each active area. For example, but not by way of limitation, a mass transport limiting membrane can be disposed on the first active area, e.g., an aspartate-responsive active area or an asparagine-responsive active area, and a separate, second mass transport limiting membrane can overcoat the second active area. In certain embodiments, the two mass transport limiting membranes are spatially separated and do not overlap each other. In certain embodiments, the first mass transport limiting membrane does not overlap the second mass transport limiting membrane and the second mass transport limiting membrane does not overlap the first mass transport limiting membrane. Alternatively, the second mass transport limiting membrane overlaps the first mass transport limiting membrane. In certain embodiments, the first mass transport limiting membrane comprises different polymers than the second mass transport limiting membrane. Alternatively, the first mass transport limiting membrane comprises the same polymers as the second mass transport limiting membrane. In certain embodiments, the first mass transport limiting membrane comprises the same polymers as the second mass transport limiting membrane but comprise different crosslinking agents.

In certain embodiments, the composition of the mass transport limiting membrane disposed on an analyte sensor that has two active areas can be the same or different where the mass transport limiting membrane overcoats each active area. For example, but not by way of limitation, the portion of the mass transport limiting membrane overcoating the aspartate or asparagine-responsive active area can be multi-component and/or the portion of the mass transport limiting membrane overcoating the second analyte-responsive active area can be single-component. Alternatively, the portion of the mass transport limiting membrane overcoating the aspartate or asparagine-responsive active area can be single-component and/or the portion of the mass transport limiting membrane overcoating the second analyte-responsive active area can be multi-component.

In certain embodiments, a membrane, e.g., a single-component membrane, can include a polyvinylpyridine. In certain embodiments, a membrane, e.g., a single-component membrane, can include a copolymer of vinylpyridine and styrene. In certain embodiments of the present disclosure, the aspartate or asparagine-responsive active area can be overcoated with a multi-component membrane comprising at least two polymers, e.g., a polyvinylpyridine and a polyvinylpyridine-co-styrene copolymer, either as a bilayer membrane or a homogeneous admixture, and the second analyte-responsive active area can be overcoated with a membrane comprising a single polymer, e.g., a polyvinylpyridine-co-styrene copolymer.

In certain embodiments, the mass transport limiting membrane can comprise a membrane polymer crosslinked with a crosslinking agent disclosed herein and above in section 4. In certain embodiments where there are two mass transport limiting membranes, e.g., a first mass transport limiting membrane and a second mass transport limiting membrane, each membrane can be crosslinked with a different crosslinking agent. For example, but not by way of limitation, the crosslinking agent can result in a membrane that is more restrictive to diffusion of certain compounds, e.g., analytes within the membrane, or less restrictive to diffusion of certain compounds, e.g., by affecting the size of the pores within the membrane. For example, but not by way of limitation, in a sensor that is configured to detect aspartate and/or asparagine, the mass transport limiting membrane overcoating the aspartate and/or asparagine active area can have a pore size that restricts the diffusion of compounds larger than aspartate and/or asparagine through the membrane.

In certain embodiments, crosslinking agents for use in the present disclosure can include polyepoxides, carbodiimide, cyanuric chloride, triglycidyl glycerol (Gly3), N-hydroxysuccinimide, imidoesters, epichlorohydrin or derivatized variants thereof. In certain embodiments, a membrane polymer overcoating one or more active areas can be crosslinked with a branched crosslinker, e.g., which can decrease the amount of extractables obtainable from the mass transport limiting membrane. Non-limiting examples of a branched crosslinker include branched glycidyl ether crosslinkers, e.g., including branched glycidyl ether crosslinkers that include two or three or more crosslinkable groups. In certain embodiments, the branched crosslinker can include two or more crosslinkable groups, such as polyethylene glycol diglycidyl ether. In certain embodiments, the branched crosslinker can include three or more crosslinkable groups, such as polyethylene glycol tetraglycidyl ether. In certain embodiments, the mass transport limiting membrane can include polyvinylpyridine or a copolymer of vinylpyridine and styrene crosslinked with a branched glycidyl ether crosslinker including two or three crosslinkable groups, such as polyethylene glycol tetraglycidyl ether or polyethylene glycol diglycidyl ether. In certain embodiments, the epoxide groups of a polyepoxides, e.g., polyethylene glycol tetraglycidyl ether or polyethylene glycol diglycidyl ether, can form a covalent bond with pyridine or an imidazole via epoxide ring opening resulting in a hydroxyalkyl group bridging a body of the crosslinker to the heterocycle of the membrane polymer.

In certain other embodiments, a membrane polymer overcoating one or more active areas can be crosslinked with a branched crosslinker including three or more crosslinkable groups, such as polyethylene glycol tetraglycidyl ether, which can decrease the amount of extractables obtainable from the mass transport limiting membrane, as referenced above. In certain embodiments, the mass transport limiting membrane can include polyvinylpyridine or a copolymer of vinylpyridine and styrene crosslinked with a branched glycidyl ether crosslinker including three crosslinkable groups, such as polyethylene glycol tetraglycidyl ether. In certain embodiments, the epoxide groups of the polyethylene glycol tetraglycidyl ether can form a covalent bond with pyridine or an imidazole via epoxide ring opening resulting in a hydroxyalkyl group bridging a body of the crosslinker to the heterocycle of the membrane polymer.

In certain embodiments, the crosslinking agent is polyethylene glycol diglycidyl ether (PEGDGE). In certain embodiments, the PEGDGE used to promote crosslinking (e.g., intermolecular crosslinking) between two or more membrane polymer backbones can exhibit a broad range of suitable molecular weights. In certain embodiments, the molecular weight of the PEGDGE can range from about 100 g/mol to about 5,000 g/mol. The number of ethylene glycol repeat units in each arm of the PEGDGE can be the same or different, and can typically vary over a range within a given sample to afford an average molecular weight. In certain embodiments, the PEGDGE for use in the present disclosure has an average molecular weight ($M_n$) from about 200 to 1,000, e.g., about 400. In certain embodiments, the crosslinking agent is PEGDGE 400.

In certain embodiments, the polyethylene glycol tetraglycidyl ether used to promote crosslinking (e.g., intermolecular crosslinking) between two or more membrane polymer backbones can exhibit a broad range of suitable molecular weights. Up to four polymer backbones may crosslinked with a single molecule of the polyethylene glycol tetraglycidyl ether crosslinker. In certain embodiments, the molecular weight of the polyethylene glycol tetraglycidyl ether can range from about 1,000 g/mol to about 5,000 g/mol. The number of ethylene glycol repeat units in each arm of the polyethylene glycol tetraglycidyl ether can be the same or different, and can typically vary over a range within a given sample to afford an average molecular weight. In certain embodiments, the mass transport limiting membrane can be deposited directly onto the active area In certain embodiments, polydimethylsiloxane (PDMS) can be incorporated in any of the mass transport limiting membranes disclosed herein.

In certain embodiments, an analyte sensor described herein can comprise a sensor tail comprising at least a first working electrode, a first analyte-responsive active area for detecting a first analyte disposed upon a surface of the first working electrode and a mass transport limiting membrane not permeable to the first analyte that overcoats at least the first analyte-responsive active area. In certain embodiments, the first analyte-responsive active area comprises an enzyme system responsive to a first analyte, e.g., aspartate and/or asparagine, that includes at least one enzyme responsive to the first analyte. In certain embodiments, the first analyte-responsive active area includes an electron transfer agent and/or a first polymer (and, optionally, an enzyme present within the first analyte-responsive active site is covalently bonded to the first polymer).

In certain embodiments, an analyte sensor described herein can comprises a sensor tail comprising at least a first working electrode, at least one aspartate-responsive active area comprising an aspartate oxidase (where the enzyme can be, optionally, covalently bonded to a polymer) disposed upon a surface of the first working electrode and a mass transport limiting membrane permeable to aspartate that overcoats the aspartate-responsive active area. In certain embodiments, the mass transport limiting membrane comprises a membrane polymer crosslinked with a branched glycidyl ether crosslinker comprising three or more crosslinkable groups. In certain embodiments, the aspartate-responsive active area further includes an electron transfer agent.

In certain embodiments, an analyte sensor described herein can comprise a sensor tail comprising at least a first working electrode, at least one asparagine-responsive active area comprising an enzyme system that includes an aspartate oxidase and an asparaginase (where one or both enzymes can be, optionally, covalently bonded to a polymer) disposed upon a surface of the first working electrode and a mass transport limiting membrane permeable to asparagine that overcoats the asparagine-responsive active area. In certain embodiments, the aspartate oxidase in present in a first layer and the asparaginase in present in a second layer. In certain embodiments, the aspartate oxidase and the asparaginase are present in a single layer. In certain embodiments, the mass transport limiting membrane comprises a membrane polymer crosslinked with a branched glycidyl ether crosslinker comprising three or more crosslinkable groups. In certain embodiments, the asparagine-responsive active area further includes an electron transfer agent.

In certain embodiments, an analyte sensor of the present disclosure can include a second active area configured for detecting the same analyte as the first active area or a different analyte. In certain embodiments, at least a portion of the mass transport limiting membrane that overcoats the first active area can overcoat the second active area. Alternatively or additionally, a second mass transport limiting membrane can be used to overcoat the second active area. In certain embodiments, at least a portion of the second mass transport limiting membrane that overcoats the second active area can overcoat the first active area. In certain embodiments, mass transport limiting membrane that overcoats the first active area is of a different composition that the second mass transport limiting membrane.

In certain embodiments when a first active area and a second active area configured for assaying different analytes are disposed on separate working electrodes, the mass transport limiting membrane can have differing permeability values for the first analyte and the second analyte. For example, but not by way of limitation, the mass transport limiting membrane overcoating at least one of the active areas can include an admixture of a first membrane polymer and a second membrane polymer or a bilayer of the first membrane polymer and the second membrane polymer. A homogeneous membrane can overcoat the active area not overcoated with the admixture or the bilayer, wherein the homogeneous membrane includes only one of the first membrane polymer or the second membrane polymer. Advantageously, the architectures of the analyte sensors disclosed herein readily allow a continuous membrane having a homogenous membrane portion to be disposed upon a first active area and a multi-component membrane portion to be disposed upon a second active area of the analyte sensors, thereby levelizing the permeability values for each analyte concurrently to afford improved sensitivity and detection accuracy. Continuous membrane deposition can take place through sequential dip coating operations in particular embodiments.

In certain embodiments, the mass transport limiting membrane has a thickness, e.g., dry thickness, ranging from about 0.1 μm to about 1,000 μm. e.g., from about 1 μm to about 500 μm, about 10 μm to about 100 μm or about 10 μm to about 100 μm. In certain embodiments, the mass transport limiting membrane can have a thickness from about 0.1 μm to about 100 μm, e.g., from about 1 μm to about 90 μm, from about 1 μm to about 80 μm, from about 1 μm to about 70 μm, from about 1 μm to about 60 μm, from about 1 μm to about 50 μm, from about 1 μm to about 40 μm, from about 1 μm to about 30 μm, from about 1 μm to about 20 μm, from about 0.5 μm to about 10 μm, from about 1 μm to about 10 μm, from about 1 μm to about 5 μm or from about 0.1 μm to about 5 μm. In certain embodiments, the mass transport limiting membrane can have a thickness from about 1 μm to about 100 μm.

6. Interference Domain

In certain embodiments, the sensor of the present disclosure, e.g., sensor tail, can further comprise an interference domain. In certain embodiments, the interference domain can include a polymer domain that restricts the flow of one or more interferants, e.g., to the surface of the working electrode. In certain embodiments, the interference domain can function as a molecular sieve that allows analytes and other substances that are to be measured by the working electrode to pass through, while preventing passage of other substances such as interferents. In certain embodiments, the interferents can affect the signal obtained at the working electrode. Non-limiting examples of interferents include acetaminophen, ascorbate, ascorbic acid, bilirubin, cholesterol, creatinine, dopamine, ephedrine, ibuprofen, L-dopa, methyldopa, salicylate, tetracycline, tolazamide, tolbutamide, triglycerides, urea and uric acid.

In certain embodiments, the interference domain is located between the working electrode and one or more active areas, e.g., aspartate-responsive active area and/or asparagine-responsive active area. In certain embodiments, non-limiting examples of polymers that can be used in the interference domain include polyurethanes, polymers having pendant ionic groups and polymers having controlled pore size. In certain embodiments, the interference domain is formed from one or more cellulosic derivatives. Non-limiting examples of cellulosic derivatives include polymers such as cellulose acetate, cellulose acetate butyrate, 2-hydroxyethyl cellulose, cellulose acetate phthalate, cellulose acetate propionate, cellulose acetate trimellitate and the like.

In certain embodiments, the interference domain is part of the mass transport limiting membrane and not a separate membrane. In certain embodiments, the interference domain is located between the one or more active areas and the mass transport limiting membrane.

In certain embodiments, the interference domain includes a thin, hydrophobic membrane that is non-swellable and restricts diffusion of high molecular weight species. For example, but not by way of limitation, the interference domain can be permeable to relatively low molecular weight substances while restricting the passage of higher molecular weight substances.

In certain embodiments, the interference domain can be deposited directly onto the working electrode, e.g., onto the surface of the permeable working electrode. In certain embodiments, the interference domain has a thickness, e.g., dry thickness, ranging from about 0.1 µm to about 1,000 µm, e.g., from about 1 µm to about 500 µm, about 10 µm to about 100 µm or about 10 µm to about 100 µm. In certain embodiments, the interference domain can have a thickness from about 0.1 µm to about 100 µm, e.g., from about 1 µm to about 90 µm, from about 1 µm to about 80 µm, from about 1 µm to about 70 µm, from about 1 µm to about 60 µm, from about 1 µm to about 50 µm, from about 1 µm to about 40 µm, from about 1 µm to about 30 µm, from about 1 µm to about 20 µm, from about 0.5 µm to about 10 µm, from about 1 µm to about 10 µm, from about 1 µm to about 5 µm or from about 0.1 µm to about 5 µm. In certain embodiments, the sensor can be dipped in the interference domain solution more than once. For example, but not by way of limitation, a sensor (or working electrode) of the present disclosure can be dipped in an interference domain solution at least twice, at least three times, at least four times or at least five times to obtain the desired interference domain thickness.

7. Manufacturing

The present disclosure further provides methods for manufacturing the presently disclosed analyte sensors that includes one or more active sites for detecting aspartate or asparagine.

In certain embodiments, the method includes screen printing a working electrode. In certain embodiments, the method can further include adding a composition comprising an enzyme onto a surface of the working electrode to generate an active site on the working electrode. For example, but not by way of limitation, the composition can include aspartate oxidase. In certain embodiments, the composition can further include asparaginase. In certain embodiments, the composition can further include an electron transfer agent. In certain embodiments, the composition can further include a crosslinking agent, e.g., polyethylene glycol diglycidyl ether, and a stabilizing agent, e.g., an albumin such as BSA. In certain embodiments, the method can further include curing the enzyme composition.

Alternatively, a first enzyme composition including an aspartate oxidase can be initially deposited onto a surface of the working electrode to generate an analyte-responsive active area on the working electrode. In certain embodiments, the first enzyme composition can further include a redox mediator, a crosslinking agent, e.g., polyethylene glycol diglycidyl ether, and/or a stabilizing agent, e.g., an albumin such as BSA. In certain embodiments, the method can include curing the first enzyme composition to generate a first enzyme layer. In certain embodiments, the method can include depositing a second enzyme composition including an asparaginase onto a surface of the first enzyme layer, and curing the second enzyme composition to generate a second enzyme layer. In certain embodiments, the second enzyme composition can include, a crosslinking agent, e.g., polyethylene glycol diglycidyl ether, and/or a stabilizing agent, e.g., an albumin such as BSA.

In certain embodiments, the method can further include adding a membrane composition on top of the cured enzyme composition(s). In certain embodiments, the membrane composition can include a polymer, e.g., a polyvinylpyridine, and/or a crosslinking agent, e.g., polyethylene glycol diglycidyl ether. In certain embodiments, the method can include curing the polymer composition.

Generally, the thickness of the membrane is controlled by the concentration of the membrane solution, by the number of droplets of the membrane solution applied, by the number of times the sensor is dipped in or sprayed with the membrane solution, by the volume of membrane solution sprayed on the sensor, and the like, and by any combination of these factors. In certain embodiments, the membrane described herein can have a thickness ranging from about 0.1 micrometers (µm) to about 1,000 µm, e.g., from about 1 µm to and about 500 µm, about 10 µm to about 100 µm or about 10 µm to about 100 µm. In certain embodiments, the sensor can be dipped in the membrane solution more than once. For example, but not by way of limitation, a sensor (or working electrode) of the present disclosure can be dipped in a membrane solution at least twice, at least three times, at least four times, at least five times or at least six times to obtain the desired membrane thickness.

In certain embodiments, the membrane can overlay one or more active areas, and in certain embodiments, the active areas can have a thickness from about 0.1 µm to about 100 µm, e.g., from about 1 µm to about 90 µm, from about 1 µm to about 80 µm, from about 1 µm to about 70 µm, from about 1 µm to about 60 µm, from about 1 µm to about 50 µm, from about 1 µm to about 40 µm, from about 1 µm to about 30 µm, from about 1 µm to about 20 µm, from about 0.5 µm to about 10 µm, from about 1 µm to about 10 µm, from about 1 µm to about 5 µm or from about 0.1 µm to about 5 µm. In certain embodiments, a series of droplets can be applied atop of one another to achieve the desired thickness of the active area and/or membrane, without substantially increasing the diameter of the applied droplets (i.e., maintaining the desired diameter or range thereof). In certain embodiments, each single droplet can be applied and then allowed to cool or dry, followed by one or more additional droplets. For example, but not by way of limitation, at least one droplet, at least two droplets, at least three droplets, at least four droplets or at least five droplets are added atop of one another to achieve the desired thickness of the active area.

III. METHODS OF USE

The present disclosure further provides methods of using the analyte sensors disclosed herein. In certain embodiments, the present disclosure provides methods for detecting an analyte. For example, but not by way of limitation, the present disclosure provides methods for detecting one or more analytes including aspartate and/or asparagine, e.g., in a subject in need thereof. In certain embodiments, the present disclosure provides methods for detecting aspartate. In certain embodiments, the present disclosure provides methods for detecting asparagine.

In certain embodiments, a method for detecting aspartate includes: (i) providing an analyte sensor including: (a) a sensor tail including at least a first working electrode; (b) at least one aspartate-responsive active area disposed upon a surface of a working electrode, where the aspartate-responsive active area includes an aspartate oxidase and, optionally, a first polymer and/or a redox mediator, and (c) a mass transport limiting membrane permeable to aspartate that overcoats the aspartate-responsive active area. In certain embodiments, the method further includes (ii) applying a potential, to the first working electrode; (iii) obtaining a first signal at or above an oxidation-reduction potential of the aspartate-responsive active area, the first signal being proportional to a concentration of aspartate in a fluid contacting the aspartate-responsive active area; and (iv) correlating the first signal to the concentration of aspartate in the fluid, e.g., bodily fluid.

In certain embodiments, methods for detecting aspartate can include: (i) exposing an analyte sensor to a fluid comprising aspartate; wherein the analyte sensor comprises: (a) a sensor tail comprising at least a first working electrode; (b) at least one aspartate-responsive active area disposed upon a surface of the first working electrode and responsive to aspartate, where the aspartate-responsive active area includes an aspartate oxidase and, optionally, a first polymer and/or a redox mediator; and (c) a mass transport limiting membrane permeable to aspartate that overcoats the aspartate-responsive active area; (ii) applying a potential to the first working electrode; (iii) obtaining a first signal at or above an oxidation-reduction potential of the aspartate-responsive active area, the first signal being proportional to a concentration of aspartate in the fluid; and (iv) correlating the first signal to the concentration of aspartate in the fluid, e.g., bodily fluid.

In certain embodiments, a method for detecting asparagine includes: (i) providing an analyte sensor including: (a) a sensor tail including at least a first working electrode; (b) at least one asparagine-responsive active area disposed upon a surface of a working electrode, where the asparagine-responsive active area includes an enzyme system comprising an aspartate oxidase and an asparaginase and, optionally, a first polymer and/or a redox mediator; and (c) a mass transport limiting membrane permeable to asparagine that overcoats the asparagine-responsive active area. In certain embodiments, the method further includes (ii) applying a potential, to the first working electrode; (iii) obtaining a first signal at or above an oxidation-reduction potential of the asparagine-responsive active area, the first signal being proportional to a concentration of asparagine in a fluid contacting the asparagine-responsive active area; and (iv) correlating the first signal to the concentration of asparagine in the fluid, e.g., bodily fluid. In certain embodiments, the asparagine-responsive active area includes an aspartate oxidase layer disposed upon the first working electrode and an asparaginase layer disposed upon the aspartate oxidase layer. In certain embodiments, the aspartate oxidase layer includes aspartate oxidase and a redox mediator, and the asparaginase layer includes an asparaginase. Alternatively, the asparagine-responsive active area includes an aspartate oxidase and an asparaginase in a single enzymatic layer disposed upon the first working electrode.

In certain embodiments, methods of detecting asparagine can include: (i) exposing an analyte sensor to a fluid comprising asparagine; wherein the analyte sensor comprises: (a) a sensor tail comprising at least a first working electrode; (b) an asparagine-responsive active area disposed upon a surface of the first working electrode and responsive to asparagine, where the asparagine-responsive active area includes an enzyme system comprising an aspartate oxidase and an asparaginase and, optionally, a first polymer and/or a redox mediator, and (c) a mass transport limiting membrane permeable to asparagine that overcoats the asparagine-responsive active area; (ii) applying a potential, e.g., low potential, to the first working electrode; (iii) obtaining a first signal at or above an oxidation-reduction potential of the asparagine-responsive active area, the first signal being proportional to a concentration of asparagine in the fluid; and (iv) correlating the first signal to the concentration of asparagine in the fluid, e.g., bodily fluid. In certain embodiments, the asparagine-responsive active area includes an aspartate oxidase layer disposed upon the first working electrode and an asparaginase layer disposed upon the aspartate oxidase layer. In certain embodiments, the aspartate oxidase layer includes aspartate oxidase and a redox mediator, and the asparaginase layer includes an asparaginase. Alternatively, the asparagine-responsive active area includes an aspartate oxidase and an asparaginase in a single enzymatic layer disposed upon the first working electrode.

In certain embodiments, the membrane polymer comprises a polyvinylpyridine or a polyvinylimidazole. In certain embodiments, the membrane polymer comprises a copolymer of vinylpyridine and styrene. In certain embodiments, the mass transport limiting membrane of the analyte sensor comprises a membrane polymer crosslinked with a branched crosslinker comprising three or more crosslinkable groups. In certain embodiments, the branched crosslinker comprises polyethyleneglycol tetraglycidyl ether.

IV. EXEMPLARY EMBODIMENTS

A. In certain non-limiting embodiments, the presently disclosed subject matter provides for analyte sensors comprising:
(i) a first working electrode;
(ii) at least one analyte-responsive active area disposed upon a surface of the first working electrode, wherein the analyte-responsive active area comprises an aspartate oxidase for detecting an analyte; and
(iii) a mass transport limiting membrane permeable to the analyte that overcoats at least the analyte-responsive active area.
A1. The analyte sensor of A, wherein the analyte-responsive active area further comprises an electron transfer agent.
A2. The analyte sensor of A or A1, wherein the analyte-responsive active area further comprises a stabilizing agent.
A3. The analyte sensor of any one of A2, wherein the stabilizing agent comprises an albumin.
A4. The analyte sensor of A3, wherein the albumin is a serum albumin.
A5. The analyte sensor of A4, wherein the serum albumin is human serum albumin.
A6. The analyte sensor of any one of A-A5, wherein the aspartate oxidase is covalently bonded to a polymer in the analyte-responsive active area.
A7. The analyte sensor of any one of A-A6, wherein the analyte-responsive active area further comprises a crosslinking agent.
A8. The analyte sensor of any one of A-A7, wherein the analyte is aspartate.
A9. The analyte sensor of any one of A-A8, wherein the analyte-responsive active area further comprises an asparaginase.
A10. The analyte sensor of A9, wherein the analyte is asparagine.
A11. The analyte sensor of A9 or A10, wherein the asparaginase is covalently bonded to a polymer in the analyte-responsive active area.
A12. The analyte sensor of any one of A-A11, wherein the mass transport limiting membrane comprises a polyvinylpyridine-based polymer, a polyvinylimidazole, a polyacrylate, a polyurethane, a polyether urethane, a silicone or a combination thereof.

A13. The analyte sensor of A12, wherein the mass transport limiting membrane comprises a polyvinylpyridine-based polymer.

A14. The analyte sensor of A13, wherein the polyvinylpyridine-based polymer is poly(2-vinylpyridine) or poly(4-vinylpyridine).

A15. The analyte sensor of A13, wherein the polyvinylpyridine-based polymer is a polyvinylpyridine copolymer.

A16. The analyte sensor of A15, wherein the polyvinylpyridine copolymer is a copolymer of vinylpyridine and styrene.

A17. The analyte sensor of any one of A-A16, further comprising:
(iv) a second working electrode; and
(v) a second active area disposed upon a surface of the second working electrode and responsive to a second analyte differing from the first analyte, wherein the second active area comprising at least one enzyme responsive to the second analyte.

A18. The analyte sensor of A17, wherein a second portion of the mass transport limiting membrane overcoats the second active area.

A19. The analyte sensor of A17, further comprising a second mass transport limiting membrane overcoating the second active area.

A20. The analyte sensor of A17, further comprising a second mass transport limiting membrane overcoating the second active area and the first active area.

A21. The analyte sensor of any one of A17-A20, wherein the second analyte is selected from the group consisting of glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, aspartate, asparagine, total protein, uric acid and a combination thereof.

A22. The analyte sensor of any one of A-A21, wherein the sensor tail is configured for insertion into a tissue.

A23. The analyte sensor of any one of A-A22, wherein the sensor tail is configured for insertion into a tissue for detecting the level of the analyte in vivo.

A24. The analyte sensor of any one of A9-A23, wherein the analyte-responsive active area comprises a layer comprising the asparaginase disposed upon a layer comprising the aspartate oxidase or the analyte-responsive active area comprises a single layer comprising the aspartate oxidase and the asparaginase.

B. In certain non-limiting embodiments, the presently disclosed subject matter provides a method for detecting aspartate comprising:
(i) providing an analyte sensor comprising:
  (a) a sensor tail comprising at least a first working electrode,
  (b) at least one aspartate-responsive active area disposed upon a surface of the first working electrode, wherein the aspartate-responsive active area comprises an aspartate oxidase; and
  (c) a mass transport limiting membrane permeable to aspartate that overcoats at least the aspartate-responsive active area;
(ii) applying a potential to the first working electrode;
(iii) obtaining a first signal at or above an oxidation-reduction potential of the aspartate-responsive active area, the first signal being proportional to a concentration of aspartate in a fluid contacting the aspartate-responsive active area; and
(iv) correlating the first signal to the concentration of aspartate in the fluid.

B1. The method of B, wherein the aspartate-responsive active area further comprises an electron transfer agent.

B2. The method of B or B1, wherein the aspartate-responsive active area further comprises a stabilizing agent.

B3. The method of B2, wherein the stabilizing agent comprises an albumin.

B4. The method of B3, wherein the albumin is a serum albumin.

B5. The method of B4, wherein the serum albumin is human serum albumin.

B6. The method of any one of B-B5, wherein the aspartate oxidase is covalently bonded to a polymer in the analyte-responsive active area.

B7. The method of any one of B-B6, wherein the aspartate-responsive active area further comprises a cross-linking agent.

B8. The method of any one of B-B7, wherein the mass transport limiting membrane comprises a polyvinylpyridine-based polymer, a polyvinylimidazole, a polyacrylate, a polyurethane, a polyether urethane, a silicone or a combination thereof.

B9. The method of B8, wherein the mass transport limiting membrane comprises a polyvinylpyridine-based polymer.

B10. The method of B9, wherein the polyvinylpyridine-based polymer is poly(2-vinylpyridine) or poly(4-vinylpyridine).

B11. The method of B9, wherein the polyvinylpyridine-based polymer is a polyvinylpyridine copolymer.

B12. The method of B11, wherein the polyvinylpyridine copolymer is a copolymer of vinylpyridine and styrene.

B13. The method of any one of B-B12, further comprising:
(d) a second working electrode; and
(e) a second active area disposed upon a surface of the second working electrode and responsive to a second analyte differing from the first analyte, wherein the second active area comprising at least one enzyme responsive to the second analyte.

B14. The method of B13, wherein a second portion of the mass transport limiting membrane overcoats the second active area.

B15. The method of B13, further comprising a second mass transport limiting membrane overcoating the second active area.

B16. The method of B13, further comprising a second mass transport limiting membrane overcoating the second active area and the first active area.

B17. The method of any one of B13-B16, wherein the second analyte is selected from the group consisting of glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, aspartate, asparagine, total protein, uric acid and a combination thereof.

B18. The method of any one of B-B17, wherein the sensor tail is configured for insertion into a tissue.

B19. The method of any one of B-B18, wherein the sensor tail is configured for insertion into a tissue for detecting the level of aspartate in vivo.

C. In certain non-limiting embodiments, the presently disclosed subject matter provides a method for detecting asparagine comprising:
(i) providing an analyte sensor comprising:
  (a) a sensor tail comprising at least a first working electrode,
  (b) an asparagine-responsive active area disposed upon a surface of the first working electrode, wherein the asparagine-responsive active area comprises an enzyme system comprising an aspartate oxidase and an asparaginase; and
  (c) a mass transport limiting membrane permeable to asparagine that overcoats at least the asparagine-responsive active area;
(ii) applying a potential to the first working electrode;
(iii) obtaining a first signal at or above an oxidation-reduction potential of the asparagine-responsive active area, the first signal being proportional to a concentration of aspartate in a fluid contacting the asparagine-responsive active area; and
(iv) correlating the first signal to the concentration of asparagine in the fluid.

C1. The method of C, wherein the asparagine-responsive active area further comprises an electron transfer agent.

C2. The method of C or C1, wherein the asparagine-responsive active area further comprises a stabilizing agent.

C3. The method of any one of C2, wherein the stabilizing agent comprises an albumin.

C4. The method of C3, wherein the albumin is human serum albumin.

C5. The method of any one of C-C4, wherein the asparaginase is covalently bonded to a polymer in the analyte-responsive active area.

C6. The method of any one of C-C4, wherein the asparagine-responsive active area further comprises a cross-linking agent.

C7. The method of C6, wherein the crosslinking agent is polyethylene glycol diglycidyl ether (PEGDGE).

C8. The method of any one of C-C7, wherein the mass transport limiting membrane comprises a polyvinylpyridine-based polymer, a polyvinylimidazole, a polyacrylate, a polyurethane, a polyether urethane, a silicone or a combination thereof.

C9. The method of C8, wherein the mass transport limiting membrane comprises a polyvinylpyridine-based polymer.

C10. The method of C9, wherein the polyvinylpyridine-based polymer is poly(2-vinylpyridine) or poly(4-vinylpyridine).

C11. The method of C9, wherein the polyvinylpyridine-based polymer is a polyvinylpyridine copolymer.

C12. The method of C11, wherein the polyvinylpyridine copolymer is a copolymer of vinylpyridine and styrene.

C13. The method of any one of C-C12, further comprising:
  (d) a second working electrode; and
  (e) a second active area disposed upon a surface of the second working electrode and responsive to a second analyte differing from the first analyte, wherein the second active area comprising at least one enzyme responsive to the second analyte.

C14. The method of C13, wherein a second portion of the mass transport limiting membrane overcoats the second active area.

C15. The method of C13, further comprising a second mass transport limiting membrane overcoating the second active area.

C16. The method of C13, further comprising a second mass transport limiting membrane overcoating the second active area and the first active area.

C17. The method of any one of C13-C16, wherein the second analyte is selected from the group consisting of glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, aspartate, asparagine, total protein, uric acid and a combination thereof.

C18. The method of any one of C-C17, wherein the sensor tail is configured for insertion into a tissue.

C19. The method of any one of C-C18, wherein the sensor tail is configured for insertion into a tissue for detecting the level of asparagine in vivo.

C20. The method of any one of C-C19, wherein the asparagine-responsive active area comprises a layer comprising the asparaginase disposed upon a layer comprising the aspartate oxidase.

C21. The method of any one of C-C19, wherein the asparagine-responsive active area comprises a single layer comprising the aspartate oxidase and the asparaginase.

C22. The method of any one of C-C21, wherein the aspartate oxidase is covalently bonded to a polymer in the asparagine-responsive active area.

C23. The method of any one of C-C22, wherein the asparaginase is covalently bonded to a polymer in the asparagine-responsive active area.

EXAMPLES

The presently disclosed subject matter will be better understood by reference to the following Examples, which are provided as exemplary of the presently disclosed subject matter, and not by way of limitation.

Example 1: Aspartate Sensor

The present example provides a sensor for detecting aspartate that includes the enzyme system comprising an aspartate oxidase and a redox mediator as disclosed in FIG. 22. In this analyte sensor, the redox mediator is chemically crosslinked to the aspartate oxidase enzyme. The components of Table 1 were mixed and then deposited twice onto a working electrode. After curing, some of the sensors were then dipped with an in-house made polyvinylpyridine polymer membrane composition (labeled as 10Q5-Gly3) to form sensor membranes with different thicknesses (labeled as 1×6, 2×6 and 3×6, where the first number is the number of dips in the dipping solution and the second number is the speed in mm/s at which the sensors were pulled out of the dipping solution).

TABLE 1

| Component | Final Concentration (mg/mL) in PBS |
|---|---|
| L-aspartate oxidase | 8.8 |
| BSA | 8.0 |

TABLE 1-continued

| Component | Final Concentration (mg/mL) in PBS |
|---|---|
| Redox Mediator | 8.0 |
| PEGDGE400 | 8.0 |

Figure 24:
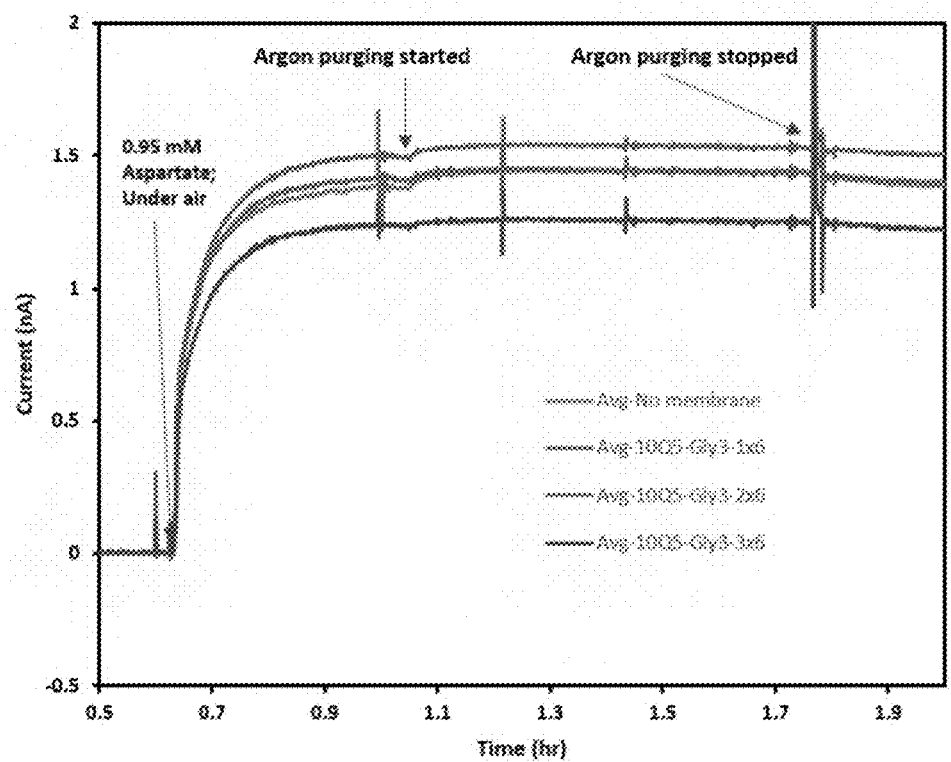
FIG. 24 shows the currents of aspartate sensors of the present disclosure under air and under argon.

The sensors were tested in the presence of 0.95 mM aspartate in 100 mM PBS solution at 33° C. under air and under argon to evaluate the effect of oxygen. An oxidase is an enzyme that catalyzes the oxidation of its substrate with oxygen, and this oxygen reaction is an undesired side reaction because it competes with the oxidation reaction by the redox mediator. As shown in FIG. 24, the sensors first showed good response under air. Sensor membrane decreased the current but not significantly. Subsequent argon purging did not change the sensors' current response, indicating that the enzyme system is very efficient to transfer the electrons from the oxidation of aspartate to the redox mediator rather than to oxygen.

Figure 25A:
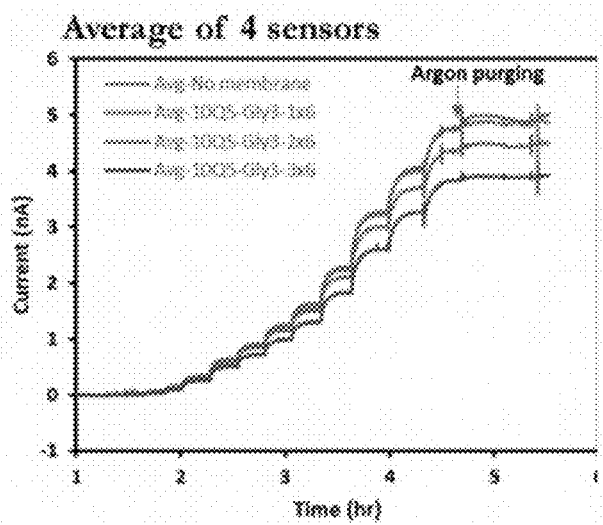
FIGS. 25A-25C show current response for aspartate analyte sensors of the present disclosure that include varying sensor membranes for aspartate detection.
Figure 25B:
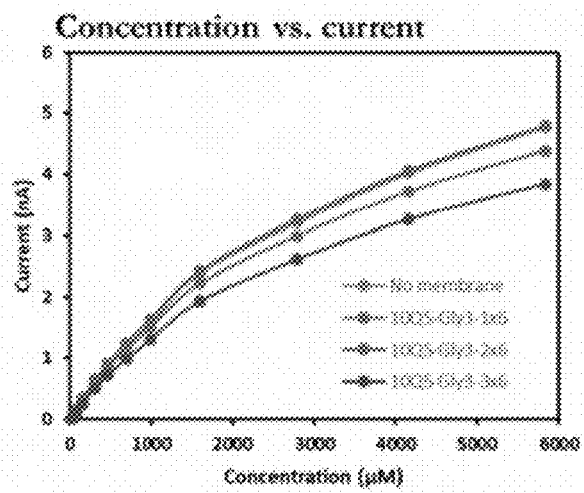
Figure 25C:
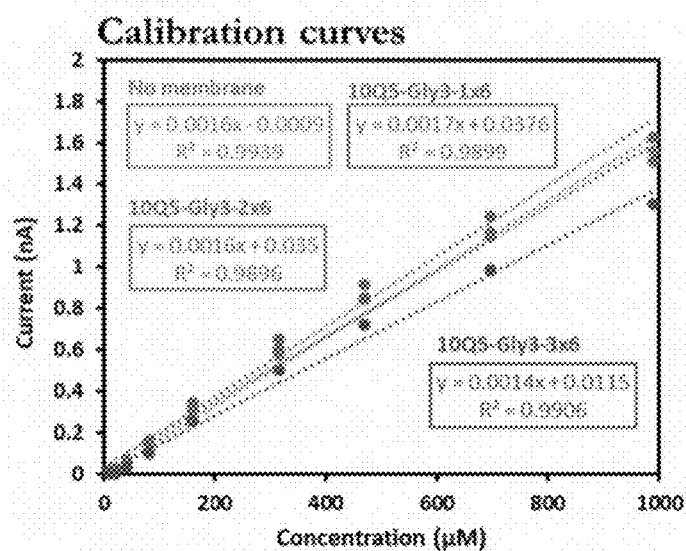

The sensors were also tested at various concentrations of aspartate to assess the signal response. As shown in FIG. 25A, current increased over the course of several minutes following exposure to a new aspartate concentration before stabilizing thereafter. FIG. 25B shows the concentration vs. current curves and FIG. 25C shows the calibration curves for each of the sensors, showing that the response is close to linear when the aspartate level is lower than 1,000 μM. Particularly, the $R^2$ values range from 0.9896 to 0.9939. Table 2 provides the sensitivity of the tested sensors at 0 to 1,000 μM aspartate.

TABLE 2

| Sensor type | Sensitivity |
|---|---|
| No membrane | 1.6 nA/mM |
| 10Q5-Gly3 1 × 6 | 1.7 nA/mM |
| 10Q5-Gly3 2 × 6 | 1.6 nA/mM |
| 10Q5-Gly3 3 × 6 | 1.4 nA/mM |

Example 2: Aspartate Sensors with Varying Amounts of Enzyme

The present example provides a sensor for detecting aspartate that includes the enzyme system comprising aspartate oxidase and a redox mediator as shown in FIG. 22. In this analyte sensor, the redox mediator and the aspartate oxidase enzyme were loaded in the aspartate-sensing layer, and the amount of enzyme was varied. The concentration of the enzyme deposited on the sensors were varied at 1×, 2×, 3× and 7×. Table 3 provides the chemical composition for the sensor referred to as 1× in FIG. 26, Table 4 provides the chemical composition for the sensor referred to as 2× in FIG. 26, Table 5 provides the chemical composition for the sensor referred to as 3× and Table 6 provides the chemical composition for the sensor referred to as 7×. The sensor referred to as 2× includes two times the amount of enzyme than the sensor referred to as 1×. For all formulations, the sensors were made by depositing a mixture including the components of Table 1 onto sensor working electrodes twice, four times or six times, which are labeled 2-pass, 4-pass and 6-pass, respectively, in FIG. 26 and Table 7. Other curing and membrane dipping procedures were the same as described in Example 1. The membrane polymer used was polyvinylpyridine and the crosslinker was PEGDGE 400, labeled as PVP+P400.

TABLE 3

| Component | Final Concentration (mg/mL) in PBS |
|---|---|
| L-aspartate oxidase | 8.8 (1X) |
| BSA | 8.0 |
| Redox Mediator | 8.0 |
| PEGDGE400 | 8.0 |

TABLE 4

| Component | Final Concentration (mg mL) in PBS |
|---|---|
| L-aspartate oxidase | 17.8 (2X) |
| BSA | 8.0 |
| Redox Mediator | 8.0 |
| PEGDGE400 | 8.0 |

TABLE 5

| Component | Final Concentration (mg/mL) in PBS |
|---|---|
| L-aspartate oxidase | 26.4 (3X) |
| BSA | 8.0 |
| Redox Mediator | 8.0 |
| PEGDGE400 | 8.0 |

TABLE 6

| Component | Final Concentration (mg/mL) in PBS |
|---|---|
| L-aspartate oxidase | 55.0 (7X) |
| BSA | 8.0 |
| Redox Mediator | 8.0 |
| PEGDGE400 | 8.0 |

Figure 26:
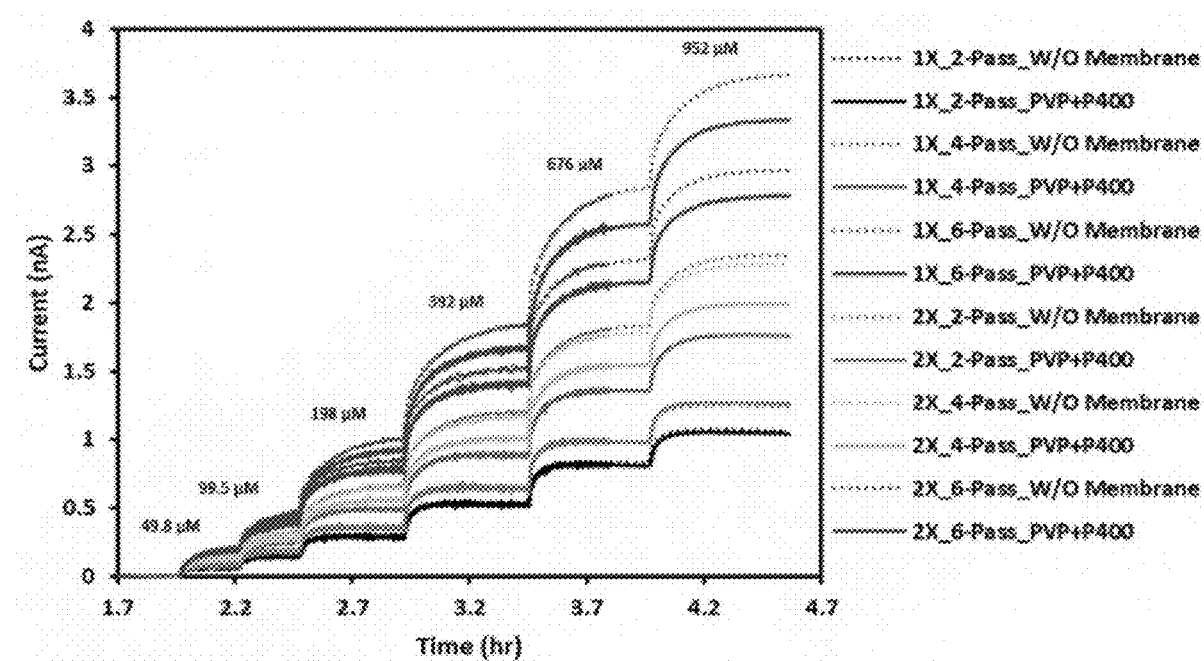
FIG. 26 shows current response for aspartate analyte sensors of the present disclosure that include varying amounts of sensing chemistry for aspartate detection.

It was found that for 3× and 7× enzyme loads, precipitation occurred in the formulation mixtures and, therefore, such sensors were not prepared. Sensors with 1× and 2× were tested at various concentrations of aspartate (49.8 μM, 99.5 μM, 198 μM, 392 μM, 676 μM and 952 μM) to assess the signal response. As shown in FIG. 26, current increased over the course of several minutes following exposure to a new aspartate concentration before stabilizing thereafter. In addition, sensors referred to as 2× exhibited a strong response in the presence of a new aspartate concentration compared to the 1× sensors. More passes of deposition also increased the sensor current for both 1× and 2× enzyme concentrations. Table 7 summarizes the sensitivities of the tested sensors with and without membrane (PVP+P400).

TABLE 7

| | Sensitivity (nA/mM) | |
|---|---|---|
| Sensor type | W/O Membrane | With Membrane |
| 1X__2-Pass | 1.08 | 1.08 |
| 1X__4-Pass | 2.43 | 1.81 |
| 1X__6-Pass | 3.06 | 2.87 |
| 2X__2-Pass | 1.29 | 1.30 |
| 2X__4-Pass | 2.36 | 2.06 |
| 2X__6-Pass | 3.81 | 3.45 |

Example 3—Aspartate Sensors with Various Redox Mediator Amounts

The aspartate sensor of the Example 2 was tested with varying amounts of a redox mediator. Particularly, as compared to Table 4, the sensor was modified by doubling the amount of the redox mediator and the enzyme, as shown in Table 8. In addition, the amount of redox mediator was reduced 3× as shown in Table 9. Table 10 provides the composition of the aspartate sensing layer that includes a reduction in the amount of the redox mediator and BSA.

TABLE 8

| Component | Final Concentration (mg/mL) |
| --- | --- |
| L-aspartate oxidase | 17.8 (2X) |
| BSA | 8.0 |
| Redox Mediator | 16 (2X) |
| PEGDGE400 | 8.0 |

TABLE 9

| Component | Final Concentration (mg/mL) |
| --- | --- |
| L-aspartate oxidase | 8.0 |
| BSA | 8 |
| Redox Mediator | 2.8 |
| PEGDGE400 | 8.0 |

TABLE 10

| Component | Final Concentration (mg/mL) |
| --- | --- |
| L-aspartate oxidase | 8.0 |
| BSA | 2.8 |
| Redox Mediator | 2.8 |
| PEGDGE400 | 8.0 |

Figure 27:
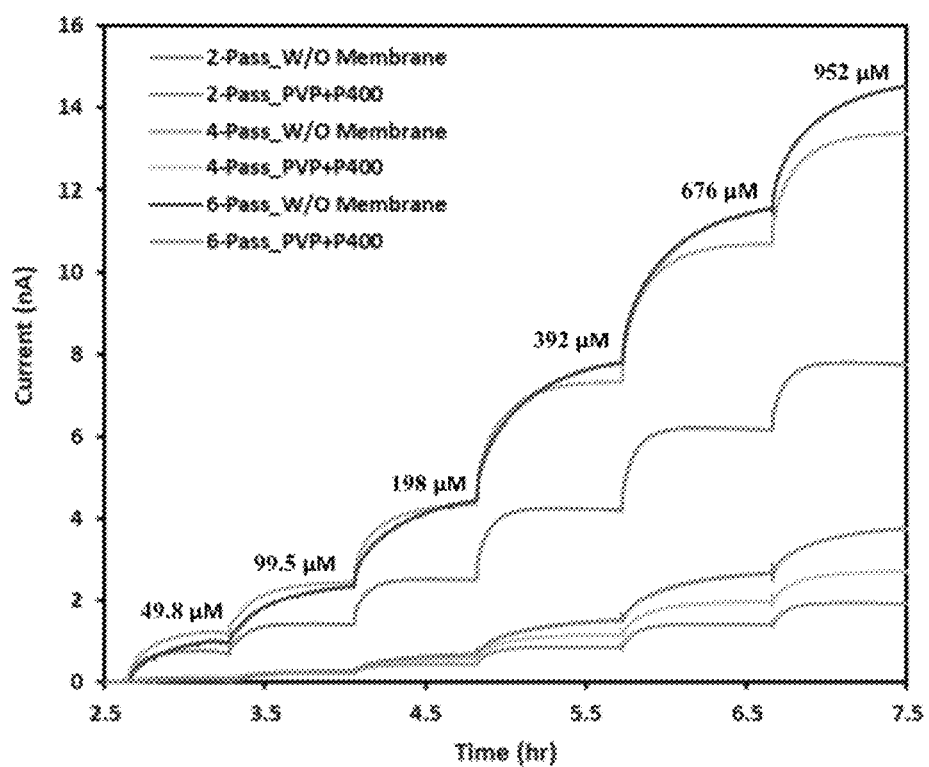
FIG. 27 shows current response for electrodes containing the enzyme system for aspartate detection with higher loads of enzyme and redox mediator with and without a membrane.

Sensors with 2× the amount of enzyme and 2× the amount of redox mediator were tested at various concentrations of aspartate to assess the signal response. As shown in FIG. 27, current increased over the course of several minutes following exposure to a new aspartate concentration before stabilizing thereafter. Table 11 provides the sensitivity of the tested sensors (nA/mM) with or without a membrane. As shown in Table 11, the amount of redox mediator has a higher impact on sensitivity than the amount of enzyme. This effect is more pronounced on the sensors without the membrane (PVP+P400).

TABLE 11

|  | Sensors including 2X enzyme and 2X redox mediator | Sensors including 2X enzyme and 1X redox mediator |
| --- | --- | --- |
| 2-Pass_W/O Membrane | 7.63 | 1.29 |
| 2-Pass_PVP + P400 | 2.01 | 1.30 |
| 4-Pass_W/O Membrane | 13.27 | 2.36 |
| 4-Pass_PVP + P400 | 2.87 | 2.06 |
| 6-Pass_W/O Membrane | 14.85 | 3.81 |
| 6-Pass_PVP + P400 | 4.09 | 3.45 |

Example 4—Asparagine Sensor: Asparaginase Layer on Top of Aspartate Sensing Layer The present example provides an example of an asparagine sensor using the enzyme system comprising an asparaginase, an aspartate oxidase and a redox mediator as shown in FIG. 23. In this example, the asparagine sensor includes an asparaginase layer on top of an aspartate sensing layer. The sensor was prepared by depositing an asparaginase layer including the components of Table 12 on top of the aspartate sensing layer compositions described in Examples 1 and 2. The asparaginases used in this sensor were purchased from Sigma (Catalog No. A3809) and ProSpec (Catalog No. ENZ-287). A subset of sensors was then dipped in a polyvinylpyridine polymer membrane solution as described in previous examples.

TABLE 12

| Component | Final Concentration (mg/mL) in PBS |
| --- | --- |
| Asparaginase | 8.8 |
| BSA | 8.0 |
| PEGDGE400 | 8.0 |

Figure 28A:
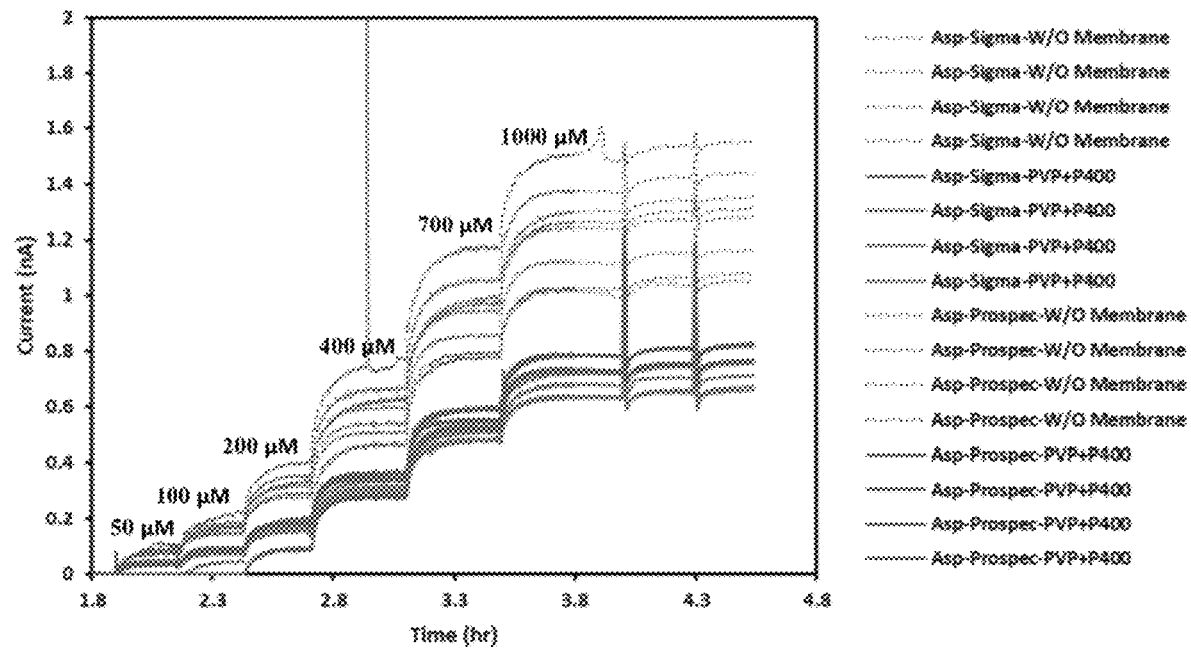
FIGS. 28A-28C show current response for electrodes containing the enzyme system for asparagine detection.
Figure 28B:
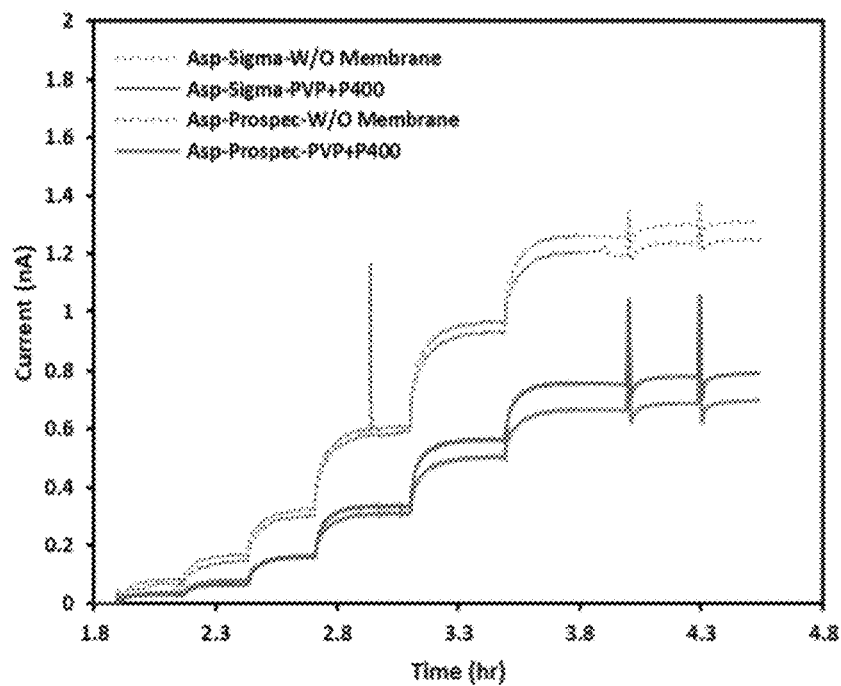
Figure 28C:
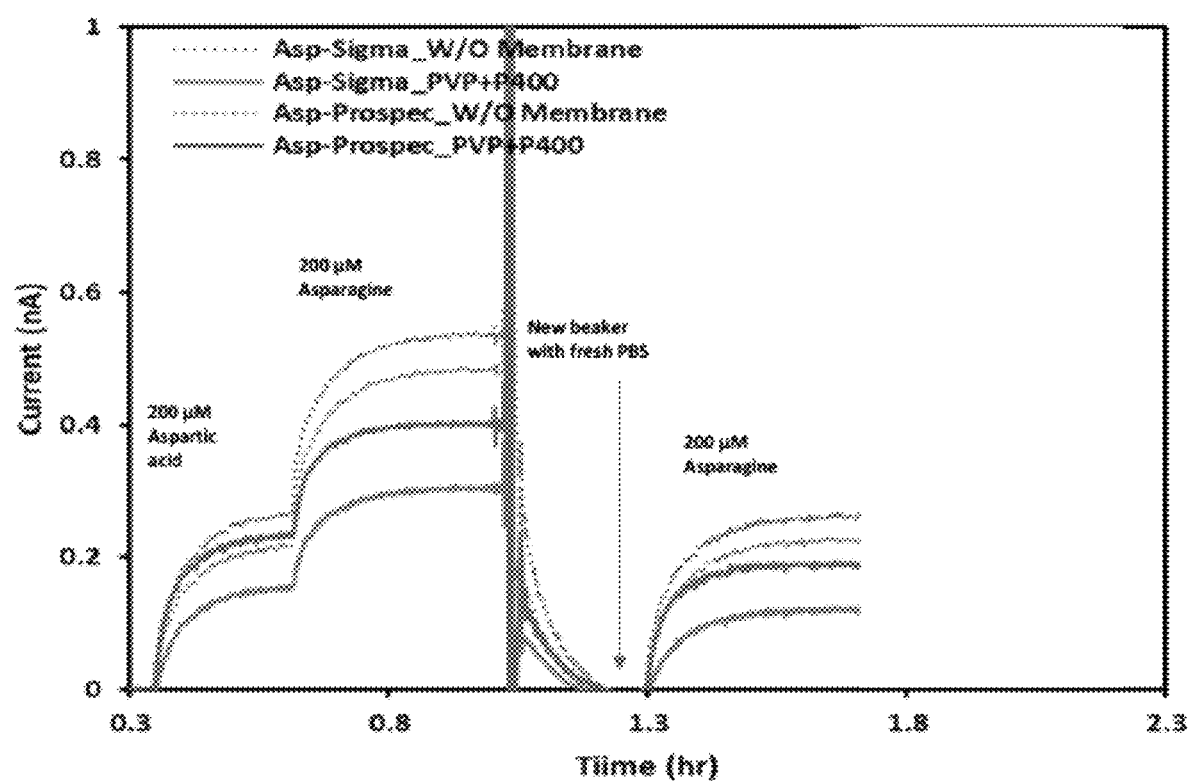

The sensors with and without a membrane were tested in the presence of varying asparagine concentrations including 50 μM, 100 μM, 200 μM, 400 μM, 700 μM and 1,000 μM. As shown in FIGS. 28A, 28B and 28C, current increased over the course of several minutes following exposure to a new asparagine concentration before stabilizing thereafter, showing that the sensors respond well to asparagine. FIG. 28B shows the average of each type of sensor shown in FIG. 28A. FIG. 28C compares the responses to aspartate and asparagine with asparagine sensors made in this example. It is expected that the enzyme system for the asparagine sensor should also respond to aspartate, which is shown in FIG. 28C.

Example 5—Asparagine Sensor: Asparaginase in the Aspartate Sensing Layer

The present example provides an example of an asparagine sensor using the enzyme system comprising an asparaginase, an aspartate oxidase and a redox mediator (as shown in FIG. 23), where the asparaginase is included in the aspartate sensing layer. The asparaginase used was purchased from ProSpec (Catalog No. ENZ-287). The sensor was prepared by depositing a mixture containing the components of Table 13 onto a working electrode. A subset of sensors was then dipped in a membrane solution.

TABLE 13

| Component | Final Concentration (mg/mL) in PBS |
| --- | --- |
| L-aspartate oxidase | 8.8 |
| Asparaginase | 0.1 |
| BSA | 8.0 |
| X7 | 8.0 |
| PEGDGE400 | 8.0 |

Figure 29:
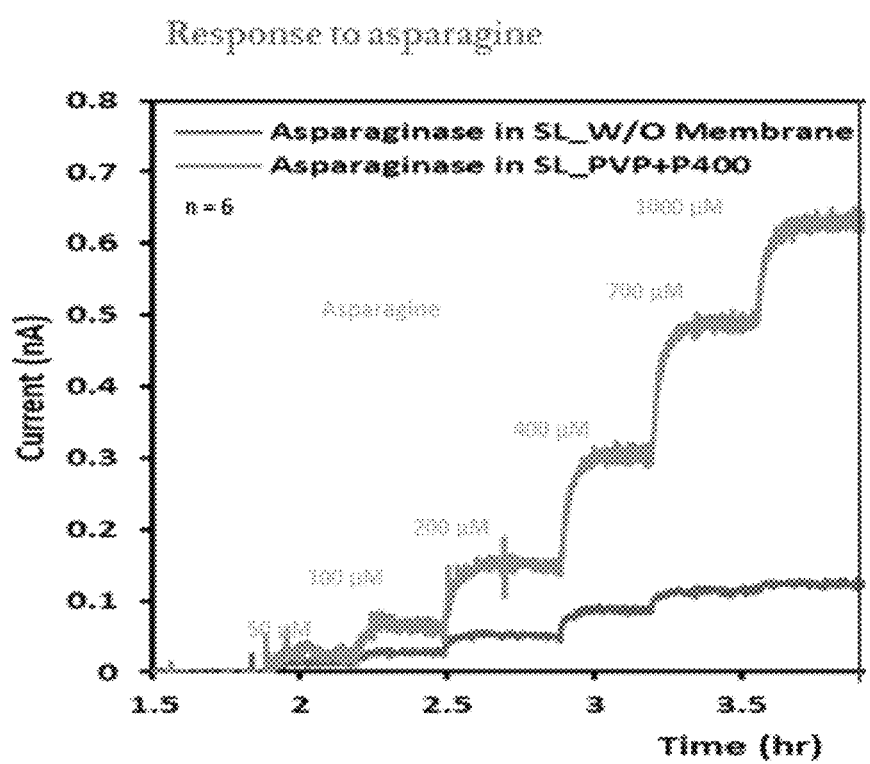
FIG. 29 shows current response for electrodes containing the enzyme system for asparagine detection with and without a membrane.

The sensors with and without a membrane were tested in the presence of varying asparagine concentration. As shown in FIG. 29, current increased over the course of several minutes following exposure to a new aspartate concentration before stabilizing thereafter. These data show that asparagine sensors that include the asparaginase in the aspartate sensing layer also respond well to asparagine.

Although the presently disclosed subject matter and its advantages have been described in detail, it should be understood that various changes, substitutions and alterations can be made herein without departing from the spirit and scope of the disclosed subject matter. Moreover, the scope of the present application is not intended to be limited to the particular embodiments of the process, machine, manufacture, and composition of matter, methods and processes described in the specification. As one of ordinary skill in the art will readily appreciate from the disclosed subject matter of the presently disclosed subject matter, processes, machines, manufacture, compositions of matter, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, methods, or steps.

Various patents, patent applications, publications, product descriptions, protocols, and sequence accession numbers are cited throughout this application, the inventions of which are incorporated herein by reference in their entireties for all purposes.

What is claimed is:

1. An analyte sensor for detecting asparagine in vivo, the sensor comprising:
   (i) at least a first working electrode;
   (ii) at least one asparagine-responsive active area for detecting asparagine, the asparagine-responsive active area disposed upon a surface of the first working electrode, wherein the asparagine-responsive active area comprises aspartate oxidase and asparaginase; and
   (iii) a mass transport limiting membrane permeable to asparagine that overcoats at least the asparagine-responsive active area,
   wherein the sensor is configured to be partially inserted into a user's skin such that a distal portion of the sensor is in contact with interstitial fluid to detect asparagine in vivo.

2. The analyte sensor of claim 1, wherein the asparagine-responsive active area further comprises an electron transfer agent.

3. The analyte sensor of claim 1, wherein the mass transport limiting membrane comprises a polyvinylpyridine-based polymer, a polyvinylimidazole, a polyacrylate, a polyurethane, a polyether urethane, a silicone or a combination thereof.

4. The analyte sensor of claim 3, wherein the mass transport limiting membrane comprises a polyvinylpyridine-based polymer.

5. The analyte sensor of claim 1, wherein one or more of the aspartate oxidase and the asparaginase are covalently bonded to a polymer in the asparagine-responsive active area.

6. The analyte sensor of claim 1, wherein the asparagine-responsive active area comprises a layer comprising the asparaginase disposed upon a layer comprising the aspartate oxidase.

7. A method for detecting asparagine in vivo, the method comprising:
   (i) exposing the analyte sensor of claim 1 to interstitial fluid comprising asparagine;
   (ii) applying a potential to the first working electrode;
   (iii) obtaining a first signal at or above an oxidation-reduction potential of the asparagine-responsive active area, the first signal being proportional to a concentration of asparagine in the interstitial fluid; and
   (iv) correlating the first signal to the concentration of asparagine in the interstitial fluid.

8. The method of claim 7, wherein the asparagine-responsive active area further comprises an electron transfer agent.

9. The method of claim 7, wherein one or more of the aspartate oxidase and the asparaginase are covalently bonded to a polymer in the asparagine-responsive active area.

10. The method of claim 7, wherein the mass transport limiting membrane comprises a polyvinylpyridine-based polymer, a polyvinylimidazole, a polyacrylate, a polyurethane, a polyether urethane, a silicone or a combination thereof.

11. The method of claim 7, wherein the asparagine-responsive active area comprises a layer comprising the asparaginase disposed upon a layer comprising the aspartate oxidase.

12. The method of claim 7, wherein the asparagine-responsive active area comprises a single layer comprising the aspartate oxidase and asparaginase.

13. The analyte sensor of claim 1, wherein the asparagine-responsive active area comprises a single layer comprising the aspartate oxidase and the asparaginase.

* * * * *